United States Patent
Ackermann et al.

(10) Patent No.: US 6,503,907 B2
(45) Date of Patent: Jan. 7, 2003

(54) INDOLE AND DIHYDROINDOLE DERIVATIVES

(75) Inventors: Jean Ackermann, Riehen (CH); Johannes Aebi, Basel (CH); Henrietta Dehmlow, Grenzach-Wyhlen (DE); Olivier Morand, Hegenheim (FR); Narendra Panday, Basel (CH); Thomas Weller, Binningen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/998,882

(22) Filed: Nov. 20, 2001

(65) Prior Publication Data

US 2002/0103247 A1 Aug. 1, 2002

(30) Foreign Application Priority Data

Nov. 28, 2000 (EP) .............................. 00125955

(51) Int. Cl.$^7$ ............................ A61K 31/535
(52) U.S. Cl. .................. 514/235.2; 544/143; 544/144; 546/201; 546/277.4; 548/467; 548/490; 548/503
(58) Field of Search ................ 544/143, 144; 548/467, 490; 514/235.2

(56) References Cited

U.S. PATENT DOCUMENTS 5,958,965 A * 9/1999 Mewshaw .................. 548/490

FOREIGN PATENT DOCUMENTS

| DE | 39 05 364 | 8/1990 |
|---|---|---|
| EP | 636 367 | 2/1995 |

OTHER PUBLICATIONS

Naruto et al, *Chemical Abstracts*, vol. 93, No. 149,357, 1980.*
Gotto et al., Circulation 81, pp. 1721–1733 (1990).
Stein et al., Nutr. Metab. Cardiovasc. Dis. 2, pp. 113–156 (1992).
Illingworth, Med. Clin. North Am. 84, pp. 23–42 (2000).
Ross et al., Arch. Intern. Med. 159, pp. 1793–1802 (1999).
Ellen et al., J. Cardiol. 81, pp. 60B–65B (1998).
Shepherd, Eur. Heart J. 16 pp. 5–13 (1995).
Davignon et al., Can. J. Cardiol 8, pp. 843–864 (1992).
Pedersen et al., Drug Safety 14, pp. 11–24 (1996).
Morand et al., J. Lipid Research 38, pp. 373–390 (1997).
Mark et al., J. Lipid Research 37, pp. 148–158 (1996).
Peffley et al., Biochem. Pharmacol 56, pp. 439–449 (1998).
Nelson et al., J. Biol. Chem. 256, pp. 1067–1068 (1981).
Spencer et al., J. Biol. Chem. 260, pp. 13391–13394 (1985).
Panini et al., J. Lipid Research 27, pp. 1190–1204 (1986).
Ness et al., Arch. Biochem Biophys. 308, pp. 420–425 (1994).
Janowski et al., Proc. Natl. Acad. Sci. USA 96, pp. 266–271 (1999).
Venkateswaran et al., J. Biol. Chem. 275, pp. 14700–14707 (2000).
Costet et al., J. Biol. Chem. 275, pp. 28240–28245 (2000).
Ordovas et al., Nutr. Rev. 58, pp. 76–79 (2000).
Schmitz et al., Front. Biosci 6, D505–D514 (2001).
Tobin et al., Mol. Endocrinol. 14, pp. 741–752 (2000).
Marshall et al., J. Org. Chem. 61(17), pp. 5729–5735 (1996).
Baker et al., J. Chem. Soc. Perkin Trans. 1, pp. 1415–1421 (1990).
Belostotskii et al., Tetrahedron Letters 35(28), pp. 5075–5076 (1994).
Wolfe et al., J. Org. Chem., 65(4), pp. 1158–1174 (2000).
Palucki et al., J. Am. Chem. Soc., 119(14), pp. 3395–3396 (1997).
Bartlett et al., J. Am. Chem. soc. 106(25), pp. 7854–7860 (1984).
Cooper et al., Synthesis (4), pp. 621–625 (2001).
Brown et al., J. Med. Chem., 43, pp. 4964–4972 (2000).
Smith et al., Tetrahedron Letters, 37, pp. 299–302 (1996).
Stara et al., Collect. Czech. Chem. Commun. 64(4), PP. 649–672 (1999).
Takeda et al., J. Am. Chem. Soc., 122, pp. 5662–5663 (2000).
Old et al., Organic Letters, 2, pp. 1403–1406 (2000).
Perregaard et al., J. Med. Chem., 35, pp. 4813–4822 (1992).

* cited by examiner

*Primary Examiner*—Robert W. Ramsuer
(74) *Attorney, Agent, or Firm*—George W. Johnston; Dennis P. Tramaloni

(57) ABSTRACT

The present invention relates to indole derivatives, dihydroindole derivatives and pharmaceutically acceptable salts and/or pharmaceutically acceptable esters thereof. The compounds are useful for the treatment and/or prophylaxis of diseases which are associated with 2,3-oxidosqualene-lanosterol cyclase such as hypercholesterolemia, hyperlipemia, arteriosclerosis, vascular diseases, mycoses, gallstones, tumors and/or hyperproliferative disorders, and treatment and/or prophylaxis of impaired glucose tolerance and diabetes.

96 Claims, No Drawings

INDOLE AND DIHYDROINDOLE DERIVATIVES

FIELD OF THE INVENTION

The present invention is concerned with novel indole and dihydroindole derivatives, their manufacture and their use as medicaments.

BACKGROUND OF THE INVENTION 2,3-oxidosqualene-lanosterol cyclase (EC 5.4.99.) is required for the biosynthesis of cholesterol, ergosterol and other sterols. Causal risk factors that directly promote the development of coronary and peripheral atherosclerosis include elevated low-density lipoprotein cholesterol (LDL-C), low high-density lipoprotein cholesterol (HDL-C), hypertension, cigarette smoking and diabetes mellitus. Other synergistic risk factors include elevated concentrations of triglyceride (TG)-rich lipoproteins, small, dense low-density lipoprotein particles, lipoprotein (a) (Lp(a)), and homocysteine. Predisposing risk factors modify the causal or conditional risk factors and thus affect atherogenesis indirectly. The predisposing risk factors are obesity, physical inactivity, family history of premature CVD, and male sex. The strong connection between coronary heart disease (CHD) and high LDL-C levels in plasma, and the therapeutic advantage of lowering elevated LDL-C levels are now well established (Gotto et al., Circulation 81, 1990, 1721–1733; Stein et al., Nutr. Metab. Cardiovasc. Dis. 2, 1992, 113–156; Illingworth, Med. Clin. North. Am. 84, 2000, 23–42). Cholesterol-rich, sometimes unstable, atherosclerotic plaques lead to the occlusion of blood vessels resulting in an ischemia or an infarct. Studies with respect to primary prophylaxis have shown that a lowering of plasma LDL-C levels in plasma reduces the frequency of non-fatal incidences of CHD, while the overall morbidity remains unchanged. The lowering of plasma LDL-C levels in patients with pre-established CHD (secondary intervention) reduces CHD mortality and morbidity; meta-analysis of different studies shows that this decrease is proportional to the reduction of the LDL-C (Ross et al., Arch. Intern. Med. 159, 1999, 1793–1802).

The clinical advantage of cholesterol lowering is greater for patients with pre-established CHD than for asymptomatic persons with hypercholesterolemia. According to current guidelines, cholesterol lowering treatment is recommended for patients who had survived a myocardial infarct or patients suffering from angina pectoris or another atherosclerotic disease, with a target LDL-C level of 100 mg/dl.

Preparations such as bile acid sequestrants, fibrates, nicotinic acid, probucol as well as statins, i.e. HMG—Co—A reductase inhibitors such as simvastatin and atorvastatin, are used for usual standard therapies. The best statins reduce plasma LDL-C effectively by at least 40%, and also plasma triglycerides, a synergistic risk factor, but less effectively. In contrast, fibratesreduce plasma triglycerides effectively, but not LDL-C. Combination of a statin and a fibrate proved to be very efficacious in lowering LDL-C and triglycerides (Ellen and McPherson, J. Cardiol. 81, 1998, 60B–65B), but safety of such a combination remains an issue (Shepherd, Eur. Heart J. 16, 1995, 5–13). A single drug with a mixed profile combining effective lowering of both LDL-C and triglycerides would provide additional clinical benefit to asymptomatic and symptomatic patients.

In humans, statins are well tolerated at standard dosage, but reductions in non-sterol intermediates in the cholesterol synthesis pathway, such as isoprenoids and coenzyme Q, may be associated with adverse clinical events at high doses (Davignon et al., Can. J. Cardiol. 8, 1992, 843–864; Pederson and Tobert, Drug Safety 14, 1996, 11–24).

This has stimulated the search for, and development of compounds that inhibit cholesterol biosynthesis, yet act distal to the synthesis of these important, non-sterol intermediates. 2,3-oxidosqualene:lanosterol cyclase (OSC), a microsomal enzyme, represents a unique target for a cholesterol-lowering drug (Morand et al., J. Lipid Res., 38, 1997, 373–390; Mark et al., J. Lipid Res. 37, 1996, 148–158). OSC is downstream of farnesyl-pyrophosphate, beyond the synthesis of isoprenoids and coenzyme Q. In hamsters, pharmacologically active doses of an OSC inhibitor showed no adverse side-effects, in contrast to a statin which reduced food-intake and body weight, and increased plasma bilirubin, liver weight and liver triglyceride content (Morand et al., J. Lipid Res., 38, 1997, 373–390). The compounds described in European Patent Application No. 636 367, which inhibit OSC and which lower the total cholesterol in plasma, belong to these substances.

OSC inhibition does not trigger the overexpression of HMGR because of an indirect, negative feed-back regulatory mechanism involving the production of 24(S),25-epoxycholesterol (Peffley et al., Biochem. Pharmacol. 56, 1998, 439–449; Nelson et al., J. Biol. Chem. 256, 1981, 1067–1068; Spencer et al., J. Biol. Chem. 260, 1985, 13391–13394; Panini et al., J. Lipid Res. 27, 1986, 1190–1204; Ness et al., Arch. Biochem. Biophys. 308, 1994, 420–425). This negative feed-back regulatory mechanism is fundamental to the concept of OSC inhibition because (i) it potentiates synergistically the primary inhibitory effect with an indirect down-regulation of HMGR, and (ii) it prevents the massive accumulation of the precursor monooxidosqualene in the liver. In addition, 24(S),25-epoxycholesterol was found to be one of the most potent agonists of the nuclear receptor LXR (Janowski et al., Proc. Natl. Acad. Sci. USA, 96, 1999, 266–271). Considering that 24(S),25-epoxycholesterol is a by-product of inhibition of OSC it is hypothesized that the OSC inhibitors of the present invention could also indirectly activate LXR-dependent pathways such as (i) cholesterol-7alpha-hydroxylase to increase the consumption of cholesterol via the bile acid route, (ii) expression of ABC proteins with the potential to stimulate reverse cholesterol transport and increase plasma HDL-C levels (Venkateswaran et al., J. Biol. Chem. 275, 2000, 14700–14707; Costet et al., J. Biol. Chem. June 2000, in press; Ordovas, Nutr Rev 58, 2000, 76–79, Schmitz and Kaminsky, Front Biosci 6, 2001, D505–D514), and/or inhibit intestinal cholesterol absorption (Mangelsdorf, XIIth International Symposium on Atherosclerosis, Stockholm, June 2000). In addition, possible cross talks between fatty acid and cholesterol metabolism mediated by liver LXR have been hypothesized (Tobin et al., Mol. Endocrinol. 14, 2000, 741–752).

SUMMARY OF THE INVENTION

The invention relates to compounds of the formula (I)

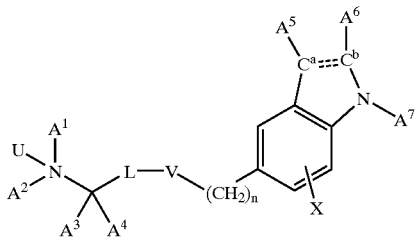

(I)

wherein
the bond ≡ between the carbon atom $C^a$ and the carbon atom $C^b$ is a single or a double bond,
U is O or a lone pair,
V is a) O, S, $NR^1$, or $CH_2$, and L is lower-alkylene or lower-alkenylene, b) —CH=CH— or —C≡C—, and L is lower-alkylene or a single bond,
n is 0 to 7,
X is hydrogen or one or more optional halogen and/or lower-alkyl substituents,
$A^1$ is hydrogen, lower-alkenyl, or lower-alkyl optionally substituted by hydroxy, lower-alkoxy, or thio-lower-alkoxy,
$A^2$ is cycloalkyl, cycloalkyl-lower-alkyl, lower-alkenyl, lower-alkinyl, heterocyclyl, or lower-alkyl optionally substituted by hydroxy, lower-alkoxy or thio-lower-alkoxy,
$A^3$ and $A^4$ independently from each other are hydrogen or lower-alkyl, or
$A^1$ and $A^2$ or $A^1$ and $A^3$ are bonded to each other to form a ring and —$A^1$—$A^2$— or —$A^1$—$A^3$— are lower-alkylene or lower-alkenylene, optionally substituted by $R^2$, in which one —$CH_2$— group of —$A^1$—$A^2$— or —$A^1$—$A^3$— can optionally be replaced by $NR^3$, S, or O,
$A^5$ and $A^6$ independently from each other are hydrogen or lower-alkyl,
$A^7$ is alkyl with two or more carbon atoms, alkenyl, alkadienyl, cycloalkyl, cycloalkyl-lower-alkyl, aryl, or aryl-lower-alkyl,
$R^2$ is hydroxy, lower-alkoxy, thio-lower-alkoxy, $N(R^4)R^5$), or lower-alkyl optionally substituted by hydroxy,
$R^1$, $R^3$, $R^4$ and $R^5$ independently from each other are hydrogen or lower-alkyl, and pharmaceutically acceptable salts and/or pharmaceutically acceptable esters thereof.

The compounds of formula I inhibit OSC and therefore also inhibit the biosynthesis of cholesterol, ergosterol and other sterols, and reduce the plasma cholesterol levels. They can therefore be used in the therapy and prophylaxis of hypercholesterolemia, hyperlipemia, arteriosclerosis and vascular diseases in general. Furthermore, they can be used in the therapy and/or prevention of mycoses, parasite infections, gallstones, cholestatic liver disorders, tumors and hyperproliferative disorders, e.g. hyperproliferative skin and vascular disorders. In addition, it has unexpectedly been found that the compounds of the present invention can also be of therapeutical use to improve glucose tolerance in order to treat and/or prevent related diseases such as diabetes. The compounds of the present invention further exhibit improved pharmacological properties compared to known compounds.

DETAILED DESCRIPTION OF THE INVENTION

Unless otherwise indicated the following definitions are set forth to illustrate and define the meaning and scope of the various terms used to describe the invention herein.

In this specification the term "lower" is used to mean a group consisting of one to seven, preferably of one to four carbon atom(s).

The term "lone pair" refers to an unbound electron pair, in particular to the unbound electron pair of a nitrogen atom in e.g. an amine.

The term "halogen" refers to fluorine, chlorine, bromine and iodine, with fluorine, chlorine and bromine being preferred.

The term "protecting group" refers to groups such as acyl, azoyl, alkoxycarbonyl, aryloxycarbonyl, or silyl. Examples are e.g. t-butyloxycarbonyl, benzyloxycarbonyl or fluorenylmethyloxycarbonyl which can be used for the protection of amino groups or trimethylsilyl, dimethyl-tert.-butyl-silyl or tert.-butyl-diphenyl-silyl, which can be used for the protection of hydroxy groups, trityl or p-methoxybenzyl for sulfur, methyl or benzyl for the protection of phenole derivatives, methyl, ethyl or tert.-butyl for the protection of thiophenole derivatives.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. Lower-alkyl groups as described below also are preferred alkyl groups. Alkyl groups can be substituted e.g. with halogen, hydroxy, lower-alkoxy, thio-lower-alkoxy, lower-alkoxy-carbonyl, $NH_2$, and/or $N$(lower-alkyl)$_2$.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like. A lower-alkyl group may have a substitution pattern as described earlier in connection with the term "alkyl".

The term "cycloalkyl" refers to a monovalent carbocyclic radical of 3 to 10 carbon atom(s), preferably 3 to 6 carbon atoms.

The term "alkoxy" refers to the group R'—O—, wherein R' is an alkyl. The term "lower-alkoxy" refers to the group R'—O—, wherein R' is a lower-alkyl. The term "thio-alkoxy" refers to the group R'—S—, wherein R' is an alkyl. The term "thio-lower-alkoxy" refers to the group R'—S—, wherein R' is a lower-alkyl.

The term "alkenyl", alone or in combination with other groups, stands for a straight-chain or branched hydrocarbon residue comprising an olefinic bond and up to 20, preferably up to 16 carbon atoms, more preferably up to 10 carbon atoms. Lower-alkenyl groups as described below also are preferred alkenyl groups. The term "lower-alkenyl" refers to a straight-chain or branched hydrocarbon residue comprising an olefinic bond and up to 7, preferably up to 4 carbon atoms, such as e.g. 2-propenyl. An alkenyl or lower-alkenyl group may have a substitution pattern as described earlier in connection with the term "alkyl".

The term "alkadienyl", alone or in combination with other groups, stands for a straight-chain or branched hydrocarbon residue comprising 2 olefinic bonds and up to 20, preferably up to 16 carbon atoms, more preferably up to 10 carbon atoms. Lower-alkadienyl groups as described below also are preferred alkadienyl groups. The term "lower-alkadienyl" refers to a straight-chain or branched hydrocarbon residue comprising 2 olefinic bonds and up to 7 carbon atoms. An alkadienyl or lower-alkadienyl group may have a substitution pattern as described earlier in connection with the term "alkyl".

The term "alkinyl", alone or in combination with other groups, stands for a straight-chain or branched hydrocarbon residue comprising a triple bond and up to 20, preferably up to 16 carbon atoms. The term "lower-alkinyl" refers to a straight-chain or branched hydrocarbon residue comprising a triple bond and up to 7, preferably up to 4 carbon atoms, such as e.g. 2-propinyl. An alkinyl or lower-alkinyl group may have a substitution pattern as described earlier in connection with the term "alkyl".

The term "alkylene" refers to a straight chain or branched divalent saturated aliphatic hydrocarbon group of 1 to 20 carbon atoms, preferably 1 to 16 carbon atoms. The term "lower-alkylene" refers to a straight chain or branched divalent saturated aliphatic hydrocarbon group of 1 to 7, preferably 1 to 6 or 3 to 6 carbon atoms. Straight chain alkylene or lower-alkylene groups are preferred. An alkylene or lower-alkylene group may have a substitution pattern as described earlier in connection with the term "alkyl".

The term "alkenylene" refers to a straight chain or branched divalent hydrocarbon group comprising an olefinic bond and up to 20 carbon atoms, preferably up to 16 carbon atoms. The term "lower-alkenylene" refers to a straight chain or branched divalent hydrocarbon group comprising an olefinic bond and up to 7, preferably up to 5, C-atoms. Straight chain alkenylene or lower-alkenylene groups are preferred. An alkenylene or lower-alkenylene group may have a substitution pattern as described earlier in connection with the term "alkyl".

The term "aryl" relates to the phenyl or naphthyl group, preferably the phenyl group, which can optionally be mono- or multiply-substituted by lower-alkyl, lower-alkinyl, dioxo-lower-alkylene (forming e.g. a benzodioxyl group), halogen, hydroxy, cyano, $CF_3$, $NH_2$, $N(lower-alkyl)_2$, aminocarbonyl, carboxy, nitro, lower-alkoxy, thio-lower-alkoxy, lower-alkylcarbonyl, lower-alkylcarbonyloxy, aryl, and/or aryloxy. Preferred substituents are halogen, $CF_3$, lower-alkyl, lower-alkinyl, and/or phenyl. More preferred substituents are fluorine, chlorine, bromine and $CF_3$.

The term "heterocyclyl" as used herein denotes optionally substituted aromatic or non-aromatic monocyclic heterocycles with 5 or 6 ring members, which comprise 1, 2 or 3 hetero atoms selected from nitrogen, oxygen and sulfur. Examples of suitable heterocycles are furyl, pyridyl, pyrimidinyl, pyrazinyl, pyridazinyl, thienyl, isoxazolyl, oxazolyl, thiazolyl, imidazolyl, pyrrolyl, 4,5-dihydro-oxazolyl, 4,5-dihydro-thiazolyl. A heterocyclyl group may have a substitution pattern as described earlier in connection with the term "aryl". An example of a heterocyclyl group having a substituent is 2-methyl-pyrimidinyl.

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, p-toluenesulphonic acid and the like, which are non toxic to living organisms. Preferred salts are formates, hydrochlorides, hydrobromides and methanesulfonic acid salts.

The term "pharmaceutically acceptable esters" embraces esters of the compounds of formula (I), in which hydroxy groups have been converted to the corresponding esters with inorganic or organic acids such as sulphuric acid, nitric acid, phosphoric acid, citric acid, formic acid, maleic acid, acetic acid, succinic acid, tartaric acid, methanesulphonic acid, p-toluenesulphonic acid and the like, which are non toxic to living organisms.

In detail, the present invention relates to compounds of formula (I)

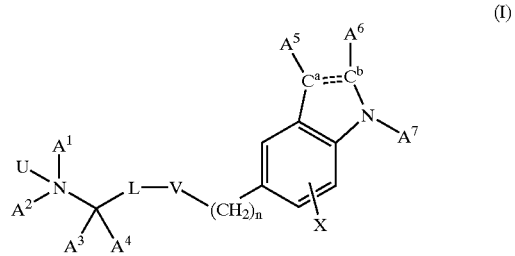

(I)

wherein
the bond === between the carbon atom $C^a$ and the carbon atom $C^b$ is a single or a double bond,
U is O or alone pair,
V is a) O, S, $NR^1$, or $CH_2$, and L is lower-alkylene or lower-alkenylene, b) —CH=CH— or —C≡C—, and L is lower-alkylene or a single bond,
n is 0 to 7,
X is hydrogen or one or more optional halogen and/or lower-alkyl substituents,
$A^1$ is hydrogen, lower-alkenyl, or lower-alkyl optionally substituted by hydroxy, lower-alkoxy, or thio-lower-alkoxy,
$A^2$ is cycloalkyl, cycloalkyl-lower-alkyl, lower-alkenyl, lower-alkinyl, heterocyclyl, or lower-alkyl optionally substituted by hydroxy, lower-alkoxy or thio-lower-alkoxy,
$A^3$ and $A^4$ independently from each other are hydrogen or lower-alkyl, or
$A^1$ and $A^2$ or $A^1$ and $A^3$ are bonded to each other to form a ring and —$A^1$—$A^2$— or —$A^1$—$A^3$— are lower-alkylene or lower-alkenylene, optionally substituted by $R^2$, in which one —$CH_2$— group of —$A^1$—$A^2$— or —$A^1$—$A^3$— can optionally be replaced by $NR^3$, S, or O,
$A^5$ and $A^6$ independently from each other are hydrogen or lower-alkyl,
$A^7$ is alkyl with two or more carbon atoms, alkenyl, alkadienyl, cycloalkyl, cycloalkyl-lower-alkyl, aryl, or aryl-lower-alkyl,
$R^2$ is hydroxy, lower-alkoxy, thio-lower-alkoxy, $N(R^4,R^5)$, or lower-alkyl optionally substituted by hydroxy,
$R^1$, $R^3$, $R^4$ and $R^5$ independently from each other are hydrogen or lower-alkyl, and pharmaceutically acceptable salts and/or pharmaceutically acceptable esters thereof.

Preferred are compounds of formula (I) and/or pharmaceutically acceptable salts thereof. Other preferred embodiments relate to compounds of formula (I) wherein U is a lone pair or to compounds of formula (I) wherein U is O.

Each of the definitions of V given above, a) and b), individually constitutes a preferred embodiment of the present invention. Compounds as described above in which V is O or $CH_2$ and L is lower-alkylene relate to a further preferred embodiment of the present invention. Further preferred compounds are those wherein V is O and L is lower-alkenylene. Other preferred compounds are those, wherein V is —C≡C— and L is lower-alkylene or a single bond. Compounds as described above, wherein n is 0 also relate to a preferred embodiment of the present invention. It is preferred that in L and $(CH_2)_n$ together there are not more than 10 carbon atoms, preferably not more than 7, more preferably not more than 5.

Other preferred compounds of the present invention are those in which $A^1$ represents hydrogen or lower-alkyl optionally substituted with hydroxy, preferably those in which $A^1$ is methyl, or ethyl optionally substituted with hydroxy. Another group of preferred compounds of the present invention are those in which $A^2$ represents cycloalkyl, cycloalkyl-lower-alkyl, lower-alkenyl, lower-alkinyl, or lower-alkyl optionally substituted by hydroxy or lower-alkoxy, with those compounds wherein $A^2$ represents lower-alkenyl, or lower-alkyl optionally substituted by hydroxy being more preferred, and with those compounds wherein $A^2$ represents methyl, ethyl, 2-hydroxy-ethyl, n-propyl, or 2-propenyl being especially preferred. In compounds wherein $A^2$ can be heterocyclyl, such a heterocyclyl group preferably is pyridinyl, 2-methyl-pyrimidinyl, 4,5-dihydro-oxazolyl or 4,5-dihydro-thiazolyl. Other preferred compounds are those wherein $A^2$ represents pyridinyl, 2-methyl-pyrimidinyl, 4,5-dihydro-oxazolyl or 4,5-dihydro-thiazolyl, preferably pyridin-4-yl.

Compounds of formula (I), wherein $A^1$ and $A^2$ are bonded to each other to form a ring and —$A^1$—$A^2$— is lower-alkylene or lower-alkenylene, optionally substituted by $R^2$, in which one —$CH_2$— group of —$A^1$—$A^2$— can optionally be replaced by O, wherein $R^2$ is hydroxy are also preferred, with those compounds wherein —$A^1$—$A^2$— is —$(CH_2)_2$—O—$(CH_2)_2$— being particularly preferred. In compounds wherein $A^1$ and $A^2$ are bonded to each other to form a ring, said ring is preferably a 4-, 5-, or 6-membered ring such as e.g. piperidinyl or pyrrolidinyl.

A further preferred embodiment of the present invention relates to compounds of formula (I), wherein $A^3$ and/or $A^4$ represent hydrogen. Further preferred compounds are those wherein $A^3$ is methyl and/or those wherein $A^4$ is methyl. Other preferred compounds are those, wherein $A^5$ is hydrogen or methyl, preferably hydrogen, and/or wherein $A^6$ is hydrogen or methyl, preferably hydrogen.

Compounds of formula (I), wherein $A^7$ is alkenyl, particularly lower-alkenyl, alkadienyl, particularly lower-alkadienyl, aryl, or aryl-lower-alkyl represent a preferred embodiment of the present invention. Other preferred compounds are those in which $A^7$ is phenyl or benzyl, optionally substituted by 1 to 3 substituents independently selected from the group concisting of fluorine, chlorine, bromine, $CF_3$, ethyl, ethinyl, and phenyl, with those compounds wherein $A^7$ is 4-fluoro-phenyl, 4-chloro-phenyl, 4-bromo-phenyl, or 4-trifluoro-phenyl being particularly preferred. $A^7$ may not be methyl. Another preferred group relates to compounds wherein X is hydrogen. Other preferred compounds are those wherein X is fluorine.

A further preferred embodiment of the present invention relates to those compounds as defined above wherein the bond ═══ between the carbon atom $C^a$ and the carbon atom $C^b$ is a double bond.

Further preferred compounds of formula (I) as defined above are those, wherein the bond ═══ between the carbon atom $C^a$ and the carbon atom $C^b$ is a single or a double bond, U is O or a lone pair, V is a) O, S, $NR^1$, or $CH_2$, and L is lower-alkylene or lower-alkenylene, b) —CH═CH— or —C≡C—, and L is lower-alkylene or a single bond, n is 0 to 7, X is hydrogen or one or more optional halogen and/or lower-alkyl substituents, $A^1$ is hydrogen, lower-alkenyl, or lower-alkyl optionally substituted by hydroxy, lower-alkoxy, or thio-lower-alkoxy, $A^2$ is cycloalkyl, cycloalkyl-lower-alkyl, lower-alkenyl, lower-alkinyl, or lower-alkyl optionally substituted by hydroxy, lower-alkoxy or thio-lower-alkoxy, $A^3$ and $A^4$ independently from each other are hydrogen or lower-alkyl, or $A^1$ and $A^2$ or $A^1$ and $A^3$ are bonded to each other to form a ring and —$A^1$—$A^2$— or —$A^1$—$A^3$— are lower-alkylene or lower-alkenylene, optionally substituted by $R^2$, in which one —$CH_2$— group of —$A^1$—$A^2$— or —$A^1$—$A^3$— can optionally be replaced by $NR^3$, S, or O, $A^5$ and $A^6$ independently from each other are hydrogen or lower-alkyl, $A^7$ is alkyl with two or more carbon atoms, alkenyl, alkadienyl, cycloalkyl, cycloalkyl-lower-alkyl, aryl, or aryl-lower-alkyl, $R^2$ is hydroxy, lower-alkoxy, thio-lower-alkoxy, $N(R^4,R^5)$, or lower-alkyl optionally substituted by hydroxy, $R^1$, $R^3$, $R^4$ and $R^5$ independently from each other are hydrogen or lower-alkyl, and pharmaceutically acceptable salts and/or pharmaceutically acceptable esters thereof.

Still more preferred embodiments of the invention are those of general formula (VII)

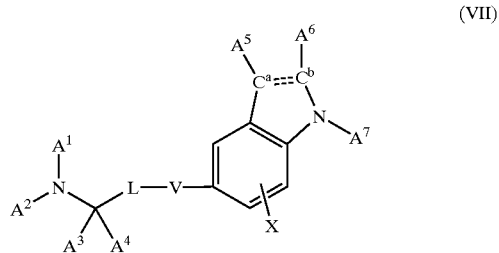

(VII)

wherein the bond ═══ between the carbon atom $C^a$ and the carbon atom $C^b$ is a single or a double bond;

V is a) O or $CH_2$ and L is lower-alkylene or lower-alkenylene or b) —C≡C— and L is lower-alkylene or a single bond;

X is hydrogen or one or more halogen substituents;

$A^1$ is hydrogen, lower-alkyl or lower-alkoxy, and $A^2$ is cycloalkyl, lower-alkenyl, lower-alkinyl, heterocyclyl or lower-alkyl optionally substituted by hydroxy, cycloalkyl or lower-alkoxy, or $A^1$ and $A^2$ are bonded to each other to form lower alkenylene, lower alkylene substituted by OH or lower alkylene in which one —$CH_2$— group is optionally substituted by O;

$A^3$, $A^4$, $A^5$ and $A^6$ are hydrogen or lower-alkyl; and $A^7$ is phenyl or lower alkyl phenyl, wherein the phenyl group is optionally substituted with halogen, phenyl, alkyl, alkinyl or trifluoromethyl; and pharmaceuticaly acceptable salts and esters thereof.

Preferred compounds of general formula (VII) are those selected from the group consisting of Cyclopropyl-{6-[1-(4-fluoro-phenyl)-1H-indol-5-yloxy]-hexyl}-methyl-amine, Allyl-{6-[1-(4-fluoro-phenyl)-1H-indol-5-yloxy]-hexyl}-methyl-amine, 1-(4-Fluoro-phenyl)-5-(6-piperidin-1-yl-hexcyloxy)-1H-indole, Allyl-{7-[1-(4-fluoro-phenyl)-1H-indol-5-yloxy]-heptyl}-methyl-amine, 1-(4-Fluoro-phenyl)-5-(7-piperidin-1-yl-heptyloxy)-1H-indole, Allyl-{4-[1-(4-fluoro-phenyl)-1H-indol-5-yloxy]-butyl}-methyl-amine, {6-[1-(4-Fluoro-phenyl)-1H-indol-5-yloxyl]-hexyl}-methyl-propyl-amine, Allyl-{5-[1-(4-fluoro-phenyl)-1H-indol-5-yl]-pent-4-ynyl}-methyl-amine,
2-(Ethyl-{5-[1-(4-fluoro-phenyl)-1H-indol-5-yl]-pent-4-ynyl}-amino)-ethanol,
Allyl-{5-[1-(4-fluoro-phenyl)-1H-indol-5-yl]-pentyl}-methyl-amine,
2-(Ethyl-{5-[1-(4-fluoro-phenyl)-1H-indol-5-yl]-pentylyl}-amino)-ethanol,
{4-[1-(4-Bromo-phenyl)-1H-indol-5-yloxy]-butyl}-diethyl-amine,
Allyl-{6-[1-(4-fluoro-phenyl)-2,3-dihydro-1H-indol-5-yloxy]-hexyl}-methyl-amine,
2-(Ethyl-{6-[1-(4-fluoro-phenyl)-2,3-dihydro-1H-indol-5-yloxy]-hexyl}-amino)-ethanol,
Allyl-{4-[1-(4-chloro-phenyl)-1H-indol-5-yloxy]-butyl}-methyl-amine,
Allyl-{5-[1-(4-chloro-phenyl)-1H-indol-5-yl]-pentyl}-methyl-amine,
Allyl-{3-[1-(4-fluoro-phenyl)-1H-indol-5-yl]-propyl}-methyl-amine,
{4-[1-(4-Bromo-phenyl)-2,3-dihydro-1H-indol-5-yloxy]-butyl}-diethyl-amine,
{4-[1-(2-Bromo-phenyl)-1H-indol-5-yloxy]-butyl}-diethyl-amine, {4-[1-(3-Bromo-phenyl)-1H-indol-5-yloxy]-butyl}-diethyl-amine,
[4-(1-Biphenyl-2-yl-1H-indol-5-yloxy, -butyl]-diethyl-amine,
Allyl-{5-[1-(2-bromo-phenyl)-1H-indol-5-yl]-pentyl}-methyl-amine,
Allyl-{5-[1-(3-bromo-phenyl)-1H-indol-5-yl]-pentyl}-methyl-amine,
Allyl-[5-(1-biphenyl-2-yl-1H-indol-5-yl)-pentyl]-methyl-amine,
{4-[1-(4-Bromo-benzyl)-1H-indol-5-yloxy]-butyl}-diethyl-amine,
Allyl-methyl-{5-[1-(4-trifluoromethyl-phenyl)-1H-indol-5-yl]-pentyl}-amine,
Allyl-methyl-[6-(1-phenyl-1H-indol-5-yloxy)-hexyl]-amine,
Diethyl-[6-(1-phenyl-1H-indol-5-yloxy)-hexyl]-amine,
2-{Ethyl-[6-(1-phenyl-1H-indol-5-yloxy)-hexyl]-amino}-ethanol,
Allyl-{4-[1-(4-fluoro-phenyl)-1H-indol-5-yloxy]-butyl}-amine,
2-(Ethyl-{4-[1-(4-fluoro-phenyl)-1H-indol-5-yloxy]-butyl}-amino)-ethanol,
Diethyl-{4-[1-(4-fluoro-phenyl)-1H-indol-5-yloxy]-butyl}-amine,
{4-[1-(4-Fluoro-phenyl)-1H-indol-5-yloxy]-butyl}-dimethyl-amine,
{4-[1-(4-Fluoro-phenyl)-1H-indol-5-yloxy]-butyl}-(2-methoxy-ethyl)-methyl-amine,
2-({4-[1-(4-Fluoro-phenyl)-1H-indol-5-yloxy]-butyl}-methyl-amino)-ethanol,
2-[{4-[1-(4-Fluoro-phenyl)-1H-indol-5-yloxy]-butyl}-(2-hydroxy-ethyl)-amino]-ethanol,
Cyclopropylmethyl-{4-[1-(4-fluoro-phenyl)-1H-indol-5-yloxy]-butyl}-methyl-amine,
1-(4-Fluoro-phenyl)-5-(4-pyrrolidin-1-yl-butoxy)-1H-indole,
Ethyl-{4-[1-(4-fluoro-phenyl)-1H-indol-5-yloxy]-butyl}-amine,
1-(4-Fluoro-phenyl)-5-(4-morpholin-4-yl-butoxy)-1H-indole,
2-{4-[1-(4-Fluoro-phenyl)-1H-indol-5-yloxy]-butylamino}-ethanol,
Ethyl-{4-[1-(4-fluoro-phenyl)-1H-indol-5-yloxy]-butyl}-(2-methoxy-ethyl)-amine,
1-{4-[1-(4-Fluoro-phenyl)-1H-indol-5-yloxy]-butyl}-piperidin-4-ol,
5-[4-(3,6-Dihydro-2H-pyridin-1-yl)-butoxy]-1-(4-fluoro-phenyl)-1H-indole,
{4-[1-(4-Fluoro-phenyl)-1H-indol-5-yloxy]-butyl}-methyl-propyl-amine,
{4-[1-(4-Fluoro-phenyl)-1H-indol-5-yloxy]-butyl}-methyl-prop-2-ynyl-amine,
1-(4-Fluoro-phenyl)-5-(4-piperidin-1-yl-butoxy)-1H-indole,
5-(4-Azetidin-1-yl-butoxy)-1-(4-fluoro-phenyl)-1H-indole,
Allyl-{3-[1-(4-fluoro-phenyl)-1H-indol-5-yloxy]-propyl}-amine,
Allyl-{3-[1-(4-fluoro-phenyl)-1H-indol-5-yloxy]-propyl}-methyl-amine,
2-(Ethyl-{3-[1-(4-fluoro-phenyl)-1H-indol-5-yloxy]-propyl}-amino)-ethanol,
Diethyl-{3-[1-(4-fluoro-phenyl)-1H-indol-5-yloxy]-propyl}-amine,
{3-[1-(4-Fluoro-phenyl)-1H-indol-5-yloxy]-propyl}-dimethyl-amine,
{3-[1-(4-Fluoro-phenyl)-1H-indol-5-yloxy]-propyl}-(2-methoxy-ethyl)-methyl-amine,
2-({3-[1-(4-Fluoro-phenyl)-1H-indol-5-yloxy]-propyl}-methyl-amino)-ethanol,
2-[{3-[1-(4-Fluoro-phenyl)-1H-indol-5-yloxy]-propyl}-(2-hydroxy-ethyl)-amino]-ethanol,
Cyclopropylmethyl-{3-[1-(4-fluoro-phenyl)-1H-indol-5-yloxy]-propyl}-methyl-amine,
1-(4-Fluoro-phenyl)-5-(3-pyrrolidin-1-yl-propoxy)-1H-indole,
Ethyl-{3-[1-(4-fluoro-phenyl)-1H-indol-5-yloxy]-propyl}-amine,
1-(4-Fluoro-phenyl)-5-(3-morpholin-4-yl-propoxy)-1H-indole,
2-{3-[1-(4-Fluoro-phenyl)-1H-indol-5-yloxy]-propylamino}-ethanol,
Ethyl-{3-[1-(4-fluoro-phenyl)-1H-indol-5-yloxy]-propyl}-(2-methoxy-ethyl)-amine,
1-{3-[1-(4-Fluoro-phenyl)-1H-indol-5-yloxy]-propyl}-piperidin-4-ol,
5-[3-(3,6-Dihydro-2H-pyridin-1-yl)-propoxy]-1-(4-fluoro-phenyl)-1H-indole,
{3-[1-(4-Fluoro-phenyl)-1-indol-5-yloxy]-propyl}-methyl-propyl-amine,
{3-[1-(4-Fluoro-phenyl)-1H-indol-5-yloxy]-propyl}-methyl-prop-2-ynyl-amine,
1-(4-Fluoro-phenyl)-5-(3-piperidin-1-yl-propoxy)-1H-indole,
5-(3-Azetidin-1-yl-propoxy)-1-(4-fluoro-phenyl)-1H-indole,
Allyl-{4-[1-(4-bromo-phenyl)-1H-indol-5-yloxy]-butyl}-methyl-amine,
{4-[1-(4-Bromo-phenyl)-1H-indol-5-yloxy]-butyl}-methyl-propyl-amine,
2-[{4-[1-(4-Bromo-phenyl)-1H-indol-5-yloxy]-butyl}-(2-hydroxy-ethyl)-amino]-ethanol,
2-({4-[1-(4-Bromo-phenyl)-1H-indol-5-yloxy]-butyl}-ethyl-amino)-ethanol,
{4-[1-(4-Bromo-phenyl)-1H-indol-5-yloxy]-butyl}-ethyl-(2-methoxy-ethyl)-amine,
5-(4-Azetidin-1-yl-butoxy)-1-(bromo-phenyl)-1H-indole,
{5-[1-(4-Bromo-phenyl)-1H-indol-5-yl]-pent-4-ynyl}-methyl-propyl-amine,
2-({5-[1-(4-Bromo-phenyl)-1H-indol-5-yl]-pent-4-ynyl}-ethyl-amino)-ethanol,
{5-[1-(4-Bromo-phenyl)-1H-indol-5-yl]-pent-4-ynyl}-dimethyl-amine, 2-({5-[1-(4-Bromo-phenyl)-1H-indol-5-yl]-pent-4-ynyl}-methyl-amino)-ethanol,
{5-[1-(4-Bromo-phenyl)-1H-indol-5-yl]-pent-4-ynyl}-(2-methoxy-ethyl)-methyl-amine,
{5-[1-(4-Bromo-phenyl)-1H-indol-5-yl]-pent-4-ynyl}-diethyl-amine,
{5-[1-(4-Bromo-phenyl)-1H-indol-5-yl]-pentyl}-methyl-propyl-amine,
2-({5-[1-(4-Bromo-phenyl)-1H-indol-5-yl]-pentyl}-ethyl-amino)-ethanol,
{5-[1-(4-Bromo-phenyl)-1H-indol-5-yl]-pentyl}-dimethyl-amine,
2-({5-[1-(4-Bromo-phenyl)-1H-indol-5-yl]-pentyl}-methyl-amino)-ethanol,
{5-[1-(4-Bromo-phenyl)-1H-indol-5-yl]-pentyl}-(2-methoxy-ethyl)-methyl-amine,
{5-[1-(4-Bromo-phenyl)-1H-indol-5-yl]-pentyl}-diethyl-amine,
2-(Ethyl-{5-[1-(4-ethynyl-phenyl)-1H-indol-5-yl]-pent-4-ynyl}-amino)-ethanol,
2-(Ethyl-{5-[1-(4-ethyl-phenyl)-1H-indol-5-yl]-pentyl}-amino)-ethanol,
Diethyl-{5-[1-(4-ethynyl-phenyl)-1H-indol-5-yl]-pent-4-ynyl}-amine,
Diethyl-{5-[1-(4-ethyl-phenyl)-1H-indol-5-yl]-pentyl}-amine,
2-({5-[1-(4-Ethynyl-phenyl)-1H-indol-5-yl]-pent-4-ynyl}-methyl-amino)-ethanol, and
2-({5-[1-(4-Ethyl-phenyl)-1H-indol-5-yl]-pentyl}-methyl-amino)-ethanol,
and pharmaceutically acceptable salts and/or pharmaceutically acceptable esters thereof.

Other preferred compounds of general formula (I) are those selected from the group consisting of
2-(Ethyl-{5-[1-(4-fluoro-phenyl)-3-methyl-1H-indol-5-yl]-pent-4-ynyl}-amino)-ethanol,
2-(Ethyl-{5-[1-(4-fluoro-phenyl)-3-methyl-1H-indol-5-yl]-pentyl}-amino)-ethanol,
Allyl-{5-[1-(4-bromo-phenyl)-3-methyl-1H-indol-5-yl]-pent-4-ynyl}-methyl-amine,
Allyl-methyl-{5-[3-methyl-1-(4-trifluoromethyl-phenyl)-1H-indol-5-yl]-pent-4-ynyl}-amine,
Allyl-{4-[1-(4-bromo-phenyl)-2-methyl-1H-indol-5-yloxy]-butyl}-methyl-amine,
Allyl-methyl-{4-[2-methyl-1-(4-trifluoromethyl-phenyl)-1H-indol-5-yloxy]-butyl}-amine,
Allyl-methyl-{4-[2-methyl-1-(4-trifluoromethyl-phenyl)-2,3-dihydro-1H-indol-5-yloxy]-butyl}-amine,
Allyl-{4-[2,3-dimethyl-1-(4-trifluoromethyl-phenyl)-1H-indol-5-yloxy]-butyl}-methyl-amine,
Allyl-{4-[1-(4-bromo-phenyl)-2,3-dimethyl-1H-indol-5-yloxy]-butyl}-methyl-amine,
2-(Ethyl-{3-[1-(4-fluoro-phenyl)-1H-indol-5-yl]-1,1-dimethyl-prop-2-ynyl}-amino)-ethanol,
1-(4-Fluoro-phenyl)-5-(3-methyl-3-piperidin-1-yl-but-1-ynyl)-1H-indole,
2-({3-[1-(4-Fluoro-phenyl)-1H-indol-5-yl]-1,1-dimethyl-prop-2-ynyl}-methyl-amino)-ethanol,
2-(Ethyl-{3-[1-(4-fluoro-phenyl)-1H-indol-5-yl]-prop-2-ynyl}-amino)-ethanol,
{4-[1-(4-Fluoro-phenyl)-1H-indol-5-yloxy]-butyl}-methyl-amine,
Allyl-{4-[1-(4-fluoro-phenyl)-1H-indol-5-yloxy]-but-2-enyl}-methyl-amine,
2-(Ethyl-{4-[1-(4-fluoro-phenyl)-1H-indol-5-yloxy]-but-2-enyl}-amino)-ethanol,
Allyl-{4-[1-(4-chloro-phenyl)-6-fluoro-1H-indol-5-yloxyl]-butyl}-methyl-amine,
Allyl-{4-[6-fluoro-1-(4-fluoro-phenyl)-1H-indol-5-yloxy]-butyl}-methyl-amine,
2-({4-[1-(4-Chloro-phenyl)-6-fluoro-1H-indol-5-yloxy]-butyl}-methyl-amino)-ethanol,
2-({4-[6-Fluoro-1-(4-fluoro-phenyl)-1H-indol-5-yloxy]-butyl}-methyl-amino)-ethanol,
2-({4-[1-(4-Chloro-phenyl)-6-fluoro-1H-indol-5-yloxy]-butyl}-ethyl-amino)-ethanol,
2-(Ethyl-{4-[6-fluoro-1-(4-fluoro-phenyl)-1H-indol-5-yloxy]-butyl}-amino)-ethanol,
Allyl-{5-[6-fluoro-1-(4-fluoro-phenyl)-1H-indol-5-yl]-pent-4-ynyl}-methyl-amine,
2-({5-[6-Fluoro-1-(4-fluoro-phenyl)-1H-indol-5-yl]-pent-4-ynyl}-ethyl-amino)-ethanol,
Allyl-{4-[1-(4-chloro-phenyl)-6-fluoro-2,3-dihydro-1H-indol-5-yloxy]-butyl}-methyl-amine,
(4,5-Dihydro-oxazol-2-yl)-{4-[1-(4-fluoro-phenyl)-1H-indol-5-yloxy]-butyl}-methyl-amine,
(4,5-Dihydro-thiazol-2-yl)-{4-[1-(4-fluoro-phenyl)-1H-indol-5-yloxy]-butyl}-methyl-amine,
{4-[1-(4-Fluoro-phenyl)-1H-indol-5-yloxy]-butyl}-methyl-pyridin-4-yl-amine,
{4-[1-(4-Fluoro-phenyl)-1H-indol-5-yloxy]-butyl}-methyl-pyridin-3-yl-amine,
{4-[1-(4-Fluoro-phenyl)-1H-indol-5-yloxy]-butyl}-methyl-pyridin-2-yl-amine, and
{4-[1-(4-Fluoro-phenyl)-1H-indol-5-yloxy]-butyl}-methyl-(2-methyl-pyrimidin-4-yl)-amine,
and pharmaceutically acceptable salts and/or pharmaceutically acceptable esters thereof.

Still more preferred embodiments of the invention are those of general formula (VIII)

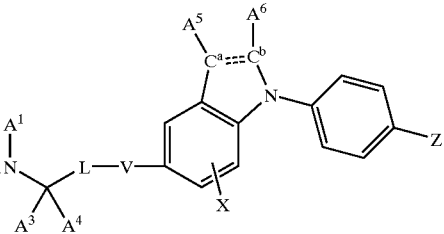

(VIII)

wherein
the bond ==== between the carbon atom $C^a$ and the carbon atom $C^b$ is a single or a double bond;
V is a) O or $CH_2$ and L is lower-alkylene or lower-alkenylene or b) —C≡C— and L is lower-alkylene or a single bond;
X is hydrogen or one or more halogen substituents;
Z is halogen or trifluoromethyl;
$A^1$ is lower-alkyl or lower-alkoxy, and $A^2$ is lower-alkyl, lower alkoxy, lower-alkenyl or a heterocyclyl having a single N hetero atom, or
$A^1$ and $A^2$ are bonded to each other to form lower-alkylene in which one —$CH_2$— group is optionally substituted by O; and
$A^3$, $A^4$, $A^5$ and $A^6$ are hydrogen or lower-alkyl; and
pharmaceutically acceptable salts and esters thereof.
Particularly preferred compounds of general formula (VIII) are those selected from the group consisting of
Allyl-{6-[1-(4-fluoro-phenyl)-1H-indol-5-yloxy]-hexyl}-methyl-amine,
2-(Ethyl-{4-[1-(4-fluoro-phenyl)-1H-indol-5-yloxy]-butyl}-amino)-ethanol,
1-(4-Fluoro-phenyl)-5-(4-morpholin-4-yl-butoxy)-1H-indole, Diethyl-{4-[1-(4-fluoro-phenyl)-1H-indol-5-yloxy]-butyl}-amine,
2-({4-[1-(4-Bromo-phenyl)-1H-indol-5-yloxy]-butyl}-ethyl-amino)-ethanol,
Allyl-{5-[1-(4-chloro-phenyl)-1H-indol-5-yl]-pentyl}-methyl-amine,
2-[{4-[1-(4-Fluoro-phenyl)-1H-indol-5-yloxy]-butyl}-(2-hydroxy-ethyl)-amino]-ethanol,
{4-[1-(4-Fluoro-phenyl)-1H-indol-5-yloxy]-butyl}-methyl-propyl-amine,
Allyl-{4-[1-(4-fluoro-phenyl)-1H-indol-5-yloxy]-butyl}-methyl-amine,
Allyl-{6-[1-(4-fluoro-phenyl)-2,3-dihydro-1H-indol-5-yloxy]-hexyl}-methyl-amine, and
2-(Ethyl-{5-[1-(4-fluoro-phenyl)-1H-indol-5-yl]-pentyl}-amino)-ethanol, and pharmaceutically acceptable salts and/or pharmaceutically acceptable esters thereof.

Other particularly preferred compounds of general formula (VIII) are those selected from the group consisting of
Allyl-{5-[1-(4-fluoro-phenyl)-1H-indol-5-yl]-pentyl}-methyl-amine, and pharmaceutically acceptable salts thereof.

Other particularly preferred compounds of general formula (VIII) are those selected from the group consisting of
2-({4-[1-(4-Chloro-phenyl)-6-fluoro-1H-indol-5-yloxy]-butyl}-ethyl-amino)-ethanol,
{4-[1-(4-Fluoro-phenyl)-1H-indol-5-yloxy]-butyl}-methyl-pyridin-4-yl-amine,
2-({4-[1-(4-Chloro-phenyl)-6-fluoro-1H-indol-5-yloxy]-butyl}-methyl-amino)-ethanol,
2-(Ethyl-{4-[1-(4-fluoro-phenyl)-1H-indol-5-yloxy]-but-2-enyl}-amino)-ethanol,
Allyl-{5-[1-(4-bromo-phenyl)-3-methyl-1H-indol-5-yl]-pent-4-ynyl}-methyl-amine,
2-(Ethyl-{3-[1-(4-fluoro-phenyl)-1H-indol-5-yl]-1,1-dimethyl-prop-2-ynyl}-amino)-ethanol,
2-(Ethyl-{5-[1-(4-fluoro-phenyl)-3-methyl-1H-indol-5-yl]-pentyl}-amino)-ethanol,
Allyl-methyl-{5-[3-methyl-1-(4-trifluoromethyl-phenyl)-1H-indol-5-yl]-pent-4-ynyl}-amine,
Allyl-{4-[6-fluoro-1-(4-fluoro-phenyl)-1H-indol-5-yloxy]-butyl}-methyl-amine,
2-({4-[6-Fluoro-1-(4-fluoro-phenyl)-1H-indol-5-yloxy]-butyl}-methyl-amino)-ethanol,
2-(Ethyl-{4-[6-fluoro-1-(4-fluoro-phenyl)-1H-indol-5-yloxy]-butyl}-amino)-ethanol, and
2-(Ethyl-{5-[6-fluoro-1-(4-fluoro-phenyl)-1H-indol-5-yl]-pent-4-ynyl}-amino)-ethanol, and pharmaceutically acceptable salts and/or pharmaceutically acceptable esters thereof.

Compounds of formula (I) can have one or more asymmetric carbon atoms and can exist in the form of optically pure enantiomers or as racemats. The invention embraces all of these forms.

It will be appreciated, that the compounds of general formula (I) in this invention may be derivatised at functional groups to provide derivatives which are capable of conversion back to the parent compound in vivo.

The present invention also relates to a process for the manufacture of compounds as described above, which process comprises
reacting a compound of formula (II)

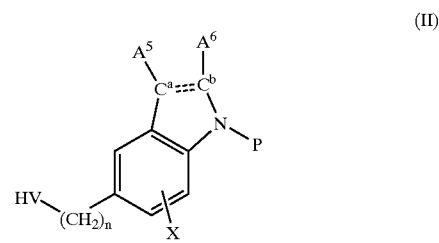

with a compound $(A^1, A^2, U)N-C(A^3, A^4)-L-M$, wherein V is O, S or $NR^1$, M is mesylate, tosylate, triflate, Cl, Br or I, P is $A^7$ or a protecting group, and U, $A^1$, $A^2$, $A^3$, $A^4$, $A^5$, $A^6$, $A^7$, X, L, n, $R^1$ and the bond === between the carbon atom $C^a$ and the carbon atom $C^b$ have the significances given above, or wherein HV is mesylate, tosylate, Cl, Br or I, and M is OH, SH or $NHR^1$, and $R^1$ has the significance given above, or b) reacting a compound of formula (III)

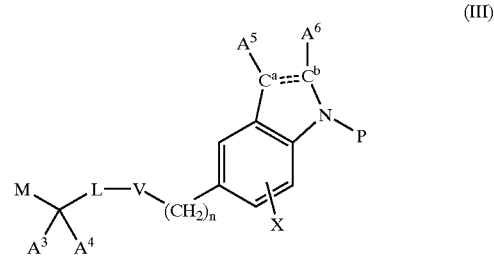

with a compound $NHA^1, A^2$, wherein M is mesylate, tosylate, triflate, Cl, Br or I, P is $A^7$ or a protecting group, and $A^1$, $A^2$, $A^3$, $A^4$, $A^5$, $A^6$, $A^7$, L, V, X, n and the bond === between the carbon atom $C^a$ and the carbon atom $C^b$ are as defined above, or c) reacting a compound of formula (IV)

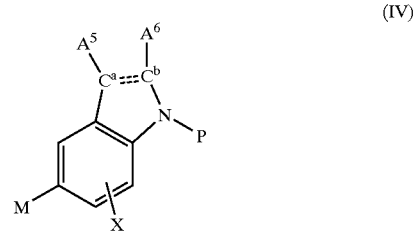

with a compound $(A^1, A^2, U)N-C(A^3, A^4)-L-C\equiv CH$, wherein M is Cl, Br, I or $F_3CO_2SO$, P is $A^7$ or a protecting group, and U, $A^1$, $A^2$, $A^3$, $A^4$, $A^5$, $A^6$, $A^7$, U, L, X and the bond === between the carbon atom $C^a$ and the carbon atom $C^b$ are as defined above, or d) reacting a compound of formula (V)

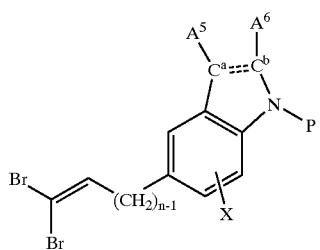

(V)

with a compound $(A^1,A^2,U)N—C(A^3,A^4)—L—M$, wherein M is mesylate, tosylate, triflate, Cl, Br or I, P is $A^7$ or a protecting group, and $A^1$, $A^2$, $A^3$, $A^4$, $A^5$, $A^6$, $A^7$, U, L, X, n and the bond ≡ between the carbon atom $C^a$ and the carbon atom $C^b$ are as defined above, or e) hydrogenating a compound of formula (VI)

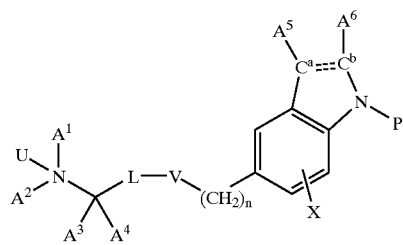

(VI)

wherein V is —C≡C—, P is $A^7$ or a protecting group, and $A^1$, $A^2$, $A^3$, $A^4$, $A^5$, $A^6$, $A^7$, U, L, X and n are as defined above, and optionally removing the protecting group P and introducing group $A^7$, and optionally converting a compound of formula (I) as defined above to a pharmaceutically acceptable salt, and optionally converting a compound of formula (I) as defined above, wherein U is a lone pair, to a corresponding compound wherein U is O.

Preferred processes as described above are those, in which P is $A^7$.

The invention further relates to compounds of formula (I) as defined above, when manufactured according to a process as defined above.

As described above, the compounds of formula (I) of the present invention can be used for the treatment and/or prophylaxis of diseases which are associated with OSC such as hypercholesterolemia, hyperlipemia, arteriosclerosis, vascular diseases, mycoses, parasite infections and gallstones, and/or treatment and/or prophylaxis of impaired glucose tolerance, diabetes, tumors and/or hyperproliferative disorders, preferably for the treatment and/or prophylaxis of hypercholesterolemia and/or hyperlipemia. Hyperproliferative skin and vascular disorders particularly come into consideration as hyperproliferative disorders.

The invention therefore also relates to pharmaceutical compositions comprising a compound as defined above and a pharmaceutically acceptable carrier and/or adjuvant.

Further, the invention relates to compounds as defined above for use as therapeutic active substances, particularly as therapeutic active substances for the treatment and/or prophylaxis of of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia.

In another embodiment, the invention relates to a method for the treatment and/or prophylaxis of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia, which method comprises administering a compound as defined above to a human being or animal.

The invention further relates to the use of compounds as defined above for the treatment and/or prophylaxis of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia.

In addition, the invention relates to the use of compounds as defined above for the preparation of medicaments for the treatment and/or prophylaxis of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia. Such medicaments comprise a compound as defined above.

The compounds of formula (I) can be manufactured by the methods given below, by the methods given in the examples or by analogous methods. Appropriate reaction conditions for the individual reaction steps are known to the person skilled in the art. Starting materials are either commercially available or can be prepared by methods analogous to the methods given below or in the examples or by methods known in the art, e.g. by methods described in: Richard J. Sundberg Indoles (Best Synthetic Methods), Series Editor A. R. Katritzky, O. Meth-Cohn, C. W. Rees, Acedemic Press, San Diego 1996, or inHouben-Weyl Methoden der Organischen Chemie, R. P. Kreker, Ed., Georg Thieme Verlag, Stuttgart, 1994, Bd E 6a,6b, or in Takeda, A.; Kamijo, S.; Yamamoto*, Y. Journal Amercian Chemical Society 2000, 122, 5662–63. and references cited therein.

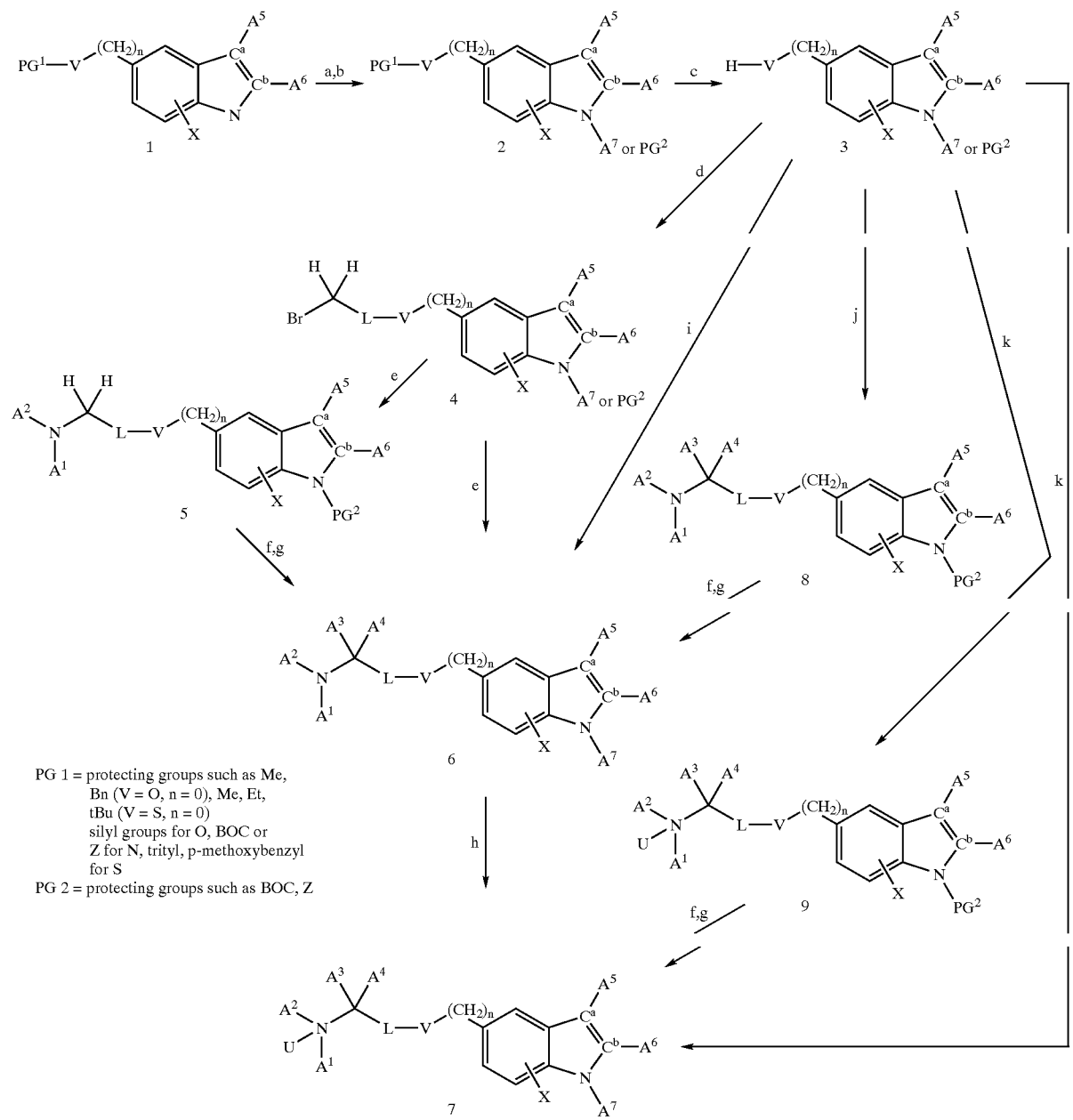
Scheme 1
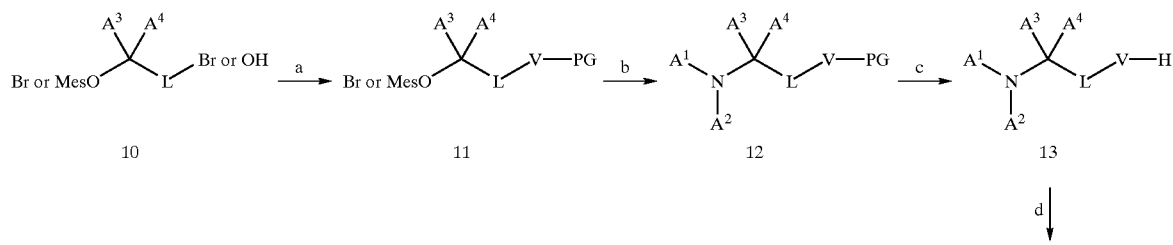
Scheme 2

PG = protecting group, such as trityl for V = sulfur or BOC for V = NR¹

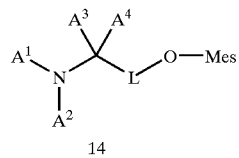

14

Scheme 3

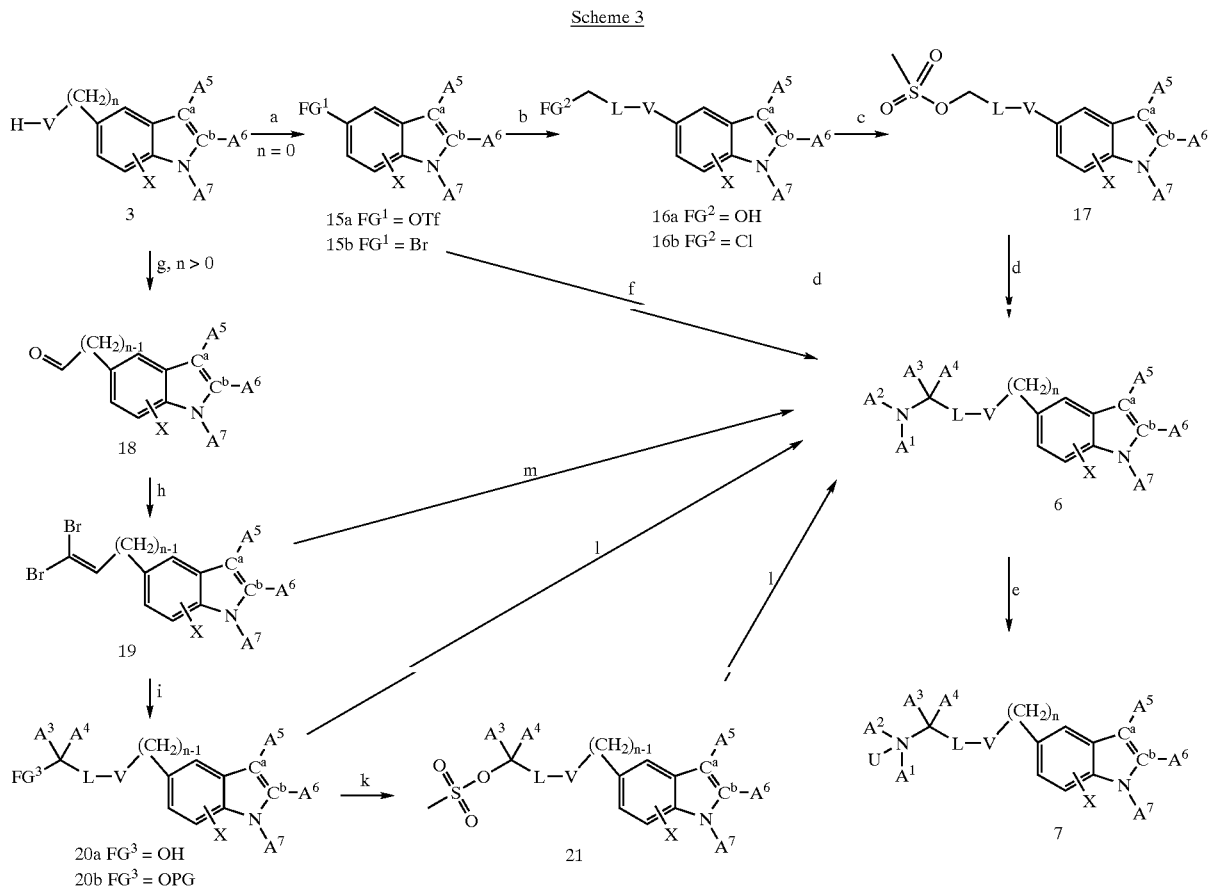

SCHEME 1

In scheme 1, the preparation of compounds of the present invention in which V is O, S or NR¹ is outlined. Indole derivative 2 might be derived from a suitable protected indole derivative 1 by N-arylation by treatment e.g. with A) Cu, KOH and the desired halo-benzene derivative, or with B) fluorobenzene derivatives, 18-crown-6, KF on alox in DMSO (analogously to William J. Smith III, J. Scott Sawyer, Tetrahedron Letters 1999, Vol.37, No.3, 299–302.) or C) by palladium catalysized N-arylation (see David W. Old, Michele C. Harris, Stephen L. Buchwald Organic Letters 2000, 2,10,1403–1406.), D) CuI, ZnO, $K_2CO_3$, halobenzene (see Jens Perregaard et. al. J. Med. Chem. 1992, 35, 4813–4822.). For other N-substituted indoles $A^7$ may be introduced by treatment with NaH and the corresponding electrophile in THF or DMF (step a). In the cases, in which a protecting group like BOC is introduced first, the indole derivative 1 can be treated with potassium tert. butylate followed by di-tert.-dibutylcarbonate in solvents such as DMF or THF (step a). If desired the indole system can be reduced to the corresponding indoline derivative 2 for example by employing $NaCNBH_3$ in TFA (step b).

Furthermore, for the formation of the indoline compound 2 the reduction (e.g. with $NaCNBH_3$) might be performed prior to introducing a protecting group for the nitrogen (e.g.$PG^2$=BOC) or before introducing the moiety $A^7$.

V-Deprotection might be achieved, in the case of 5-benzyloxyindole derivatives or 5-benzyloxyindoline 2 by hydrogenation with e.g. Pd/C in solvents like methanol or ethyl acetate, in the case of 5-methoxy-indole derivatives 2 by treatment for example with lithium-tri-sec-butylborohydride in THF. For V=S, NR¹ or V=O and n>0, deprotection using procedures known in the art (step c) gives the free HV-building block 3.

Alkylation of the phenol/thiophenol 3 (V=O, S, n=0) is accomplished in solvents such as acetone, DMF, DMA with $K_2CO_3$ and a suitable dihaloalkane or dihaloalkene (halogene is here represented by bromine, but can also be chlorine or iodine. It is also possible to use mesylates, tosylates or triflates instead of halogenides) at 0° C. to reflux to yield halogenide 4 (step d). For the preparation of derivatives 4 (V=O, n>0), the alcohol 3 can be treated with α,ω-dihaloalkanes or α,ω-dihaloalkenes under phase transfer conditions e.g. α,ω-dihaloalkanes/dihaloalkenes, NaOH, nBu$_4$NHSO$_4$. For V=S, O or NR$^1$, the derivative 3 may be treated with α,ω-dihaloalkane in the presence of NaH in DMF 0° C. to RT to yield bromide 4. For shorter alkanes (methyl, ethyl), the method of choice is the in situ generation of the haloalkane-triflate (from the corresponding haloalkanol with trifluoromethansulfonic anhydride/2,6-di-tert-butylpyridine in CH$_2$Cl$_2$ at 0° C.). This haloalkane-triflate may then be reacted with 3 in the presence of a base such as 2,6-di-tert-butylpyridine in nitromethane at 60° C. to yield bromide 4 [analogously to a procedure of Belostotskii, Anatoly M.; Hassner, Alfred. Synthetic methods. 41. Etherification of hydroxysteroids via triflates. Tetrahedron Lett. (1994), 35(28), 5075].

Compound 4 can be converted to the amine 5 or 6 with an excess of the corresponding amine NHA$^1$A$^2$ in a suitable solvent such as DMA, DMF, MeOH at RT or at 50–65° C. or with amine NHA$^1$A$^2$, sodium hydride in DMF, DMA or THF. (step e). Compound 5 might be N-deprotected using basic conditions like aqueous NaOH in an alkohol for the indole derivatives or by treatment with TFA in CH$_2$Cl$_2$ at RT or reflux for the indoline derivatives. Introduction of the moiety A$^7$ may be accomplished as described for step a to give compound 6.

Furthermore a conversion of the indoline derivative to the indole compound is possible e.g. using a halobenzene in DMSO in the presence of K$_2$CO$_3$ and CuI at elevated temperature.

Alternatively, the compound 3 may be transferred to the amine 6 or 8 by attaching the pre-assembled fragment A$^1$A$^2$NC(A$^3$A$^4$)LV-OMes/halogenide, which can be synthesised by known methods (shown e.g. in Scheme 2), using alkylating conditions (step i). Heteroaromate 3 (V=O, n>0) can also be mesylated 3 (V=OMes) and then reacted with A$^1$A$^2$NC(A$^3$A$^4$)L-VH (synthesis described Scheme 2) in e.g. DMF with NaH as base to give 6 or 8 (with V=O, S, NR$^1$). Compound 8 can be converted to 6 as described earlier for the conversion of derivative 5 to 6.

If A$^2$=H, heterocyclic moieties A$^2$ may be introduced by treatment with halo heterocycles in the presence of Huenig's base in DMF (Ger. Offen. (1990), DE3905364 A1). Alternatively, Buchwald conditions e.g. Pd(OAc)$_2$, 2-(Dicyclohexylphosphino) biphenyl, NaOtBu in toluene might be applied (John P. Wolfe, Hiroshi Tomori, Joseph P. Sadighi, Jingjun Yin, and Stephen L. Buchwald, J. Org. Chem., 65 (4), 1158–1174, 2000). For the preparation of oxazoline or thiaoxazolines the amine maybe treated with chloroethylisocyanate or chloroethylthioisocyanate in THF, followed by treatment with a base such as triethylamine or ammonium hydroxide (George R. Brown, David M. Hollinshead, Elaine S. E. Stokes, David Waterson, David S. Clarke, Alan J. Foubister, Steven C. Glossop, Fergus McTaggart, Donald J. Mirrlees, Graham J. Smith, and Robin Wood Journal of Medicinal Chemistry, 2000, 43, 26, 4964–72.).

Furthermore, the indole moiety of amine 6 may be reduced to indoline 6 using sodium cyanoborohydride as described for compound 2 (see above, step b).

Amine 6 maybe converted to a salt or to the N-oxide 7 (step h). For N-oxide 7 (V=O) a mixture of hydrogen peroxide urea adduct and phthalic anhydride in CH$_2$Cl$_2$ at RT may be used. For the preparation of the N-oxides 7 (V=S or NR$^1$) an alternative route has to be employed (step k): Oxidation of the pre-assembled fragment A$^1$A$^2$NC(A$^3$A$^4$) L-OMes/halogenide to the corresponding N-oxide derivative, followed by alkylation of the compound 3 to give compound 7 or 9. Compound 9 may be transferred to 7 as described above for compound 5 by cleavage of the protecting group and introduction of A$^7$.

For an amine 6 or for compounds 2 or 3 in which A$^7$ is a halo- or hydroxy-substituted aromatic system (in case of the later, the corresponding triflate may be synthesized) the corresponding alkyne, alkyl, alkene, amine, alkoxy or thioalkoxy substituted A$^7$ derivative can be synthesized employing Sonogashira reaction or palladium catalyzed amination, C—O or C—S coupling reactions. For the Sonogashira reaction, the arylhalogenide or aryltriflate may be treated with a suitable alkyne or alkynol in THF in the presence of a base such as triethylamine or piperidine with a catalytic amount of e.g. Pd(PPh$_3$)$_4$/CuI or Pd(OAc)$_2$/CuI or PdCl$_2$(PPh$_3$)$_2$/CuI at 45° C. to 80°. These alkynes can then be reduced selectively. The introduction of an amine moiety may be achieved using primary or secondary amines and the arylhalogenide or aryltriflate using methods developed by Buchwald e.g. tris(Dibenzylideneacetone)dipalladium, 2(di-tertbutylphosphino)Biphenyl in toluene and Natrium tert-butylat as base to give the resulting substituted 2,3 or 6 [e.g. Wolfe, John P.; Tomori, Hiroshi; Sadighi, Joseph P.; Yin, Jingjun; Buchwald, Stephen L. Simple, efficient catalyst system for the palladium-catalyzed amination of aryl chlorides, bromides, and triflates. J. Org. Chem. (2000), 65(4), 1158–1174]. Other compounds with substituted A$^7$ groups can e.g. be prepared according to the methods described in Palucki, Michael; Wolfe, John P.; Buchwald, Stephen L. Palladium-Catalyzed Intermolecular Carbon-Oxygen Bond Formation: A New Synthesis of Aryl Ethers. J. Am. Chem. Soc. (1997), 119(14), 3395–3396.

The resulting substituted amines 6 can then be transformed to compounds 7.

SCHEME 2

Scheme 2 shows the synthesis of amino-VH sidechain 13 that may be used for the synthesis of compounds with the corresponding V-spacers (V=NR$^1$, S, or O). α,ω-dihaloalkane, mesyl-alkanyl-halogenide, α,ω-dihaloalkene or mesyl-alkenyl-halogenide 10 may be treated with a suitable protected amine (HNR$^1$-PG, PG=protecting group, e.g. BOC) in DMA or a thiol (HS-PG e.g., triphenylmethanethiol) in the presence of NaH in DMA to give the compound 11 (step a). Treatment with the amine A$^1$A$^2$NH yields the S- or N-protected amine 12 (step b) or in the case of α,ω-halo-alkanol or α,ω-haloalkenol 10 directly amino-alcohol 13. N-deprotection with procedures known in the art e.g. TFA in CH$_2$Cl$_2$ gives the amine side chain 13 (step c). The deprotection of the thiol moiety in 12 may be achieved with TFA/triisopropylsilane in CH$_2$Cl$_2$ at 0° C. to RT to yield the aminothiol 13 (step c). Aminoalkanol 13 can be transformed further to mesylate 14 (step d).

SCHEME 3

In Scheme 3, the preparation of compounds of formula 7, in which V represents —CH$_2$—, —CH═CH— or —C≡C— is outlined. The starting material is 5-hydroxyindol or 5-hydroxydihydroindol derivative 3, which may be transformed to the triflate 15a in pyridine with trifluoromethanesulfonic anhydride at 0° C. to RT (step a). Sonogashira-coupling (step b) of the triflate 15a and a suitable alkynol or alkynechloride in piperidine with Pd(PPh$_3$)$_4$/CuI at 45° C. to 80° C. in analogy to a literature procedure yields alcohol 16a or chloride 16b [Stara, Irena G.; Stary, Ivo; Kollarovic, Adrian; Teply, Filip; Saman, David; Fiedler, Pavel. Coupling reactions of halobenzenes with alkynes. The synthesis of phenylacetylenes and symmetrical or unsymmetrical 1,2-diphenylacetylenes. Collect. Czech. Chem. Commun. (1999), 64(4), 649–672.]. In case of $A^7$=Bromo or Iodo-substituted aromatic system, triflate 15 is dissolved in THF with $PdCl_2(PPh_3)_2$ as catalyst and alkynol or alkynechloride, triphenylphosphine, triethylamine and a catalytic amount of CuI to give alkyne 16a or 16b.

Alternatively, the alkynes 16a or 16b can be prepared by Sonogashira reaction of the 5-bromo-indol derivatives 15b with the corresponding alkynols or alkynechlorides.

Mesylation of alcohol 16a with methanesulfonylchloride e.g. in pyridine with DMAP (reaction step c) and subsequent amination (reaction step d) of the resulting mesylate 17 with a suitable amine $NHA^1A^2$ in a solvent like DMA, DMF or MeOH at RT or at 50–65° C. optionally in the presence of a base such as Huenig's base, $NEt_3$, pyridine yields the amine 6. Alcohol 16a can also be treated with trifluoromethane sulfonic acid anhydride and Huenig's base at −15° C. in $CH_2Cl_2$ (in situ generation of the corresponding triflate) followed by treatment with the corresponding amine $NHA^1A^2$ at −15° C. to RT. This is especially the method of choice for but-3-yn-1-ol-derivatives 16a. Chloride 16b can be transformed directly or via iodide (Finkelstein reaction) to the amine 6, as described above (step d). Compounds 6 in which V is —$CH_2$— or —CH═CH— can be obtained by hydrogenation of compound 6 in EtOH with $Pt_2O.H_2O$ (yields the saturated analogue 6) or by selective hydrogenation with other known methods (yields the double bond analogue 6). Optionally, the hydrogenation described above can be performed at an earlier stage e.g. the alcohol 16a or mesylate 17.

Alternatively, the group $A^1A^2NC(A^3A^4C)L$-acetylene can be synthesised by known methods and attached to compound 15a or 15b (Sonogashira-coupling), to yield the compounds of the present invention 6 (reaction step f).

Compounds of the formula 6 (n>0) may be synthesised by Swern oxidation of the alcohol 3 (V=O and n>0) to give the corresponding aldehyde 18 (step g) as an intermediate. The aldehyde 18 may be treated with triphenylphosphine, tetrabromo-methane and triethylamine in $CH_2Cl_2$ at 0° C. to RT to yield 2,2-Dibromo-vinyl derivative 19 (step h). Rearrangement with n-BuLi (ca 1.6 M in hexane) in THF at −78° C., followed by reaction with formaldehyde (−78° C. to RT) leads to the propargyl alcohol 20a (step i, side chain extension through application of the Corey-Fuchs method), following conditions described in: Marshall, James A.; Bartley, Gary S.; Wallace, Eli M. Total Synthesis of the Pseudopterane (−)-Kallolide B, the Enantiomer of Natural (+)-Kallolide B. J. Org. Chem. (1996), 61(17), 5729–5735; and Baker, Raymond; Boyes, Alastair L.; Swain, Christopher J. Synthesis of talaromycins A, B, C, and E. J. Chem. Soc., Perkin Trans. 1 (1990), (5), 1415–21.

For longer side chains, the rearrangement is performed with n-BuLi (ca 1.6 M in hexane) in THF at −78° C. as above, followed by addition of a co-solvens such as DMPU and reaction with O-protected 1-bromo-alcohols (e.g. 1-bromo-n-tetrahydro-pyaranyloxyalkane) to yield the O-protected compounds 20b (step i). O-protected compounds 20b can be deprotected to the corresponding alkynol 20a (in MeOH at 50–60° C., in the presence of catalytic amount of pyridinium toluene-4-sulfonate). Alcohol 20a can be reacted with Huenig's base/trifluoromethane sulfonic acid anhydride at −15° C. in $CH_2Cl_2$ (in situ generation of the corresponding triflate) followed by treatment with Huenig's base and the corresponding amine $NHA^1A^2$ at −15° C. to RT to give amine 6. Alternatively, mesylation of alcohol 20a with methanesulfonylchloride, pyridine and DMAP in $CH_2Cl_2$ at 0° C. to RT gives mesylate 21. Conversion of the mesylate 21 to the amine 6 can be accomplished with an excess of the corresponding amine $NHA^1A^2$ in DMA at RT or as described above (step l).

Compounds 6 in which V is —$CH_2$— or —CH═CH— can be obtained by hydrogenation of compound 6 itself or the intermediates 20a, 20b or 21. The hydrogenation may be done in EtOH with $Pt_2O.H_2O$ (yields the saturated analogues 6, 20a, 20b, or 21) or by selective hydrogenation to the double bond with other known methods and transforming the intermediates afterwards to 5.

Alternatively, for the introduction of the group $A^1A^2N$ $(A^3A^4C)L$ in which $A^3$ and/or $A^4$ are not H, the following steps have to be performed starting from compound 19 (step m or steps i and l): for L=lower alkanes, the building block $A^1A^2N(A^3A^4C)L$-halogenide/mesylate is synthesised by known methods (or in analogy to the methods described in Scheme 2) and introduced (step m) under the same condition as described above for step i. For L=single bond, the introduction of the group $A^1A^2N(A^3A^4C)$ with $A^3$ and/or $A^4$ not H, a two step procedure has to be followed: first the rearrangement of 19 with n-BuLi (ca 1.6 M in hexane) in THF at −78° C., followed by reaction with the corresponding aldehyde ($A^3$ or $A^4$—COH) or ketone ($A^3COA^4$, at −78° C. to RT) leads to the $A^3A^4$ substituted propargyl alcohol 20a (step i) which is e.g. mesylated or transformed to a phosphorester or a chloride (not shown) and reacted with the desired $A^1A^2$-substituted-amine in the presence of Tetrakis (triphenylphosphine)palladium (for the phosphorester) or Cu(I)Cl/Cu bronze and Huenig's base (for the chloride) to yield the desired $A^3,A^4$-substituted compound 6 (step l). (see: Bartlett, Paul A.; McQuaid, Loretta A. Total synthesis of (□)-methyl shikimate and (□)-3-phosphoshikimic acid. J. Am. Chem. Soc. (1984), 106(25), 7854–60 and Cooper, Matthew A.; Lucas, Mathew A.; Taylor, Joanne M.; Ward, A. David; Williamson, Natalie M. A convenient method for the aromatic amino-Claisen rearrangement of N-(1,1-disubstituted-allyl)anilines. Synthesis (2001), (4), 621–625.)

For an amine 6 in which $A^7$ is a halo-substituted aromatic system, the corresponding alkyne, alkyl, alkene, amine, alkoxy or thioalkoxy substituted derivative can be synthesized employing Sonogashira reaction or palladium catalyzed amination, C—O or C—S coupling reactions (as described for compound 3 in scheme 1) (or in case of a hydroxy substitution, the corresponding triflate may be synthesized).

If $A^2$=H, heterocyclic moieties $A^2$ maybe introduced by treatment with halo heterocycles in the presence of Huenig's base in DMF (Ger. Offen. (1990), DE3905364 A1). Alternatively, Buchwald conditions e.g. $Pd(OAc)_2$, 2-(Dicyclohexylphosphino) biphenyl, NaOtBu in toluene might be applied (John P. Wolfe, Hiroshi Tomori, Joseph P. Sadighi, Jingjun Yin, and Stephen L. Buchwald, J. Org. Chem., 65 (4), 1158–1174, 2000). For the preparation of oxazoline or thiaoxazolines the amine may be treated with chloroethylisocyanate or chloroethylthioisocyanate in THF, followed by treatment with a base such as triethylamine or ammonium hydroxide (George R. Brown, David M. Hollinshead, Elaine S. E. Stokes, David Waterson, David S. Clarke, Alan J. Foubister, Steven C. Glossop, Fergus McTaggart, Donald J. Mirrlees, Graham J. Smith, and Robin Wood Journal of Medicinal Chemistry, 2000, 43, 26, 4964–72.).

Furthermore, the indole moiety of amine 6 may be reduced to indoline 6 using a reducing agent such as sodium cyanoborohydride as described above (see scheme 1, step b).

Amine 6 may be converted to a salt or to the N-oxide 7 using a mixture of hydrogen peroxide urea adduct and phthalic anhydride in $CH_2Cl_2$ at RT (step e).

In the cases, in which a modification of $A^7$ is envisaged to be done at the end of the synthesis, the synthesis might be carried out as described in scheme 3 with $A^7$=PG. The protecting group can be cleaved under basic conditions like aqueous NaOH in an alkohol for the indole derivatives or by treatment with TFA in $CH_2Cl_2$ at RT or reflux for the indoline derivatives. Introduction of the moiety $A^7$ may be accomplished as described in Scheme 1 for step a to give compound 6. Furthermore, a conversion of the indoline derivative to the indole compound is possible e.g. using a halobenzene in DMISO in the presence of $K_2CO_3$ and CuI at elevated temperature.

The following tests were carried out in order to determine the activity of the compounds of formula I and their salts. Inhibition of Human Liver Microsomal 2,3-oxidosqualene-lanosterol Cyclase (OSC)

Liver microsomes from a healthy volunteer were prepared in sodium phosphate buffer (pH 7.4). The OSC activity was measured in the same buffer, which also contained 1 mM EDTA and 1 mM dithiothreitol. The microsomes were diluted to 0.8 mg/ml protein in cold phosphate buffer. Dry [$^{14}$C]R,S-monooxidosqualene (MOS, 12.8 mCi/mmol) was diluted to 20 nCi/µl with ethanol and mixed with phosphate buffer-1% BSA (bovine serum albumin). A stock solution of 1 mM test substance in DMSO was diluted to the desired concentration with phosphate buffer-1% BSA. 40 µl of microsomes were mixed with 20 µl of the solution of the test substance and the reaction was subsequently started with 20 µl of the [$^{14}$C]R,S-MOS solution. The final conditions were: 0.4 mg/ml of microsomal proteins and 30 µl of [$^{14}$C]R,S-MOS in phosphate buffer, pH 7.4, containing 0.5% albumin, DMSO <0.1% and ethanol <2%, in a total volume of 80 µl.

After 1 hour at 37° C. the reaction was stopped by the addition of 0.6 ml of 10% potassium hydroxide-methanol, 0.7ml of water and 0.1 ml of hexane:ether (1:1, v/v) which contained 25 µg of non-radioactive MOS and 25 µg of lanosterol as carriers. After shaking, 1 ml of hexane:ether (1:1, v/v) was added to each test tube, these were again shaken and then centrifuged. The upper phase was transferred into a glass test tube, the lower phase was again extracted with hexane:ether and combined with the first extract. The entire extract was evaporated to dryness with nitrogen, the residue was suspended in 50 µl of hexane:ether and applied to a silica gel plate. Chromatographic separation was effected in hexane:ether (1:1, v/v) as the eluent. The Rf values for the MOS substrate and the lanosterol product were 0.91 and, respectively, 0.54. After drying, radioactive MOS and lanosterol were observed on the silica gel plate. The ratio of MOS to lanosterol was determined from the radioactive bands in order to determine the yield of the reaction and OSC inhibition.

The test was carried out on the one hand with a constant test substance concentration of 100 nM and the percentage OSC inhibition against controls was calculated. The more preferred compounds of the present invention exhibit inhibitions larger than 50%. In addition, the test was carried out with different test substance concentrations and subsequently the $IC_{50}$ value was calculated, i.e. the concentration required to reduce the conversion of MOS into lanosterol to 50% of the control value. The preferred compounds of the present invention exhibit $IC_{50}$ values of 1 nM to 10 µM, preferably of 1–100 nM.

The compounds of formula I and their pharmaceutically acceptable acid addition salts can be used as medicaments, e.g. in the form of pharmaceutical preparations for enteral, parenteral or topical administration. They can be administered, for example, perorally, e.g. in the form of tablets, coated tablets, dragees, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula I and their pharmaceutically acceptable acid addition salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragees and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 50 mg to about 500 mg, comes into consideration for the prevention and control of topical and systemic infections by pathogenic fungi. For cholesterol lowering and treatment of impaired glucose tolerance and diabetes the daily dosage conveniently amounts to between 1 and 1000 mg, preferably 5 to 200 mg, for adult patients. Depending on the dosage it is convenient to administer the daily dosage in several dosage units.

The pharmaceutical preparations conveniently contain about 1–500 mg, preferably 5–200 mg, of a compound of formula I.

The following Examples serve to illustrate the present invention in more detail. They are, however, not intended to limit its scope in any manner.

EXAMPLES

Abbreviations:

AcOH=acetic acid, conc.=concentrated, halfconc.=half concentrated, CuI=copper iodide, eq=equivalents, alox= aluminum oxide, DMF=N,N-dimethylformamide, DMSO= dimethyl sulfoxide, ether=diethyl ether, EtOAc=ethyl acetate, EtOH=ethanol, MeOH=methanol, MsCl=methanesulfonyl chloride, $NaBCNH_3$=sodium cyanoborohydride, NMP=N-methylpyrrolidone, Pd/C= palladium on carbon, $Pd(OAc)_2$=palladium diacetate, RT=room temperature, THF=tetrahydrofuran, TFA=trifluoroacetic acid, 18-crown-6=1,4,7,10,13,16-Hexaoxacyclooctadecane.

General Remarks

All reactions were performed under argon.

The purification of the final amines by preparative HPLC [e.g. RP-18, acetonitrile (0.1% HCOOH)/water (0.1% HCOOH), 10% to 95% acetonitrile] yielded mixtures of the corresponding amino formate and the corresponding halogenide or methanesulfonic acid salt which was used in the reaction. The ratio was not always determined, the purity of the final amino salts was >80% after LC-MS.

Example 1

1.1

To 22.3 g (0.1 mol) 5-benzyloxyindole in 110 ml (1.0 mol) 1-bromo-4-fluorobenzene were added 28 g (0.5 mol) powdered potassium hydroxide and 6.4 g (0.1 mol) Cu as powder. The suspension was heated to reflux for 2 h. At RT, ether and water were added, the mixture was acidified with 2M HCl and extracted with ether. The combined organic phases were washed with water and dried over $Na_2SO_4$. Column chromatography on silica gel with a gradient hexane-hexane/EtOAc 19:1–9:1 yielded 19 g (60%) 5-Benzyloxy-1-(4-fluoro-phenyl)-1H-indole as colorless solid, MS: 318 ($MH^+$).

1.2

13.2 g (41.5 mmol) 5-Benzyloxy-1-(4-fluoro-phenyl)-1H-indole in 150 ml ethanol were hydrogenated in the presence of 200 mg 5%Pd/C to yield 6.6 g (70%) 1-(4-Fluoro-phenyl)-1H-indol-5-ol as white solid, MS: 227 (M).

1.3

2.05 g (9 mmol) 1-(4-Fluoro-phenyl)-1H-indol-5-ol in 25 ml acetone were treated with 4.7 ml (30 mmol) 1,6-dibromohexane and 4.14 g (30 mmol) $K_2CO_3$ powder in 25 ml acetone. The mixture was stirred at 55° C. for 6 h, and at RT for 20 h. Acetone was added, and the suspension filtered. Purification of the crude product with column chromatography with hexane/EtOAc 49:1 yielded 2.4 g (68%) 5-(6-Bromo-hexyloxy)-1-(4-fluoro-phenyl)-1H-indole as colorless solid, MS: 389 (M, 1Br, 1Cl).

1.4

195 mg (0.5 mmol) 5-(6-Bromo-hexyloxy)-1-(4-fluoro-phenyl)-1H-indole in 2.5 ml DMF were treated with 185 mg (1 mmol) cyclopropyl-methyl amine·$CF_3CO_2H$ and 96 mg (2 mmol, 50% in mineral oil) NaH at RT for 2 h and at 60° C. for 3 h. At RT, ether and water were added and the inorganic phase was extracted with ether. The combined organic phases were washed with water, dried over $Na_2SO_4$ and evaporated. Purification on silica gel with hexane/ether 1:1 yielded 140 mg (73%) Cyclopropyl-{6-[1-(4-fluoro-phenyl)-1H-indol-5-yloxy]-hexyl}-methyl-amine as light yellow oil, MS: 381 ($MH^+$).

1.5

In analogy to example 1.4, 5-(6-Bromo-hexyloxy)-1-(4-fluoro-phenyl)-1H-indole and piperidine were converted to yield 1-(4-Fluoro-phenyl)-5-(6-piperidin-1-yl-hexyloxy)-1H-indole as light brown amorphous, MS: 395 ($MH^+$).

1.6

To 2.34 g (6 mmol) from 5-(6-Bromo-hexyloxy)-1-(4-fluoro-phenyl)-1H-indole in 5 ml DMF were added 2.9 ml (30 mmol) N-allylmethylamine and the solution was heated to 60° C. for 30 min. After concentration in vacuo, the residue was dissolved in water and ether. 2M NaOH was added, and the inorganic phase was extracted with ether, the combined organic phases were washed with water and dried over $Na_2SO_4$. The residue was dissolved in 150 ml ether and a saturated solution of HCl in ether was added. The solution was concentrated and the residue dissolved in EtOH and toluene, evaporated and triturated from toluene. 1.95 g (86%) Allyl-{6-[1-(4-fluoro-phenyl)-1H-indol-5-yloxy]-butyl}-methyl-amine hydrochloride were isolated as colorless solid, MS: 381 ($MH^+$).

1.7

40 mg (mmol) Allyl-{6-[1-(4-fluoro-phenyl)-1H-indol-5-yoxy]-hexyl}-methyl-amine in 8 ml MeOH were hydrogenated in the presence of 20 mg $PtO_2$, after filtration and evaporation 40 mg (quantitative) {6-[1-(4-Fluoro-phenyl)-1H-indol-5-yloxy]-hexyl}-methyl-propyl-amine were isolated as colorless oil, MS: 383 ($MH^+$).

Example 2

2.1

410 mg (1.8 mmol) 1-(4-Fluoro-phenyl)-1H-indol-5-ol in 6 ml acetone were treated with 500 mg (3.6 mmol) powdered $K_2CO_3$ and 610 µl (3.6 mmol) 1,7-dibromoheptane. The suspension was stirred at 60° C. overnight, cooled to RT, filtered and concentrated. Column chromatography on silica gel with hexane/EtOAc 49:1 yielded 526 mg (72%) 5-(7-Bromo-heptyloxy)-1-(4-fluoro-phenyl)-1H-indole as colorless solid, mp 63–65° C., MS: 403 (M, 1Br).

2.2

101 mg (0.25 mmol) 5-(7-Bromo-heptyloxy)-1-(4-fluoro-phenyl)-1H-indole in 5 ml THF were treated with 0.1 ml (1 mmol) N-allylmethylamine and 71 mg (1 mmol, 50% in mineral oil) at 60° C. overnight. At RT methanol was added, the mixture concentrated and the crude product was purified on silica gel with a gradient hexane-hexane/ether 19:1 yielding 45 mg (46%) Allyl-{7-[1-(4-fluoro-phenyl)-1H-indol-5-yloxy]-heptyl}-methyl-amine as yellow oil, MS: 395 ($MH^+$).

2.3

In analogy to example 2.2, 5-(7-Bromo-heptyloxy)-1-(4-fluoro-phenyl)-1H-indole and piperidine were converted to yield 1-(4-Fluoro-phenyl)-5-(7-piperidin-1-yl-heptyloxy)-1H-indole as colorless gum, MS: 408 ($MH^+$).

Example 3

3.1

To 230 mg (1 mmol) 1-(4-Fluoro-phenyl)-1H-indol-5-ol in 4 ml acetone were added 280 mg (2 mmol) powdered $K_2CO_3$ and 0.24 ml (2 mmol) 1,4-dibromobutane. The suspension was stirred at 55° C. for 5 h, cooled to RT and concentrated. The crude product was extracted with water and ether, the combined organic phases were washed and dried with $Na_2SO_4$. Purification by column chromatography on silica gel with hexane/EtOAc 9:1 yielded 320 mg (88%) 5-(4-Bromo-butoxy)-1-(4-fluoro-phenyl)-1H-indole as light yellow solid, 59–61° C., MS: 361 (M, 1Br).

3.2

In analogy to example 3.1, 1-(4-Fluoro-phenyl)-1H-indol-5-ol and 1,3-dibromopropane were converted to yield 5-(3-Bromo-propoxy)-1-(4-fluoro-phenyl)-1H-indole as colorless solid 61–62° C., MS: 347 (M, 1Br).

3.3

To 160 mg (0.44 mmol) 5-(4-Bromo-butoxy)-1-(4-fluoro-phenyl)-1H-indole in 2 ml DMF were added 0.5 ml (5.2 mmol) N-allylmethylamine and the solution was heated to 60° C. for 30 min. After concentration in vacuo, the residue was dissolved in water and ether. 2M NaOH was added, and the inorganic phase was extracted with ether, the combined organic phases were washed with water and dried over $Na_2SO_4$. Column chromatography on silica gel with $CH_2Cl_2$/MeOH 9:1 yielded 120 mg (77%) Allyl-{4-[1-(4-fluoro-phenyl)-1H-indol-5-yloxy]-butyl}-methyl-amine as yellow oil, MS: 353 ($MH^+$).

3.4

In analogy to example 3.3, 5-(4-Bromo-butoxy)-1-(4-fluoro-phenyl)-1H-indole and methylamine were converted to yield {4-[1-(4-Fluoro-phenyl)-1H-indol-5-yloxy]-butyl}-methyl-amine as colorless crystalline, mp 49–50° C., MS: 313 ($MH^+$).

3.5

In analogy to example 3.1, 1-(4-Fluoro-phenyl)-1H-indol-5-ol and 1,4-dibromobutene were converted to yield 5-(4-Bromo-but-2-enyloxy)-1-(4-fluoro-phenyl)-1H-indole as colorless liquid, MS: 359 (M, 1Br).

3.6

In analogy to example 3.3, 5-(4-Bromo-but-2-enyloxy)-1-(4-fluoro-phenyl)-1H-indole and N-allylmethylamine were converted to yield Allyl-{4-[1-(4-fluoro-phenyl)-1H-indol-5-yloxy]-but-2-enyl}-methyl-amine as colorless viscous oil, MS: 351 ($MH^+$).

3.7

In analogy to example 3.3, 5-(4-Bromo-but-2-enyloxy)-1-(4-fluoro-phenyl)-1H-indole and 2-ethylaminoethanol were converted to yield 2-(Ethyl-{4-[1-(4-fluoro-phenyl)-1H-indol-5-yloxy]-but-2-enyl}-amino)-ethanol as colorless viscous oil, MS: 369 ($MH^+$).

Example 4

4.1

To 6.7 g (30 mmol) 5-benzyloxyindole and 6.6 g (30 mmol) di-tert.-butyldicarbonate in 80 ml DMF were added 3.7 g (33 mmol) potassium tert. butylate at RT and the mixture was stirred at 60° C. for 4 h, cooled to RT and ether /0.5 M HCl were added. The inorganic phase was extracted with ether, the combined organic phases were washed with water and dried over $Na_2SO_4$. Evaporation yielded crude 5-Benzyloxy-indole-1-carboxylic acid tert-butyl ester as colorless oil, MS: 323 (M).

4.2

Hydrogenation of 9.1 g crude 5-Benzyloxy-indole-1-carboxylic acid tert-butyl ester in 200 ml MeOH with 200 mg 10%Pd/C yielded 6.1 g (crude) 5-Hydroxy-indole-1-carboxylic acid tert-butyl ester, MS: 233 (M).

4.3

6.07 g (26 mmol) 5-Hydroxy-indole-1-carboxylic acid tert-butyl ester in 10 ml acetone were treated with 13.8 g (100 mmol) powdered $K_2CO_3$ and 11.8 ml (100 mmol) 1,4-dibromobutane. The suspension was stirred at 100° C. for 3 h, cooled to RT, and acetone was added. The suspension was filtered and concentrated. The residue was redissolved in ether and 0.5 M HCl, the inorganic phase was extracted with ether and the combined organic phases were washed with water, and dried over $Na_2SO_4$. Column chromatography on silica gel with a gradient hexane to hexane/EtOAc 19:1 yielded 7.2 g (65%, 3 steps) 5-(4-Bromo-butoxy)-indole-1-carboxylic acid tert-butyl ester as colorless oil, MS: 367 (M, 1Br).

4.4

4.8 g (13 mmol) 5-(4-Bromo-butoxy)-indole-1-carboxylic acid tert-butyl ester in 5 ml DMF were treated with 5 ml (48.1 mmol) diethylamine at 50° C. for 5 h. The solution was concentrated and extracted with ether and water. The combined organic phases were dried over $Na_2SO_4$ to yield 3.95 g (85%) 5-(4-Diethylamino-butoxy)-indole-1-carboxylic acid tert-butyl ester as yellow oil, MS: 361 ($MH^+$).

4.5

3.9 g (10.8 mmol) 5-(4-Diethylamino-butoxy)-indole-1-carboxylic acid tert-butyl ester in 4 ml EtOH were treated with 0.4 ml halfconc. NaOH at 60° C. for 2 h. The suspension was concentrated in vacuo and the residue dissolved in EtOAc and water. The organic phase was washed with water and dried over $Na_2SO_4$. Evaporation yielded 2.7 g (96%) Diethyl-[4-(1H-indol-5-yloxy)-butyl]-amine as brown oil, MS: 261 ($MH^+$).

4.6

260 mg (1 mmol) Diethyl-[4-(1H-indol-5-yloxy)-butyl]-amine in 2 ml DMSO were treated with 175 mg (1 mmol) 1-bromo-4-fluorobenzene and 26.4 mg (0.1 mmol) 18-crown-6 and 182 mg (1 mmol) KF on alox. The suspension was stirred at 120° C. for 2 h, additional 175 mg (1 mmol) 1-bromo-4-fluorobenzene, 26.4 mg (0.1 mmol) 18-crown-6 and 182 mg (1 mmol) KF on alox were added. The suspension was stirred for 1 h, cooled to RT and diluted with ether and filtered. The solution was washed with 1M NaOH and water, and dried over $Na_2SO_4$. Column chromatography on silica gel with $CH_2Cl_2$/MeOH 4:1 yielded 205 mg (48%) {4-[1-(4-Bromo-phenyl)-1H-indol-5-yloxy]-butyl}-diethyl-amine as light yellow oil, MS: 415 ($MH^+$, 1Br). (analogously to William J. Smith III, J. Scott Sawyer, Tetrahedron Letters 1999, Vol.37, No.3, 299–302.)

4.7

In analogy to example 4.6, Diethyl-[4-(1H-indol-5-yloxy)-butyl]-amine and 1-bromo-2-fluoro-benzene were converted to yield {4-[1-(2-Bromo-phenyl)-1H-indol-5-yloxy]-butyl}-diethyl-amine as light yellow oil, MS: 415 ($MH^+$, 1Br).

4.8

In analogy to example 4.6, Diethyl-[4-(1H-indol-5-yloxy)-butyl]-amine and 1-bromo-3-fluoro-benzene were converted to yield {4-[1-(3-Bromo-phenyl)-1H-indol-5-yloxy]-butyl}-diethyl-amine as light yellow oil, MS: 415 ($MH^+$, 1Br).

4.9

In analogy to example 4.6, Diethyl-[4-(1H-indol-5-yloxy)-butyl]-amine and 2-fluorobiphenyl were converted to yield [4-(1-Biphenyl-2-yl-1H-indol-5-yloxy)-butyl]-diethyl-amine as light yellow oil, MS: 412 (M).

4.10

130 mg (0.5 mmol) Diethyl-[4-(1H-indol-5-yloxy)-butyl]-amine in 1 ml DMF were treated with 67 mg (0.6 mmol) potassium tert. butylate and 150 mg (0.6 mmol) 4-bromobenzylbromide at 45° C. for 1 h. Ether and water were added and the organic phase was washed with water and dried over $Na_2SO_4$. Column chromatography on silica gel with $CH_2Cl_2$: MeOH 9:1 yielded 115 mg (53%) {4-[1-(4-Bromo-benzyl)-1H-indol-5-yloxy]-butyl}-diethyl-amine as colorless oil, MS: 429 ($MH^+$, 1Br).

Example 5

5.1

2.27 g (10 mmol) 1-(4-Fluoro-phenyl)-1H-indol-5-ol in 5 ml pyridine were treated with 1.85 ml (11 mmol) trifluoromethanesulfonic acid anhydride at 0° C. The solution was stirred at RT over night, diluted with ether and water, the organic phase was washed with 2M HCl and water, and dried over $Na_2SO_4$. Purification by column chromatography with hexane yielded 2.7 g (75%) Trifluoro-methanesulfonic acid 1-(4-fluoro-phenyl)-1H-indol-5-yl ester as white solid, MS: 359 (M).

5.2

To 2.25 g (6.25 mmol) Trifluoro-methanesulfonic acid 1-(4-fluoro-phenyl)-1H-indol-5-yl ester in 12.5 ml piperidine were added 360 mg (0.31 mmol) tetrakis (triphenylphosphine)-palladium followed by 60.0 mg (0.31 mmol) copper iodide. The solution was evaporated and flushed with argon prior to the addition of 450 μl (4.95 mmol) 4-pentynol at 80° C. over a period of 45 min. Further 0.45 ml (4.95 mmol) 4-pentynol were added and the solution was stirred for 2 h. The mixture was added to ice water, acidified with 2M HCl and extracted with ether. The combined organic phases were washed with water and dried over $Na_2SO_4$. Purification by column chromatography with $CH_2Cl_2$/MeOH 19:1 yielded 1.4 g (76%) 5-[1-(4-Fluoro-phenyl)-1H-indol-5-yl]-pent-4-yn-1-ol as light yellow waxy solid, MS: 293 (M).

5.3

In analogy to example 5.2, Trifluoro-methanesulfonic acid 1-(4-fluoro-phenyl)-1H-indol -5-yl ester and propargylalcohol were converted to yield 3-[1-(4-Fluoro-phenyl)-1H-indol -5-yl]-prop-2-yn-1-ol as light brown solid, 85–88° C., MS: 265 (M).

5.4

440 mg (1.5 mmol) 5-[1-(4-Fluoro-phenyl)-1H-indol-5-yl]-pent-4-yn-1-ol in 15 ml $CH_2Cl_2$ were treated with 0.15 ml (1.8 mmol) methane sulfonyl chloride and 0.63 ml (4.5 mmol) triethyl amine at 0° C. for 10 min. The solution was stirred at RT for 2 h and was diluted with $CH_2Cl_2$. The organic phase was extracted with 1M HCl and water, and dried over $Na_2SO_4$. Evaporation yielded 400 mg (71%) Methanesulfonic acid 5-[1-(4-fluoro-phenyl)-1H-indol-5-yl]-pent-4-ynyl ester as light yellow viscous oil, MS: 372 ($MH^+$).

5.5

100 mg (0.26 mmol) Methanesulfonic acid 5-[1-(4-fluoro-phenyl)-1H-indol-5-yl]-pent-4-ynyl ester and 0.5 ml (5.2 mmol) N-allylmethylamine were stirred in 1 ml DMF at 60° C. for 1.5 h. The solution was concentrated, and the residue was dissolved in water and $CH_2Cl_2$. 2M NaOH was added and the inorganic phase was extracted with $CH_2Cl_2$. The combined organic phases were washed with water and dried over $Na_2SO_4$. Column chromatography with $CH_2Cl_2$/MeOH 19:1 yielded 50 mg (55%) Allyl-{5-[1-(4-fluoro-phenyl)-1H-indol-5-yl]-pent-4-ynyl}-methyl-amine as light yellow oil, MS: 347 ($MH^+$).

5.6

In analogy to example 5.5, Methanesulfonic acid 5-[1-(4-fluoro-phenyl)-1H-indol-5-yl]-pent-4-ynyl ester and ethylamionoethanol were converted to yield 2-(Ethyl-{5-[1-(4-fluoro-phenyl)-1H-indol-5-yl]-pent-4-ynyl}-amino)-ethanol as yellow viscous oil, MS: 365 ($MH^+$).

Example 6

6.1

400 mg (1.4 mmol) 5-[1-(4-Fluoro-phenyl)-1H-indol-5-yl]-pent-4-yn-1-ol in 10 ml EtOH were hydrogenated in the presence of 25 Mg $PtO_2$. The suspension was filtered and the crude material purified by column chromatography on silica gel with hexane/EtOAc to yield 330 mg (79%) 5-[1-(4-Fluoro-phenyl)-1H-indol-5-yl]-pentan-1-ol as colorless viscous oil, MS: 297 (M).

6.2

800 mg (3 mmol) 3-[1-(4-Fluoro-phenyl)-1H-indol-5-yl]-prop-2-yn-1-ol in 25 ml MeOH were hydrogenated in the presence of 100 mg $PtO_2$, filtered and evaporated to yield 710 mg crude 3-[1-(4-Fluoro-phenyl)-1H-indol-5-yl]-propan-1-ol as colorless gum, MS: 270 ($MH^+$).

6.3

300 mg (1 mmol) 5-[1-(4-Fluoro-phenyl)-1H-indol-5-yl]-pentan-1-ol in 10 ml $CH_2Cl_2$ were treated with 0.1 ml (1.2 mmol) methane sulfonyl chloride and 0.41 ml (3 mmol) triethyl amine at 0° C. The solution was stirred at RT for 2 h, was diluted with $CH_2Cl_2$ and extracted with 1M HCl and water, and dried over $Na_2SO_4$. Evaporation yielded 310 mg (83%) Methanesulfonic acid 5-[1-(4-fluoro-phenyl)-1H-indol-5-yl]-pentyl ester as light brown oil, MS: 376 ($MH^+$).

6.4

130 mg (0.26 mmol) Methanesulfonic acid 5-[1-(4-fluoro-phenyl)-1H-indol-5-yl]-pentyl ester and 0.5 ml (5.2 mmol) N-allylmethylamine in 0.5 ml DMF were stirred at 60° C. for 2 h. The solution was concentrated and dissolved in water and $CH_2Cl_2$. 2M NaOH was added and the inorganic phase was extracted with $CH_2Cl_2$. The combined organic phases were washed with water and dried over $Na_2SO_4$. Column chromatography with $CH_2Cl_2$/MeOH 19:1 yielded 90 mg (98%) Allyl-{5-[1-(4-fluoro-phenyl)-1H-indol-5-yl]-pentyl}-methyl-amine as orange oil, MS: 351 ($MH^+$).

6.5

In analogyto example 6.4, Methanesulfonic acid 5-[1-(4-fluoro-phenyl)-1H-indol-5-yl]-pentyl ester and ethylamionoethanol were converted to yield 2-(Ethyl-{5-[1-(4-fluoro-phenyl)-1H-indol-5-yl]-pentyl}-amino)-ethanol as yellow viscous oil, MS: 369 ($MH^+$).

6.6

675 mg (2.5 mmol) crude 3-[1-(4-Fluoro-phenyl)-1H-indol-5-yl]-propan-1-ol in 20 ml $CH_2Cl_2$ were treated with 0.24 ml (3.0 mmol) methanesulfonyl chloride and 1.05 ml (7.5 mmol) triethyl amine at 0° C. The solution was stirred at RT for 1 h, was diluted with $CH_2Cl_2$ and extracted with 1M HCl and water, and dried over $Na_2SO_4$. 750 mg (86%) Methanesulfonic acid 3-[1-(4-fluoro-phenyl)-1H-indol-5-yl]-propyl ester as brown oil, MS: 347 (M).

6.7

150 mg (0.43 mmol) Methanesulfonic acid 3-[1-(4-fluoro-phenyl)-1H-indol-5-yl]-propyl ester and 0.5 ml N-allylmethylamine in 1 ml DMF were stirred at 60° C. for 1 h. The solution was concentrated and dissolved in water, ether and 0.5M NaOH was added. The inorganic phase was extracted with ether and the combined organic phases were washed with water and dried over $Na_2SO_4$. Column chromatography with $CH_2Cl_2$/MeOH 19:1 yielded 105 mg (76%) Allyl-{3-[1-(4-fluoro-phenyl)-1H-indol-5-yl]-propyl}-methyl-amine as light brown oil, MS: 323 ($MH^+$).

Example 7

7.1

To 5.9 g (30 mmol) 5-bromoindole in 100 ml DMF were added 4.48 g (40 mmol) potassium tert. butylate followed by 8.72 g (40 mmol) di-tert.-dibutylcarbonate at RT. The reaction mixture was warmed to 40° C. for 15 min and to 60° C. for 1 h, cooled to RT and was diluted with ether and water. The solution was acidified with 2M HCl and extracted with ether. The combined organic phases were dried over $Na_2SO_4$ and the crude product was purified by flash chromatography yielding 6.6 g (74%) 5-Bromo-indole-1-carboxylic acid tert-butyl ester as colorless crystals.

7.2

To 3.73 g (12.5 mmol) 5-Bromo-indole-1-carboxylic acid tert-butyl ester in 25 ml piperidine were added 722 mg (0.63 mmol) tetrakis-(triphenylphosphine)-palladium and 120 mg (0.625 mmol) CuI. The solution was purged with argon, and was heated to 80° C. over a period of 45 min, during which 0.9 ml (9.4 mmol) 4-pentynol were added. Additional 0.9 ml (9.4 mmol) 4-pentynol were added and the mixture was stirred at 80° C. for 2 h, poured on ice water and 2M HCl was added. The inorganic phase was extracted with ether, the organic phases were washed with water and dried over $Na_2SO_4$. Purification on silica gel yielded 2.9 g (77%) 5-(5-Hydroxy-pent-1-ynyl)-indole-1-carboxylic acid tert-butyl ester as brown oil, MS: 299 (M).

7.3

2.85 g (9.5 mmol) 5-(5-Hydroxy-pent-1-ynyl)-indole-1-carboxylic acid tert-butyl ester in 100 ml MeOH were subjected to hydrogenation with 300 mg 10%Pd/C to yield 2.8 g 5-(5-Hydroxy-pentyl)-indole-1-carboxylic acid tert-butyl ester as colorless oil, MS: 303 (M). To the crude material in 60 ml $CH_2Cl_2$, 0.87 ml (11 mmol) methanesulfonyl chloride and 3.8 ml (27 mmol) triethyl amine were added at 0° C. The solution was stirred at RT for 1 h.

The reaction mixture was diluted with 60 ml $CH_2Cl_2$ and extracted with 0.5M HCl, water and dried over $Na_2SO_4$. 3.1 g crude 5-(5-Methanesulfonyloxy-pentyl)-indole-1-carboxylic acid tert-butyl ester were obtained as dark red oil, MS: 382 ($MH^+$).

7.4

1.5 g (0.4 mmol) crude 5-(5-Methanesulfonyloxy-pentyl)-indole-1-carboxylic acid tert-butyl ester in 3 ml DMF were treated with 1.15 ml (12 mmol) N-allylmethylamine at 60° C. for 1 h. The solution was concentrated in vacuo and, the residue was dissolved in water and ether, 0.5M NaOH was added and the inorganic phase was extacted with ether. The combined organic phases were washed with water and dried over $Na_2SO_4$. Column chromatography on silica gel yielded 1.35 g (94%) 5-[5-(Allyl-methyl-amino)-pentyl]-indole-1-carboxylic acid tert-butyl ester as light yellow oil, MS: 357 ($MH^+$).

7.5

To 1.3 g (3.5 mmol) 5-[5-(Allyl-methyl-amino)-pentyl]-indole-1-carboxylic acid tert-butyl ester in 20 ml ethanol were added 1.5 ml water and 3 ml conc. NaOH, and stirred at 60° C. for 1.5 h. The slurry was concentrated and dissolved in ether/water. The organic layer was washed with water and dried over $Na_2SO_4$ and evaporated to yield 900 mg (quantitative) Allyl-[5-(1H-indol-5-yl)-pentyl]-methyl-amine as light yellow oil, MS: 257 ($MH^+$).

7.6

In analogy to example 4.6, Allyl-[5-(1H-indol-5-yl)-pentyl]-methyl-amine and 1-bromo-2-fluoro-benzene were converted to yield Allyl-{5-[1-(2-bromo-phenyl)-1H-indol-5-yl]-pentyl}-methyl-amine as yellow oil, MS: 411 ($MH^+$, 1Br).

7.7

In analogy to example 4.6, Allyl-[5-(1H-indol-5-yl)-pentyl]-methyl-amine and 1-bromo-3-fluoro-benzene were converted to yield Allyl-{5-[1-(3-bromo-phenyl)-1H-indol-5-yl]-pentyl}-methyl-amine as light brown oil, MS: 411 ($MH^+$, 1Br).

7.8

In analogy to example 4.6, Allyl-[5-(1H-indol-5-yl)-pentyl]-methyl-amine and 2-fluoro-biphenyl were converted to yield Allyl-[5-(1-biphenyl-2-yl-1H-indol-5-yl)-pentyl]-methyl-amine as light yellow oil, MS: 409 ($MH^+$).

7.9

In analogy to example 4.6, Allyl-[5-(1H-indol-5-yl)-pentyl]-methyl-amine and 1-fluoro-4-trifluoromethyl-benzene were converted to yield Allyl-methyl-{5-[1-(4-trifluoromethyl-phenyl)-1H-indol-5-yl]-pentyl}-amine as light brown oil, MS: 401 ($MH^+$).

Example 8

8.1

In analogy to example 4.6, 5-benzyloxy-indole and 1-bromo-4-fluoro-benzene were converted to yield 5-Benzyloxy-1-(4-bromo-phenyl)-1H-indole as light brown solid, mp 118° C., MS: 377 (M, 1Br).

8.2

3.8 g (10 mmol) 5-Benzyloxy-1-(4-bromo-phenyl)-1H-indole in 30 ml EtOAc and 10 ml EtOH were hydrogenated in the presence of 5% Pd/C. Column chromatography on silica gel in hexane/EtOAc 5:1 yielded 1.3 g (62%) 1-Phenyl-1H-indol-5-ol as colorless viscous oil, MS: 209 (M).

8.3

864 mg (4.1 mmol) 1-Phenyl-1H-indol-5-ol in 10 ml acetone were treated with 2.44 g (10 mmol) 1,6-dibromohexane and 2.8 g (20 mmol) $K_2CO_3$ at reflux for 4 h. The solution was filtered, concentrated and purified by column chromatography on silica gel with hexane/EtOAc 39:1 to yield 800 mg (52%) 5-(6-Bromo-hexyloxy)-1-phenyl-1H-indole as colorless oil, MS: 371 (M, 1Br).

8.4

In analogy to example 4.4, 5-(6-Bromo-hexyloxy)-1-phenyl-1H-indole and N-allylmethylamine were converted to yield Allyl-methyl-[6-(1-phenyl-1H-indol-5-yloxy)-hexyl]-amine as light yellow oil, MS: 363 ($MH^+$).

8.5

In analogy to example 4.4, 5-(6-Bromo-hexyloxy)-1-phenyl-1H-indole and diethylamine were converted to yield Diethyl-[6-(1-phenyl-1H-indol-5-yloxy)-hexyl]-amine as colorless oil, MS: 365 ($MH^+$).

8.6

In analogy to example 4.4, 5-(6-Bromo-hexyloxy)-1-phenyl-1H-indole and 2-(ethylamino)ethanol were converted to yield 2-{Ethyl-[6-(1-phenyl-1H-indol-5-yloxy)-hexyl]-amino}-ethanol as colorless oil, MS: 381($MH^+$).

Example 9

9.1

To 14.7 g (0.1 mol) 5-methoxyindole in 100 ml DMSO were added 32.6 ml (0.3 mol) 1-bromo-4-fluorobenzene, 1.06 g (0.04 mol) 18-crown-6 and 10.92 g (60 mmol) KF on alox. The suspension was heated to 120° C. for 48 h. Additional 21.7 ml (0.2 mol) 1-bromo-4-fluorobenzene, 1.06 g (0.04 mol) 18-crown-6 and 10.92 g (60 mmol) KF on alox were added, and the mixture was stirred at 130° C. for 20 h. At RT, ether and water were added, the phases were separated and the inorganic phase was extracted with ether. The combined organic phases were washed with water and dried over $Na_2SO_4$. The residue was triturated in ethanol to yield 25.5 g (84%) 1-(4-Bromo-phenyl)-5-methoxy-1H-indole as light brown solid, mp 90–91° C., MS: 301 (M, 1Br).

9.2

To 140 ml (140 mmol) 1M L-selectride in THF (Lithium-tri-sec-butylborohydride), 14.9 g (50 mmol) 1-(4-Bromo-phenyl)-5-methoxy-1H-indole were added slowly in small portions at RT. The mixture was stirred at 75° C. for 60 h, concentrated and dissolved in ether and water. The organic phase was washed with water and dried over $Na_2SO_4$. Trituration with cyclohexane yielded 13.9 g (96%) 1-(4-Bromo-phenyl)-1H-indol-5-ol as grey solid, MS: 287 ($MH^+$).

9.3

In analogy to example 3.1, 1-(4-Bromo-phenyl)-1H-indol-5-ol and 1,4-dibrombutane were converted to yield 5-(4-Bromo-butoxy)-1-(4-bromo-phenyl)-1H-indole as light yellow solid, mp 80–81° C., MS: 421 (M, 2Br).

9.4

In analogy to example 5.1, 1-(4-Bromo-phenyl)-1H-indol-5-ol was treated with trifluoromethanesulfonic acid anhydride to yield Trifluoro-methanesulfonic acid 1-(4-bromo-phenyl)-1H-indol-5-yl ester as colorless viscous oil, MS: 420 (M).

9.5

To 8.4 g (20 mmol) Trifluoro-methanesulfonic acid 1-(4-bromo-phenyl)-1H-indol-5-yl ester in 30 ml piperidine were added 2.08 g (24 mmol) LiBr, 580 mg (0.05 eq) [1,2-Bis (diphenylphosphino)ethane]dichloropalladium(II) and 2.8 ml (30 mmol) 4-pentyn-1-ol. The mixture was stirred at 60° C. for 3 h, further 0.5 ml (5.4 mmol) 4-pentynol were added and stirred at 70° C. for 1 h. The reaction mixture was concentrated and dissolved in ether and water. 2M HCl was added and the inorganic phase was extracted with ether. The combined organic phases were washed with water and concentrated. The residue was dissolved in 50 ml EtOH and treated with 5 ml conc. NaOH at 50° C. for 30 min. The solution was concentrated and dissolved in water and ether. The organic phase was washed with water, dried over $Na_2SO_4$ and concentrated. Column chromatography with $CH_2Cl_2$ yielded 2.15 g (30%) 5-[1-(4-Bromo-phenyl)-1H-indol-5-yl]-pent-4-yn-1-ol as colorless viscous oil, MS: 353 (M, 1Br).

9.6

In analogy to example 5.4, 5-[1-(4-Bromo-phenyl)-1H-indol-5-yl]-pent-4-yn-1-ol and methanesulfonyl chloride were converted to yield Methanesulfonic acid 5-[1-(4-bromo-phenyl)-1H-indol-5-yl]-pent-4-ynyl ester as light yellow viscous oil, MS: 431 (M, 1Br).

9.7

432 mg (1 mmol) Methanesulfonic acid 5-[1-(4-bromo-phenyl)-1H-indol-5-yl]-pent-4-ynyl ester in 30 ml EtOAc/EtOH/hexane (1:1:1) was hydrogenated in the presence of 20 mg $PtO_2$, the solution was filtered and evaporated. Column chromatography on silica gel with hexane/EtOAc 4:1 yielded (95%) Methanesulfonic acid 5-[1-(4-bromo-phenyl)-1H-indol-5-yl]-pentyl ester as colorless viscous oil, MS: 435 (M, 1Br).

Example 10

10.1

To 4.2 g (10 mmol) Trifluoro-methanesulfonic acid 1-(4-bromo-phenyl)-1H-indol-5-yl ester in 30 ml piperidine, 580 mg (0.5 mmol) tetrakis-(triphenylphosphine)-palladium and 100 mg (0.625 mmol) CuI were added. The solution was evaporated and purged with argon three times, before 1.4 ml (10 mmol) ethynyltrimethylsilane were added. The solution was stirred at RT for 48 h. Additional 0.38 ml (3.3 mmol) ethynyltrimethylsilane were added and the mixture was stirred at 50° C. for 1 h. The solution was concentrated and the residue redissolved in 0.5M HCl and ether. The inorganic phase was extracted with ether, the organic phases were washed with water and dried over $Na_2SO_4$. Purification on silica gel with hexane/EtOAc 19:1 yielded 1.7 g (38%) Trifluoro-methanesulfonic acid 1-(4-trimethylsilanylethynyl-phenyl)-1H-indol-5-yl ester as orange oil, MS: 437 (M).

10.2

To 1.62 g (3.7 mmol) Trifluoro-methanesulfonic acid 1-(4-trimethylsilanylethynyl-phenyl)-1H-indol-5-yl ester in 5 ml piperidine, 230 mg (0.2 mmol) tetrakis-(triphenylphosphine)-palladium and 40 mg (0.2 mmol) CuI were added. The solution was evaporated and purged with argon three times, before 0.56 ml (6 mmol) 4-pentyn-1-ol were added. The solution was stirred at 80° C. for 2 h. The solution was concentrated and the residue dissolved in 0.5M HCl and ether. The inorganic phase was extracted with ether, the organic phases were washed with water and dried over $Na_2SO_4$. Purification on silica gel with $CH_2Cl_2$ yielded 980 mg (71%) 5-[1-(4-Trimethylsilanylethynyl-phenyl)-1H-indol-5-yl]-pent-4-yn-1-ol as orange viscous oil, MS: 371 (M).

10.3

970 mg (2.6 mmol) 5-[1-(4-Trimethylsilanylethynyl-phenyl)-1H-indol-5-yl]-pent-4-yn-1-ol in 10 ml MeOH were treated with 41.4 mg (3 mmol) $K_2CO_3$. The solution was concentrated, the residue dissolved in ether and 0.5M HCl and the organic phase was washed with water and dried over $Na_2SO_4$. Column chromatography on silica gel with ether yielded 680 mg (87%) 5-[1-(4-Ethynyl-phenyl)-1H-indol-5-yl]-pent-4-yn-1-ol as orange oil, MS: 299 (M).

10.4

In analogy to example 5.4, 5-[1-(4-Ethynyl-phenyl)-1H-indol-5-yl]-pent-4-yn-1-ol and methanesulfonyl chloride were converted to yield Methanesulfonic acid 5-[1-(4-ethynyl-phenyl)-1H-indol-5-yl]-pent-4-ynyl ester as orange oil, MS: 377 (M).

10.5

In analogy to example 5.5, Methanesulfonic acid 5-[1-(4-ethynyl-phenyl)-1H -indol-5-yl]-pent-4-ynyl ester and 2-ethylaminoethanol were converted to yield 2-(Ethyl-{5-[1-(4-ethynyl-phenyl)-1H-indol-5-yl]-pent-4-ynyl}-amino)-ethanol as light yellow viscous oil, MS: 371 (MH$^+$).

10.6

In analogy to example 5.5, Methanesulfonic acid 5-[1-(4-ethynyl-phenyl)-1H-indol-5-yl]-pent-4-ynyl ester and diethylamine were converted to yield Diethyl-{5-[1-(4-ethynyl-phenyl)-1H-indol-5-yl]-pent-4-ynyl}-amine as yellow oil, MS: 355 (MH$^+$).

10.7

In analogy to example 5.5, Methanesulfonic acid 5-[1-(4-ethynyl-phenyl)-1H-indol-5-yl]-pent-4-ynyl ester and methyl-aminoethanol were converted to yield 2-({5-[1-(4-Ethynyl-phenyl)-1H-indol-5-yl]-pent-4-ynyl}-methyl-amino)-ethanol as yellow oil, MS: 357 (MH$^+$).

10.8

60 mg (0.16 mmol) 2-(Ethyl-{5-[1-(4-ethynyl-phenyl)-1H-indol-5-yl]-pent-4-ynyl}-amino)-ethanol in 10 ml MeOH were hydrogenated in the presence of 20 mg Pd/C, filtered and concentrated. Purification by column chromatography on silica gel with $CH_2Cl_2$/MeOH 9:1 yielded 8.0 mg 2-(Ethyl-{5-[1-(4-ethyl-phenyl)-1H-indol-5-yl]-pentyl}-amino)-ethanol as colorless oil, MS: 379 (MH$^+$).

10.9

In analogy to example 10.8, Diethyl-{5-[1-(4-ethynyl-phenyl)-1H-indol-5-yl]-pent-4-ynyl}-amine was converted to yield Diethyl-{5-[1-(4-ethyl-phenyl)-1H-indol-5-yl]-pentyl}-amine as colorless oil, MS: 363 (MH$^+$).

10.10

In analogy to example 10.8 ($PtO_2$ was used instead of Pd/C), 2-({5-[1-(4-Ethynyl-phenyl)-1H-indol-5-yl]-pent-4-ynyl}-methyl-amino)-ethanol was converted to yield 2-({5-[1-(4-Ethyl-phenyl)-1H-indol-5-yl]-pentyl}-methyl-amino)-ethanol as colorless oil, MS: 365 (MH$^+$).

Example 11

11.1

3.17 g (10 mmol) 5-Benzyloxy-1-(4-fluoro-phenyl)-1H-indole in 25 ml acetic acid was hydrogenated in the presence of 300 mg 10%Pd/C, filtered and hydrogenated with 60 mg $PtO_2$ for 3 h. The catalyst was removed by filtration and the solution concentrated. The residue was dissolved in 15 ml trifluoroacetic acid and treated with 1.9 g (30 mml) sodium cyanoborhydride at 0° C. The solution was stirred at RT for 30 min, concentrated and dissolved in ether, 0.5M NaOH. The inorganic phase was extracted with ether, the combined organic phases were washed with brine and dried over $Na_2SO_4$. Column chromatography on silica gel with $CH_2Cl_2$/MeOH 19:1 yielded 1.0 g (44%) 1-(4-Fluoro-phenyl)-2,3-dihydro-1H-indol-5-ol as colorless solid; MS: 229 (M).

11.2

460 mg (2 mmol) 1-(4-Fluoro-phenyl)-2,3-dihydro-1H-indol-5-ol in 6 ml acetone were treated with 830 mg (6 mmol) powdered K$_2$CO$_3$ and 1 ml (6 mmol) 1,6-dibromohexane. The suspension was stirred at 60° C. for 6 h, cooled to RT, diluted with acetone, filtered and concentrated. Column chromatography on silica gel with a gradient hexane to hexane/EtOAc 19:1 yielded 210 mg (25%) (6-Bromo-hexyloxy)-1-(4-fluoro-phenyl)-2,3-dihydro-1H-indole as yellow oil, MS: 392(MH$^+$, 1Br).

11.3

90 mg (0.22 mmol) (6-Bromo-hexyloxy)-1-(4-fluoro-phenyl)-2,3-dihydro-1H-indole in 0.5 ml DMF were treated with 0.5 ml (5.2 mmol) N-allylmethylamine at 80° C. for 1 h. The mixture was concentrated in vacuo, dissolved in 0.5 M NaOH and CH$_2$Cl$_2$. The inorganic phase was extracted with CH$_2$Cl$_2$ and the combined organic phases were washed with brine, dried over Na$_2$SO$_4$. Purification on silica gel with CH$_2$Cl$_2$/MeOH 19:1 yielded 75 mg (96%) Allyl-{6-[1-(4-fluoro-phenyl)-2,3-dihydro-1H-indol-5-yloxy]-hexyl}-methyl-amine as yellow oil, MS: 383(MH$^+$).

11.4

In analogy to example 11.3, (6-Bromo-hexyloxy)-1-(4-fluoro-phenyl)-2,3-dihydro-1H-indole and ethylaminoethanol were converted to yield 2-(Ethyl-{6-[1-(4-fluoro-phenyl)-2,3-dihydro-1H-indol-5-yloxy]-hexyl}-amino)-ethanol as orange viscous oil, MS: 401(MH$^+$).

11.5

104 mg (0.25 mmol) {4-[1-(4-Bromo-phenyl)-1H-indol-5-yloxy]-butyl}-diethyl-amine in 1 ml TFA were treated with 32 mg (0.5 mmol) NaCNBH$_3$ at 0° C. for 5 min and 30 min at RT. Ether and water were added, followed by 2M NaOH. The inorganic phase was extracted with ether, the combined organic phases were washed with water and dried over Na$_2$SO$_4$. Column chromatography on silica gel with CH$_2$Cl$_2$/MeOH 19:1-1%sat.NH$_3$ in MeOH yielded 40 mg (38%) {4-[1-(4-Bromo-phenyl)-2,3-dihydro-1H-indol-5-yloxy]-butyl}-diethyl-amine as light yellow waxy solid, MS: 417 (MH$^+$, 1Br).

Example 12

12.1

This example was carried out in analogy to: Gordon W. Gribble, Joseph H. Hoffmann Synthesis 1977, 859–860. To a precooled solution of 22.3 g (0.1 mol) 5-benzyloxyindole in 270 ml acetic acid, 19 g (0.3 mol) NaCNBH$_3$ were added. The solution was stirred at RT for 2 h, the volume was reduced to a third and poured into 300 ml water. Potassium hydroxide was added under cooling, and the solution was extracted with ether. The combined organic phases were washed with water, dried over Na$_2$SO$_4$ and evaporated to yield 20.1 g (89%) 5-Benzyloxy-2,3-dihydro-1H-indole as colorless oil, MS: 225 (M).

12.2

20 g (89 mmol) 5-Benzyloxy-2,3-dihydro-1H-indole in 250 ml CH$_2$Cl$_2$ were treated with 20 g (91.6 mmol) di-tert.-butyldicarbonate at 0° C. for 1 h and at RT for 1 h. The mixture was concentrated and extracted with ether and 0.5 M HCl. The organic phase was washed with water, and dried over Na$_2$SO$_4$. Trituration of the crude material with hexane yielded 23 g (71%) 5-Benzyloxy-2,3-dihydro-indole-1-carboxylic acid tert-butyl ester as colorless solid, MS: 325 (M).

12.3

23 g (68.6 mmol) 5-Benzyloxy-2,3-dihydro-indole-1-carboxylic acid tert-butyl ester in 250 ml methanol with 2.5 g 10% Pd/C were hydrogenated for 2 h, the suspension was filtered. The filtrate was concentrated and purified by column chromatography on silica gel with MeOH/EtOAc 1:1, yielding 14.4 g (90%) 5-Hydroxy-2,3-dihydro-indole-1-carboxylic acid tert-butyl ester as colorless solid, MS: 235 (M).

12.4

9.41 g (40 mmol) 5-Hydroxy-2,3-dihydro-indole-1-carboxylic acid tert-butyl ester in 90 ml acetone were treated with 16.6 g (6 mmol) powdered K$_2$CO$_3$ and 17.3 g (5 mmol) 1,4-dibromobutane. The suspension was stirred at 50° C. for 4 h, cooled to RT, filtered and concentrated. Column chromatography on silica gel with CH$_2$Cl$_2$ yielded 8.8 g (60%) 5-(4-Bromo-butoxy)-2,3-dihydro-indole-1-carboxylic acid tert-butyl ester as colorless solid.

12.5

8.8 g (24 mmol) 5-(4-Bromo-butoxy)-2,3-dihydro-indole-1-carboxylic acid tert-butyl ester in 10 ml DMF were treated with 7.11 g (100 mmol) N-allylmethylamine at 50° C. for 4 h. The solution was concentrated in vacuo, and the residue was redissolved in ether and water. 2M NaOH was added and the inorganic phase was extracted with ether. The combined organic phases were washed with water, dried over Na$_2$SO$_4$ and evaporated. Column chromatography with a gradient of CH$_2$Cl$_2$/MeOH 19:1 to 9:1 yielded 7.4 g (85%) 5-[4-(Allyl-methyl-amino)-butoxy]-2,3-dihydro-indole-1-carboxylic acid tert-butyl ester as colorless oil, MS: 361 (MH$^+$).

12.6

To 7.3 g (20.2) 5-[4-(Allyl-methyl-amino)-butoxy]-2,3-dihydro-indole-1-carboxylic acid tert-butyl ester in 15 ml CH$_2$Cl$_2$, 10 ml trifluoro acetic acid were added at 0° C. The mixture was stirred at reflux for 3 h and was concentrated in vacuo. Water and 2M NaOH were added and the inorganic phase was extracted with ether. The combined organic phases were washed with water and dried over Na$_2$SO$_4$. Evaporation yielded 5.2 g (98%) Allyl-[4-(2,3-dihydro-1H-indol-5-yloxy)-butyl]-methyl-amine as orange oil, MS: 261 (MH$^+$)

12.7

260 mg (1 mmol) Allyl-[4-(2,3-dihydro-1H-indol-5-yloxy)-butyl]-methyl-amine in 2.5 ml DMSO were treated with 280 mg (2 mmol) powdered K$_2$CO$_3$ and 480 mg (2 mmol) 1-chloro-4-iodobenzene at 130° C. for 1 h. 19.1 mg (0.1 mmol) CuI were added and the mixture was stirred for additional 2 h at 130° C. At RT, water and ether were added, and the organic phase was washed with water, dried over Na$_2$SO$_4$. Column chromatography on silica gel with CH$_2$Cl$_2$/MeOH 19:1 yielded 75 mg (20%) Allyl-{4-[1-(4-chloro-phenyl)-1H-indol-5-yloxy]-butyl}-methyl-amine as orange oil, MS: 369 (MH$^+$, 1Cl).

Example 13

13.1

4 g (20 mmol) 5-bromo-indoline in 50 ml CH$_2$Cl$_2$ were treated with 4.4 g (20 mmol) di.-tert.-butyldicarbonate at RT over night. The reaction mixture was concentrated in vacuo and triturated with hexane to yield 5.3 g (89%) 5-Bromo-2,3-dihydro-indole-1-carboxylic acid tert-butyl ester as colorless solid, MS: 297 (M, 1Br).

13.2

To 3.73 g (12.5 mmol) 5-Bromo-2,3-dihydro-indole-1-carboxylic acid tert-butyl ester in 25 ml piperidine were added 722 mg (0.63 mmol) tetrakis-(triphenylphosphine)-palladium and 120 mg (0.625 mmol) CuI. The solution was purged with argon, and was heated to 80° C. over a period of 45 min, during which 0.9 ml (9.4 mmol) 4-pentyn-1-ol were added. Additional 0.9 ml (9.4 mmol) 4-pentyn-1-ol were added and the mixture was stirred for 2 h, poured on ice water and 2M HCl was added. The inorganic phase was extracted with ether, the combined organic phases were washed with water and dried over Na$_2$SO$_4$. Purification on silica gel with hexane/EtOAc 4:1 to 2:1 yielded 3.0 g (79%) 5-(5-Hydroxy-pent-1-ynyl)-2,3-dihydro-indole-1- carboxylic acid tert-butyl ester as light brown solid, MS: 302 (MH$^+$). (See also: Stara, Irena G.; Stary, Ivo; Kollarovic, Adrian; Teply, Filip; Saman, David; Fiedler, Pavel. Coupling reactions of halobenzenes with alkynes. The synthesis of phenylacetylenes and symmetrical or unsymmetrical 1,2-diphenylacetylenes. Collect. Czech. Chem. Commun. (1999), 64(4), 649–672)

13.3

2.8 g (9.3 mmol) 5-(5-Hydroxy-pent-1-ynyl)-2,3-dihydro-indole-1-carboxylic acid tert-butyl ester in 60 ml MeOH were subjected to hydrogenation with 10%Pd/C to yield 2.8 g (quantitative) 5-(5-Hydroxy-pentyl)-2,3-dihydro-indole-1-carboxylic acid tert-butyl ester as colorless viscous oil, MS: 305 (M).

13.4

To 2.75 g (9 mmol) 5-(5-Hydroxy-pentyl)-2,3-dihydro-indole-1-carboxylic acid tert-butyl ester in 100 ml CH$_2$Cl$_2$, 0.87 ml (11 mmol) methanesulfonyl chloride and 3.8 ml (27 mmol) triethyl amine were added at 0° C. The solution was concentrated in vacuo to yield crude 5-(5-Methanesulfonyloxy-pentyl)-2,3-dihydro-indole-1-carboxylic acid tert-butyl ester as yellow viscous oil, MS: 384 (MH$^+$). The crude material was dissolved in 5 ml DMF and 5 ml (50 mmol) N-allylmethylamine. The mixture was heated to 80° C. for 3 h, concentrated and the residue was dissolved in water and ether, 2N NaOH was added and the inorganic phase was extacted with ether. The combined organic phases were washed with water and dried over Na$_2$SO$_4$. Column chromatography on silica gel with CH$_2$Cl2/MeOH 9:1 yielded 2.5 g (72%) 5-[5-(Allyl-methyl-amino)-pentyl]-2,3-dihydro-indole -1-carboxylic acid tert-butyl ester as colorless liquid, MS: 359 (MH$^+$).

13.5

2.45 g (6.8 mmol) 5-[5-(Allyl-methyl-amino)-pentyl]-2,3-dihydro-indole-1-carboxylic acid tert-butyl ester in 5 ml CH$_2$Cl$_2$ were treated with 4 ml TFA at 0° C. The solution was stirred at RT for 0.5 h, and at 40° C. for 1 h. The solution was concentrated, and the residue was dissolved in ether, water. 2M NaOH was added and the inorganic phase was extracted with ether. The combined organic phases were washed with water and dried over Na$_2$SO$_4$ to yield 1.65 g (94%) Allyl-[5-(2,3-dihydro-1H-indol-5-yl)-pentyl]-methyl-amine as light yellow oil, MS: 259 (MH$^+$).

13.6

In analogy to example 12.7, Allyl-[5-(2,3-dihydro-1H-indol-5-yl)-pentyl]-methyl-amine and 1-chloro-4-iodobenzene were converted to yield Allyl-{5-[1-(4-chloro-phenyl)-1H-indol-5-yl]-pentyl}-methyl-amine as light brown semisolid, MS: 367(MH$^+$, 1Cl).

Example 14

To a solution of 1 equivalent of the corresponding bromide in (2–4 ml/mmol bromide) dry DMA, a solution of 2 equivalents of the corresponding secondary amine in (1–5 ml/mmol amine) dry DMA was added at RT. After 16 h, 2 additional equivalents of of the secondary amine were added. The mixture was kept at RT over night, formic acid was added and the mixture was purified by preparative HPLC [RP-18, acetonitrile (0.1% HCOOH)/water (0.1% HCOOH), 10% to 95% acetonitrile]. After evaporation, the resulting compound was obtained as a mixture of amino formate and hydrobromide.

| No. | Compound | MS MH$^+$ | Bromide | Secondary amine |
|---|---|---|---|---|
| 14.1 | Allyl-{3-[1-(4-fluoro-phenyl)-1H-indol-5-yloxy]-propyl}-methyl-amine | 339 | 5-(3-Bromo-propoxy)-1-(4-fluoro-phenyl)-1H-indole | N-Methylallyl-amine |
| 14.2 | 2-(Ethyl-{3-[1-(4-fluoro-phenyl)-1H-indol-5-yloxy]-propyl}-amino)-ethanol | 357 | 5-(3-Bromo-propoxy)-1-(4-fluoro-phenyl)-1H-indole | 2-Ethylamino-ethanol |
| 14.3 | Diethyl-{3-[1-(4-fluoro-phenyl)-1H-indol-5-yloxy]-propyl}-amine | 341 | 5-(3-Bromo-propoxy)-1-(4-fluoro-phenyl)-1H-indole | Diethylamine |
| 14.4 | {3-[1-(4-Fluoro-phenyl)-1H-indol-5-yloxy]-propyl}-dimethyl-amine | 313 | 5-(3-Bromo-propoxy)-1-(4-fluoro-phenyl)-1H-indole | Dimethylamine |
| 14.5 | {3-[1-(4-Fluoro-phenyl)-1H-indol-5-yloxy]-propyl}-(2-methoxy-ethyl)-methyl-amine | 357 | 5-(3-Bromo-propoxy)-1-(4-fluoro-phenyl)-1H-indole | N-(2-Methoxy-ethyl)methylamine |
| 14.6 | 2-({3-[1-(4-Fluoro-phenyl)-1H-indol-5-yloxy]-propyl}-methyl-amino)-ethanol | 343 | 5-(3-Bromo-propoxy)-1-(4-fluoro-phenyl)-1H-indole | N-Methyl-2-amino-ethanol |
| 14.7 | 2-[{3-[1-(4-Fluoro-phenyl)-1H-indol-5-yloxy]-propyl}-(2-hydroxy-ethyl)-amino]-ethanol | 373 | 5-(3-Bromo-propoxy)-1-(4-fluoro-phenyl)-1H-indole | Diethanolamine |
| 14.8 | Cyclopropylmethyl-{3-[1-(4-fluoro-phenyl)-1H-indol-5-yloxy]-propyl}-methyl-amine | 353 | 5-(3-Bromo-propoxy)-1-(4-fluoro-phenyl)-1H-indole | N-Methyl-cyclopropylmethyl-amine |
| 14.9 | 1-(4-Fluoro-phenyl)-5-(3-pyrrolidin-1-yl-propoxy)-1H-indole | 339 | 5-(3-Bromo-propoxy)-1-(4-fluoro-phenyl)-1H-indole | Pyrrolindine |
| 14.10 | 1-(4-Fluoro-phenyl)-5-(3-morpholin-4-yl-propoxy)-1H-indole | 355 | 5-(3-Bromo-propoxy)-1-(4-fluoro-phenyl)-1H-indole | Morpholine |
| 14.11 | Ethyl-{3-[1-(4-fluoro-phenyl)-1H-indol-5-yloxy]- | 371 | 5-(3-Bromo-propoxy)-1-(4-fluoro-phenyl)- | N-(2-Methoxy-ethyl)-ethylamine |

-continued

| No. | Compound | MS MH+ | Bromide | Secondary amine |
|---|---|---|---|---|
| | propyl}-(2-methoxy-ethyl)-amine | | 1H-indole | |
| 14.12 | 1-{3-[1-(4-Fluoro-phenyl)-1H-indol-5-yloxy]-propyl}-piperidin-4-ol | 369 | 5-(3-Bromo-propoxy)-1-(4-fluoro-phenyl)-1H-indole | 4-Hydroxy-piperidine |
| 14.13 | 5-[3-(3,6-Dihydro-2H-pyridin-1-yl)-propoxy]-1-(4-fluoro-phenyl)-1H-indole | 351 | 5-(3-Bromo-propoxy)-1-(4-fluoro-phenyl)-1H-indole | 1,2,5,6-Tetrahydro-pydridine |
| 14.14 | {3-[1-(4-Fluoro-phenyl)-1H-indol-5-yloxy]-propyl}-methyl-propyl-amine | 341 | 5-(3-Bromo-propoxy)-1-(4-fluoro-phenyl)-1H-indole | N-Methylpropyl-amine |
| 14.15 | {3-[1-(4-Fluoro-phenyl)-1H-indol-5-yloxy]-propyl}-methyl-prop-2-ynyl-amine | 337 | 5-(3-Bromo-propoxy)-1-(4-fluoro-phenyl)-1H-indole | N-Methyl-propargylamine |
| 14.16 | 1-(4-Fluoro-phenyl)-5-(3-piperidin-1-yl-propoxy)-1H-indole | 353 | 5-(3-Bromo-propoxy)-1-(4-fluoro-phenyl)-1H-indole | Piperidine |
| 14.17 | 5-(3-Azetidin-1-yl-propoxy)-1-(4-fluoro-phenyl)-1H-indole | 325 | 5-(3-Bromo-propoxy)-1-(4-fluoro-phenyl)-1H-indole | Azetidine |
| 14.18 | 2-(Ethyl-{4-[1-(4-fluoro-phenyl)-1H-indol-5-yloxy]-butyl}-amino)-ethanol | 371 | 5-(4-Bromo-butoxy)-1-(4-fluoro-phenyl)-1H-indole | 2-Ethylamino-ethanol |
| 14.19 | Diethyl-{4-[1-(4-fluoro-phenyl)-1H-indol-5-yloxy]-butyl}-amine | 355 | 5-(4-Bromo-butoxy)-1-(4-fluoro-phenyl)-1H-indole | Diethylamine |
| 14.20 | {4-[1-(4-Fluoro-phenyl)-1H-indol-5-yloxy]-butyl}-dimethyl-amine | 327 | 5-(4-Bromo-butoxy)-1-(4-fluoro-phenyl)-1H-indole | Dimethylamine |
| 14.21 | {4-[1-(4-Fluoro-phenyl)-1H-indol-5-yloxy]-butyl}-(2-methoxy-ethyl)-methyl-amine | 371 | 5-(4-Bromo-butoxy)-1-(4-fluoro-phenyl)-1H-indole | N-(2-Methoxy-ethyl)-methyl-amine |
| 14.22 | 2-({4-[1-(4-Fluoro-phenyl)-1H-indol-5-yloxy]-butyl}-methyl-amino)-ethanol | 357 | 5-(4-Bromo-butoxy)-1-(4-fluoro-phenyl)-1H-indole | N-Methyl-2-aminoethanol |
| 14.23 | 2-[{4-[1-(4-Fluoro-phenyl)-1H-indol-5-yloxy]-butyl}-(2-hydroxy-ethyl)-amino]-ethanol | 387 | 5-(4-Bromo-butoxy)-1-(4-fluoro-phenyl)-1H-indole | Diethanolamine |
| 14.24 | Cyclopropylmethyl-{4-[1-(4-fluoro-phenyl)-1H-indol-5-yloxy]-butyl}-methyl-amine | 367 | 5-(4-Bromo-butoxy)-1-(4-fluoro-phenyl)-1H-indole | N-Methyl-cyclopropyl-methyl-amine |
| 14.25 | 1-(4-Fluoro-phenyl)-5-(4-pyrrolidin-1-yl-butoxy)-1H-indole | 353 | 5-(4-Bromo-butoxy)-1-(4-fluoro-phenyl)-1H-indole | Pyrrolindine |
| 14.26 | 1-(4-Fluoro-phenyl)-5-(4-morpholin-4-yl-butoxy)-1H-indole | 369 | 5-(4-Bromo-butoxy)-1-(4-fluoro-phenyl)-1H-indole | Morpholine |
| 14.27 | Ethyl-{4-[1-(4-fluoro-phenyl)-1H-indol-5-yloxy]-butyl}-(2-methoxy-ethyl)-amine | 385 | 5-(4-Bromo-butoxy)-1-(4-fluoro-phenyl)-1H-indole | N-(2-Methoxy-ethyl)-ethylamine |
| 14.28 | 1-{4-[1-(4-Fluoro-phenyl)-1H-indol-5-yloxy]-butyl}-piperidin-4-ol | 383 | 5-(4-Bromo-butoxy)-1-(4-fluoro-phenyl)-1H-indole | 4-Hydroxy-piperidine |
| 14.29 | 5-[4-(3,6-Dihydro-2H-pyridin-1-yl)-butoxyl]-1-(4-fluoro-phenyl)-1H-indole | 365 | 5-(4-Bromo-butoxy)-1-(4-fluoro-phenyl)-1H-indole | 1,2,5,6-Tetrahydro-pydridine |
| 14.30 | {4-[1-(4-Fluoro-phenyl)-1H-indol-5-yloxy]-butyl}-methyl-propyl-amine | 355 | 5-(4-Bromo-butoxy)-1-(4-fluoro-phenyl)-1H-indole | N-Methylpropyl-amine |

-continued

| No. | Compound | MS MH+ | Bromide | Secondary amine |
|---|---|---|---|---|
| 14.31 | {4-[1-(4-Fluoro-phenyl)-1H-indol-5-yloxy]-butyl}-methyl-prop-2-ynyl-amine | 351 | 5-(4-Bromo-butoxy)-1-(4-fluoro-phenyl)-1H-indole | N-Methyl-propargyl-amine |
| 14.32 | 1-(4-Fluoro-phenyl)-5-(4-piperidin-1-yl-butoxy)-1H-indole | 367 | 5-(4-Bromo-butoxy)-1-(4-fluoro-phenyl)-1H-indole | Piperidine |
| 14.33 | 5-(4-Azetidin-1-yl-butoxy)-1-(4-fluoro-phenyl)-1H-indole | 339 | 5-(4-Bromo-butoxy)-1-(4-fluoro-phenyl)-1H-indole | Azetidine |
| 14.34 | Allyl-{4-[1-(4-bromo-phenyl)-1H-indol-5-yloxy]-butyl}-methyl-amine | 413 (1 Br) | 5-(4-Bromo-butoxy)-1-(4-bromo-phenyl)-1H-indole | N-Methylallyl-amine |
| 14.35 | {4-[1-(4-Bromo-phenyl)-1H-indol-5-yloxy]-butyl}-methyl-propyl-amine | 415 (1 Br) | 5-(4-Bromo-butoxy)-1-(4-bromo-phenyl)-1H-indole | N-Methylpropyl-amine |
| 14.36 | 2-[{4-[1-(4-Bromo-phenyl)-1H-indol-5-yloxy]-butyl}-(2-hydroxy-ethyl)-amino]-ethanol | 447 (1 Br) | 5-(4-Bromo-butoxy)-1-(4-bromo-phenyl)-1H-indole | Diethanolamine |
| 14.37 | 2-({4-[1-(4-Bromo-phenyl)-1H-indol-5-yloxy]-butyl}-ethyl-amino)-ethanol | 431 (1 Br) | 5-(4-Bromo-butoxy)-1-(4-bromo-phenyl)-1H-indole | 2-Ethylamino-ethanol |
| 14.38 | {4-[1-(4-Bromo-phenyl)-1H-indol-5-yloxy]-butyl}-ethyl-(2-methoxy-ethyl)-amine | 445 (1 Br) | 5-(4-Bromo-butoxy)-1-(4-bromo-phenyl)-1H-indole | N-(2-Methoxy-ethyl)-ethylamine |
| 14.39 | 5-(4-Azetidin-1-yl-butoxy)-1-(4-bromo-phenyl)-1H-indole | 399 (1 Br) | 5-(4-Bromo-butoxy)-1-(4-bromo-phenyl)-1H-indole | Azetidine |

Example 15

To a solution of 6 equivalents of the corresponding primary amine in (0.5–3 ml/mmol amine) dry DMF, 1 equivalent of the corresponding bromide in (1–3 ml/mmol bromide) dry DMF, as well as 1 equivalent of 1,8-Diazabicyclo[5.4.0]undec-7-ene(1,5–5) were added. The mixture was shaken over night at 50° C. Formic acid was added and the mixture was purified by preparative HPLC [RP-18, acetonitrile (0.1% HCOOH)/water (0.1% HCOOH), 10% to 95% acetonitrile]. After evaporation, the resulting compound was obtained as a mixture of amino formate and hydrobromide.

Example 16

To a solution of 1 equivalent of the corresponding Methanesulfonic acid ester in (2–4 ml/mmol) dry DMA, a solution of 3 equivalents of the corresponding secondary amine in (0.1–0.2 ml/mmol) dry DMA and 1 equivalent of NaI were added at RT. The mixture was heated at 40° C. for 12 h. Formic acid was added and the mixture was purified by preparative HPLC [RP-18, acetonitrile (0.1% HCOOH)/water (0.1% HCOOH), 10% to 95% acetonitrile]. After evaporation, the resulting compound was obtained as a mixture of amino formate and methanesulfonic acid salt.

| No. | Compound | MS MH+ | Bromide | Primary amine |
|---|---|---|---|---|
| 15.1 | Allyl-{3-[1-(4-fluoro-phenyl)-1H-indol-5-yloxy]-propyl}-amine | 325 | 5-(3-Bromo-propoxy)-1-(4-fluoro-phenyl)-1H-indole | Allylamine |
| 15.2 | Ethyl-{3-[1-(4-fluoro-phenyl)-1H-indol-5-yloxy]-propyl}-amine | 313 | 5-(3-Bromo-propoxy)-1-(4-fluoro-phenyl)-1H-indole | Ethylamine |
| 15.3 | 2-{3-[1-(4-Fluoro-phenyl)-1H-indol-5-yloxy]-propylamino}-ethanol | 329 | 5-(3-Bromo-propoxy)-1-(4-fluoro-phenyl)-1H-indole | Aminoethanol |
| 15.4 | Allyl-{4-[1-(4-fluoro-phenyl)-1H-indol-5-yloxy]-butyl}-amine | 339 | 5-(4-Bromo-butoxy)-1-(4-fluoro-pheny)-1H-indole | Allylamine |
| 15.5 | Ethyl-{4-[1-(4-fluoro-phenyl)-1H-indol-5-yloxy]-butyl}-amine | 327 | 5-(4-Bromo-butoxy)-1-(4-fluoro-phenyl)-1H-indole | Ethylamine |
| 15.6 | 2-{4-[1-(4-Fluoro-phenyl)-1H-indol-5-yloxy]-butylamino}-ethanol | 343 | 5-(4-Bromo-butoxy)-1-(4-fluoro-phenyl)-1H-indole | Aminoethanol |

| No. | Compound | MS MH+ | Methanesulfonic acid ester | Secondary amine |
|---|---|---|---|---|
| 16.1 | {5-[1-(4-Bromo-phenyl)-1H-indol-5-yl]-pent-4-ynyl}-methyl-propyl-amine | 409 | Methanesulfonic acid 5-[1-(4-bromo-phenyl)-1H-indol-5-yl]-pent-4-ynyl ester | N-Methylpropyl-amine |
| 16.2 | 2-({5-[1-(4-Bromo-phenyl)-1H-indol-5-yl]-pent-4-ynyl}-ethyl-amino)-ethanol | 425 | Methanesulfonic acid 5-[1-(4-bromo-phenyl)-1H-indol-5-yl]-pent-4-ynyl ester | 2-Ethylamino-ethanol |
| 16.3 | {5-[1-(4-Bromo-phenyl)-1H-indol-5-yl]-pent-4-ynyl}-dimethyl-amine | 381 | Methanesulfonic acid 5-[1-(4-bromo-phenyl)-1H-indol-5-yl]-pent-4-ynyl ester | Dimethylamine |
| 16.4 | 2-({5-[1-(4-Bromo-phenyl)-1H-indol-5-yl]-pent-4-ynyl}-methyl-amino)-ethanol | 411 | Methanesulfonic acid 5-[1-(4-bromo-phenyl)-1H-indol-5-yl]-pent-4-ynyl ester | Methylamino-ethanol |
| 16.5 | {5-[1-(4-Bromo-phenyl)-1H-indol-5-yl]-pent-4-ynyl}-(2-methoxy-ethyl)-methyl-amine | 425 | Methanesulfonic acid 5-[1-(4-bromo-phenyl)-1H-indol-5-yl]-pent-4-ynyl ester | N-(2-Methoxy-ethyl)methylamine |
| 16.6 | {5-[1-(4-Bromo-phenyl)-1H-indol-5-yl]-pent-4-ynyl}-diethyl-amine | 409 | Methanesulfonic acid 5-[1-(4-bromo-phenyl)-1H-indol-5-yl]-pent-4-ynyl ester | Diethylamine |
| 16.7 | {5-[1-(4-Bromo-phenyl)-1H-indol-5-yl]-pentyl}-methyl-propyl-amine | 413 | Methanesulfonic acid 5-[1-(4-bromo-phenyl)-1H-indol-5-yl]-pentyl ester | N-Methylpropyl-amine |
| 16.8 | 2-({5-[1-(4-Bromo-phenyl)-1H-indol-5-yl]-pentyl}-ethyl-amino)-ethanol | 429 | Methanesulfonic acid 5-[1-(4-bromo-phenyl)-1H-indol-5-yl]-pentyl ester | 2-Ethylamino-ethanol |
| 16.9 | {5-[1-(4-Bromo-phenyl)-1H-indol-5-yl]-pentyl}-dimethyl-amine | 385 | Methanesulfonic acid 5-[1-(4-bromo-phenyl)-1H-indol-5-yl]-pentyl ester | Dimethylamine |
| 16.10 | 2-({5-[1-(4-Bromo-phenyl)-1H-indol-5-yl]-pentyl}-methyl-amino)-ethanol | 415 | Methanesulfonic acid 5-[1-(4-bromo-phenyl)-1H-indol-5-yl]-pentyl ester | Methylamino-ethanol |
| 16.11 | {5-[1-(4-Bromo-phenyl)-1H-indol-5-yl]-pentyl}-(2-methoxy-ethyl)-methyl-amine | 429 | Methanesulfonic acid 5-[1-(4-bromo-phenyl)-1H-indol-5-yl]-pentyl ester | N-(2-Methoxy-ethyl)methylamine |
| 16.12 | {5-[1-(4-Bromo-phenyl)-1H-indol-5-yl]-pentyl}-diethyl-amine | 413 | Methanesulfonic acid 5-[1-(4-bromo-phenyl)-1H-indol-5-yl]-pentyl ester | Diethylamine |

Example 17

17.1

To 4.2 g (20 mmol) 5-Bromo-3-methyl-1H-indole [prepared according to Noland, Wayland E.; Reich, Charles. Synthesis and reactions of 5-bromoskatole and 5-bromo-1,3-dimethylindole. J. Org. Chem. (1967), 32(3), 828–32.] in 22 ml (0.2 mol) 1-bromo-4-fluorobenzene were added 5.6 g (0.1 mol) powdered potassium hydroxide and 1.14 g (60 mmol) CuI as powder. The suspension was heated to reflux for 0.5 h. At RT, ether and water were added, the phases were separated and the aqueous phase was extracted with ether. The combined organic phases were washed with water and dried over $Na_2SO_4$. Column chromatography on silica gel with hexane yielded 750 mg 5-Bromo-1-(4-fluoro-phenyl)-3-methyl-1H-indole as colorless solid, mp 97–98° C., MS: 303(M, 1Br).

17.2

4 ml (43.2 mmol) 4-pentyn-1-ol in 140 ml $CH_2Cl_2$ were treated with 3.7 ml (47.6 mmol) methanesulfonyl chloride and 11.1 ml (64.84 mmol) N,N-diisopropylethylamine at 0° C. for 10 min. The solution was stirred at RT for 1 h and was diluted with $CH_2Cl_2$. Water was added, the mixture was stirred for 10 min and was added to a 10% aqueous $KHSO_4$ solution. The phases were separated and the aqueous phase was extracted with $CH_2Cl_2$. The combined organic ones were washed with a saturated aqueous solution of $NaHCO_3$ and brine, dried over $Na_2SO_4$ and evaporated to give crude Methanesulfonic acid pent-4-ynyl ester as yellow oil, MS: 156 (MH+).

The oil was dissolved in 50 ml DMA and was treated with 15.5 ml (159.05 mmol) 2-ethylaminoethanol at 60° C. for 5 h and at 80° C. for 1.5 h. Stirring was continued at RT over night, the solution was concentrated, and the residue was dissolved in ether/1M NaOH. The phases were separated and the organic one was washed with 1M NaOH and brine, and dried over $Na_2SO_4$. Evaporation yielded 5.6 g (68%, 2steps) 2-(Ethyl-pent-4-ynyl-amino)-ethanol as yellow oil, MS: 155 (M).

17.3

To 200 mg (0.66 mmol) 5-Bromo-1-(4-fluoro-phenyl)-3-methyl-1H-indole in 2 ml piperidine were added 36 mg (0.03 mmol) tetrakis(triphenylphosphine)-palladium followed by 12 mg (0.06 mmol) copper iodide. The solution was evaporated and flushed with argon prior to the addition of 100 μl 2-(Ethyl-pent-4-ynyl-amino)-ethanol at 80° C. Additional 100 μl 2-(Ethyl-pent-4-ynyl-amino)-ethanol were added after 2 h and the suspension was stirred for 2 h. The mixture was added to ice water, and extracted with ether. The combined organic phases were washed with water and dried over $Na_2SO_4$. Purification by column chromatography with $CH_2Cl_2$/MeOH 9:1 yielded 152 mg (61%) 2-(Ethyl-{5-[1-(4-fluoro-phenyl)-3-methyl-1H-indol-5-yl]-pent-4-ynyl}-amino)-ethanol as orange viscous oil, MS: 379 (MH$^+$).

17.4

In analogy to example 6.2, 2-(Ethyl-{5-[1-(4-fluoro-phenyl)-3-methyl-1H-indol-5-yl]-pent-4-ynyl}-amino)-ethanol was hydrogenated to yield 2-(Ethyl-{5-[1-(4-fluoro-phenyl)-3-methyl-1H-indol-5-yl]-pentyl}-amino)-ethanol as colorless oil, MS: 383 (MH$^+$).

Example 18

18.1

In analogy to example 7.1, 5-Bromo-1-(4-fluoro-phenyl)-3-methyl-1H-indole was converted to yield 5-Bromo-3-methyl-indole-1-carboxylic acid tert-butyl ester as light yellow solid, mp 92° C., MS: 309 (M, 1Br).

18.2

In analogy to example 7.2, 5-Bromo-3-methyl-indole-1-carboxylic acid tert-butyl ester and 4-pentynol were converted to yield 5-(5-Hydroxy-pent-1-ynyl)-3-methyl-indole-1-carboxylic acid tert-butyl ester as brown gum, MS: 313 (M).

18.3

In analogy to example 5.4, 5-(5-Hydroxy-pent-1-ynyl)-3-methyl-indole-1-carboxylic acid tert-butyl ester and methanesulfonyl chloride were converted to yield 5-(5-Methanesulfonyloxy-pent-1-ynyl)-3-methyl-indole-1-carboxylic acid tert-butyl ester as yellow viscous oil, MS: 392 (MH$^+$).

18.4

In analogy to example 5.5, 5-(5-Methanesulfonyloxy-pent-1-ynyl)-3-methyl-indole-1-carboxylic acid tert-butyl ester and methylallylamine were converted to yield 5-[5-(Allyl-methyl-amino)-pent-1-ynyl]-3-methyl-indole-1-carboxylic acid tert-butyl ester as light yellow oil, MS: 367 (MH$^+$).

18.5

In analogy to example 4.5, 5-[5-(Allyl-methyl-amino)-pent-1-ynyl]-3-methyl-indole-1-carboxylic acid tert-butyl ester was was converted to yield Allyl-methyl-[5-(3-methyl-1H-indol-5-yl)-pent-4-ynyl]-amine as orange viscous oil, MS: 267 (MH$^+$).

18.6

In analogy to example 9.1, Allyl-methyl-[5-(3-methyl-1H-indol-5-yl)-pent-4-ynyl]-amine and 1-bromo-4-fluorbenzene were converted to yield Allyl-{5-[1-(4-bromo-phenyl)-3-methyl-1H-indol-5-yl]-pent-4-ynyl}-methyl-amine as light yellow viscous oil, MS: 421 (MH$^+$, 1Br).

18.7

In analogy to example 17.1, Allyl-methyl-[5-(3-methyl-1H-indol-5-yl)-pent-4-ynyl]-amine and 1-Iodo-4-trifluoromethyl-benzene were converted to yield Allyl-methyl-{5-[3-methyl-1-(4-trifluoromethyl-phenyl)-1H-indol-5-yl]-pent-4-ynyl}-amine as yellow oil, MS: 411 (MH$^+$).

Example 19

19.1

In analogy to example 3.1, 5-hydroxy-2-methylindole and 1,4-dibrombutane were converted to yield 5-(4-Bromo-butoxy)-2-methyl-1H-indole as colorless solid, mp 85° C., MS: 281 (M, 1Br).

19.2

In analogy to example 3.3, 5-(4-Bromo-butoxy)-2-methyl-1H-indole and N-methylallylamine were converted to yield Allyl-methyl-[4-(2-methyl-1H-indol-5-yloxy)-butyl]-amine as yellow viscous oil, MS: 273 (MH$^+$).

19.3

In analogy to example 9.1, Allyl-methyl-[4-(2-methyl-1H-indol-5-yloxy)-butyl]-amine and 1-bromo-4-fluorbenzene were converted to yield Allyl-{4-[1-(4-bromo-phenyl)-2-methyl-1H-indol-5-yloxy]-butyl}-methyl-amine as orange viscous oil, MS: 426 (M, 1Br).

19.4

In analogy to example 9.1, Allyl-methyl-[4-(2-methyl-1H-indol-5-yloxy)-butyl]-amine and 1-Fluoro-4-trifluoromethyl-benzene were converted to yield Allyl-methyl-{4-[2-methyl-1-(4-trifluoromethyl-phenyl)-1H-indol-5-yloxy]-butyl}-amine as yellow viscous oil, MS: 417 (MH$^+$).

19.5

In analogy to example 12.1, Allyl-methyl-{4-[2-methyl-1-(4-trifluoromethyl-phenyl)-1H-indol-5-yloxy]-butyl}-amine was converted to yield Allyl-methyl-{4-[2-methyl-1-(4-trifluoromethyl-phenyl)-2,3-dihydro-1H-indol-5-yloxy]-butyl}-amine as yellow oil, MS: 419 (MH$^+$).

Example 20

20.1

In analogy to example 3.1, 2,3-Dimethyl-1H-indol-5-ol [for preparation see for example: Roth, H. J.; Lepke, P. Synthesis of indole and carbazole derivatives by condensation of α-hydroxyketones and aromatic amines. Arch. Pharm. (Weinheim) (1972), 305(3), 159–71.] and 1,4-dibromobutane were converted to yield 5-(4-Bromo-butoxy)-2,3-dimethyl-1H-indole as white solid, mp 119–120° C., MS: 295 (M, 1Br).

20.2

In analogy to example 3.3, 5-(4-Bromo-butoxy)-2,3-dimethyl-1H-indole and N-methylallylamine were converted to yield Allyl-[4-(2,3-dimethyl-1H-indol-5-yloxy)-butyl]-methyl-amine as light brown oil, MS: 287 (MH$^+$).

20.3

In analogy to example 9.1, Allyl-[4-(2,3-dimethyl-1H-indol-5-yloxy)-butyl]-methyl-amine and 1-Fluoro-4-trifluoromethyl-benzene were converted to yield Allyl-{4-[2,3-dimethyl -1-(4-trifluoromethyl-phenyl)-1H-indol-5-yloxy]-butyl}-methyl-amine as yellow oil, MS: 431 (MH$^+$).

20.4

In analogy to example 9.1, Allyl-[4-(2,3-dimethyl-1H-indol-5-yloxy)-butyl]-methyl-amine and 1-fluoro-4-bromobenzene were converted to yield Allyl-{4-[1-(4-bromo-phenyl)-2,3-dimethyl-1H-indol-5-yloxy]-butyl}-methyl-amine as orange oil, MS: 441 (MH$^+$,1 Br).

Example 21

21.1

In anaolgy to Geri, Roberto; Polizzi, Carmela; Lardicci, Luciano; Caporusso, Anna Maria; Gazz.Chim.Ital.; 124; 6; 1994; 241–248: To 14.3 ml (146.3 mmol) 2-Ethylaminoethanol in 60 ml THF were added 362 mg (3.7 mmol) CuCl, followed by 7.5 g (73.1 mmol) 3-Chloro-3-methyl-1-butyne. The solution was stirred at RT for 2 h, the solvent was removed and the residue dissolved in ether/2M HCl. The phases were separated and after addition of $Na_2CO_3$ to the aqueous phase (pH9), it was extracted with ether. The ether phase was dried over $Na_2SO_4$ and concentrated. Destillation by Kugelrohr yielded 2-[(1,1-Dimethyl-prop-2-ynyl)-ethyl-amino]-ethanol as colorless oil, MS: 155 (M).

21.2

In analogy to example 21.1, 3-Chloro-3-methyl-1-butyne and Methylaminoethanol gave 2-[(1,1-Dimethyl-prop-2-ynyl)-methyl-amino]-ethanol as colorless oil, MS: 141 (M).

21.3

In analogy to example 21.1, 3-Chloro-3-methyl-1-butyne and piperidine gave 1-(1,1-Dimethyl-prop -2-ynyl)-piperidine 30153B121 as colorless solid mp 54–56, MS: 151(M).

21.4

In analogy to example 21.1, 3-Chloro-3-methyl-1-butyne and 2-Ethylaminoethanol gave 2-(Ethyl-prop-2-ynyl-amino)-ethanol 30153B146 as colorless oil, MS: 127 (M).

Example 22

22.1

In analogy to example 17.3, Trifluoro-methanesulfonic acid 1-(4-fluoro-phenyl)-1H-indol-5-yl ester and 2-[(1,1-Dimethyl-prop -2-ynyl)-ethyl-amino]-ethanol were converted to Yield 2-(Ethyl-{3-[1-(4-fluoro-phenyl)-1H-indol-5-yl]-1,1-dimethyl-prop-2-ynyl}-amino)-ethanol as orange viscous oil, MS: 365 (MH$^+$).

22.2

In analogy to example 17.3, Trifluoro-methanesulfonic acid 1-(4-fluoro-phenyl)-1H-indol-5-yl ester and 2-[(1,1-Dimethyl-prop-2-ynyl)-methyl-amino]-ethanol were converted to yield 1-(4-Fluoro-phenyl)-5-(3-methyl-3-piperidin-1yl-but-1-ynyl)-1H-indole as light brown viscous oil, MS: 361 (MH$^+$).

22.3

In analogy to example 17.3, Trifluoro-methanesulfonic acid 1-(4-fluoro-phenyl)-1H-indol-5-yl ester and 2-[(1,1-Dimethyl-prop-2-ynyl)-methyl-amino]-ethanol were converted to yield 2-({3-[1-(4-Fluoro-phenyl)-1H-indol-5-yl]-1,1-dimethyl-prop-2-ynyl}-methyl-amino)-ethanol as orange viscous oil, MS: 351 (MH$^+$).

22.4

In analogy to example 17.3, Trifluoro-methanesulfonic acid 1-(4-fluoro-phenyl)-1H-indol-5-yl ester and 2-(Ethyl-prop-2-ynyl-amino)-ethanol were converted to yield 2-(Ethyl-{3-[1-(4-fluoro-phenyl)-1H-indol-5-yl]-prop-2-ynyl}-amino)-ethanol as brown viscous oil, MS: 337 (MH$^+$).

Example 23

23.1

To 33.3 g (0.3 mol) 3-fluoroaniline in 160 ml CH$_2$Cl$_2$ were added 450 ml of a 0.7 M aqueous NaHCO$_3$-solution. The resulting mixture was treated dropwise with 34.6 ml (0.41 mol) methylchloroformate within a period of 20 min. After stirring overnight the layers were separated and the organic layer was washed with saturated aqueous NaCl and dried with MgSO$_4$. After evaporation of ca.60% of the solvent, 600 ml of hexane were added, whereby (3-Fluoro-phenyl)-carbamic acid methyl ester precipitated as a colorless solid that was filtered off and dried i.v (41 g (81%)). The solid was dissolved in 600 ml acetonitrile and treated subsequently with 50 g (0.28 mmol) N-bromosuccinimide and 2.13 ml (0.024 mol) trifluormethane sulfonic acid. After stirring at room temperature during 12 hours ca 50% of the solvent were evaporated, the resulting mixture diluted with 1000 ml EtOAc, and washed subsequently with saturated aqueous NaHCO$_3$ and saturated aqueous NaCl. Drying of the combined organic layers with MgSO$_4$, evaporation of the solvent, and column chromatography on silica gel with hexane/EtOAc 8:1 and then 2:1 gave 39 g (64%) (4-Bromo-3-fluoro-phenyl)-carbamic acid methyl ester as a colorless solid, that was dissolved in 390 ml acetonitrile, treated subsequently with 39 g (0.172 mol) N-iodosuccinimide and 1.4 ml (0.016 mol) trifluormethanesulfonic acid at 0° C. and left to stirr at room temperature during 10 hours. Cooling the reaction mixture to 0° C. led to precipitation of (4-Bromo-5-fluoro-2-iodo-phenyl)-carbamic acid methyl ester as colorless crystals that were filtered off and dried (26.7g, 44%). Dilution of the filtrate with 600 ml hexane followed by subsequent washing with saturated aqueous NaHCO$_3$ and 0.5M aqueous NaS$_2$O$_3$, drying of the organic layer with MgSO$_4$, evaporation of the solvent, and recrystallization of the residue in acetonitrile gave an additional 6.3 g (12%) of (4-Bromo-5-fluoro-2-iodo-phenyl)-carbamic acid methyl ester (total: 33 g, 56%), MS: 373 (M, 1Br).

23.2

A mixture of 70 mg (0.1 mmol) Pd(PPh$_3$)$_2$Cl$_2$ and 27 mg (0.142 mmol) CuI in triethylamine was refluxed under argon during 20 min, cooled to 0° C., treated with 7 g (0.019 mmol) (4-Bromo-5-fluoro-2-iodo-phenyl)-carbamic acid methyl ester, stirred 10 min. at room temperature, treated with 2.95 (0.021 mmol) ethinyltrimethylsilane, and stirred 1 h at room temperature. 2M aqueous HCl and ice were added and the mixture extracted three times with EtOAc. The combined organic layers were washed subsequently with H$_2$O and saturated aqueous NaCl, dried with MgSO$_4$ and the solvent was evaporated. The crude product obtained was dissolved in 50 ml tert.-butanol, treated with 3.2 g (0.023 mol) KOH and the resulting mixture refluxed during 1.5 h. The solvent was evaporated and the residue distributed between icy water and Et$_2$O. The organic layer was washed with water and dried with MgSO$_4$. Evaporation of the solvent and column chromatography on silica gel with hexane/EtOAc 9:1 gave of 3.2 g (80%) 5-Bromo-6-fluoro-1H-indole, MS: 213 (M, 1Br).

23.3

A mixture of 0.07 g (5 mmol) 5-Bromo-6-fluoro-1H-indole (1, 1-chloro-4-iodobenzene (2.5 g, 10.5 mmol), 250 mg (1.31 mmol) CuI, 80 mg (0.9 mmol) ZnO, and 1.75 g (12.67 mmol) K$_2$CO$_3$ in degassed NMP was stirred at 170° C. during 6 hours in a pressure tube. After cooling to room temperature, the mixture was poured into 50 ml of saturated aqueous NaCl and extracted three times with Et$_2$O. Drying of the combined organic layers with Na$_2$SO$_4$, evaporation of the solvent, and column chromatography on silica gel with CH$_2$Cl$_2$/hexane 1:2 gave 0.98 g (60%) 5-Bromo-1-(4-chloro-phenyl)-6-fluoro-1H-indole as a yellowish-grey solid, MS: 323 (M, 1Cl, 1Br). (Analogously to Jens Perregaard et. al. J. Med. Chem. 1992, 35, 4813–4822.)

23.4

In analogy to example 23.3, 5-Bromo-6-fluoro-1H-indole and 1-fluoro-4-iodobenzene were converted to yield 5-Bromo-1-(4-fluoro-phenyl)-6-fluoro-1H-indole as a light yellow solid, MS: 307 (M, 1Br).

23.5

A solution of 1.05 g (3.2 mmol) 5-Bromo-1-(4-chloro-phenyl)-6-fluoro-1H-indole in THF at −78° C. was treated dropwise with 3 ml (4.8 mmol) 1.6 M BuLi in hexane, stirred during around 30 min, treated with 1.5 ml (6.5 mmol) triisopropylborate, stirred for 10 min at −78° C. and then for 30 min at 0° C. A mixture of 0.8 ml H$_2$O and 0.8 ml AcOH was added dropwise, the resulting mixture treated within 15 min with 0.5 ml of H$_2$O$_2$ (35% in H$_2$O ), stirred for 30 min at 0° C., and 1 h at room temperature. The mixture was diluted with 50 ml of Et$_2$O, 40 ml of saturated aqueous NaCl, and 10 ml of 1M aqueous Na$_2$S$_2$O$_3$ and stirred during 2 hours at room temperature. The organic layer was dried with MgSO$_4$ and the solvent evaporated. Column chromatography on silica gel with (Et$_2$O/hexane 1:2) gave 594 mg (70%) 1-(4-Chloro-phenyl)-6-fluoro-1H-indol-5-ol as a light brown solid. The solid was dissolved in 1.5 ml DMF and treated with grinded 740 mg $K_2CO_3$ and 900 mg 1,4-dibromobutane and stirred during 2 hours at 80° C. The mixture was poured into saturated aqueous NaCl and extracted three times with $Et_2O$. Drying of the combined organic layers with $Na_2SO_4$, evaporation of the solvent, and column chromatography on silica gel with hexane/$Et_2O$ 3:1 gave 180 mg (14%) 5-(4-Bromo-butoxy)-1-(4-chloro-phenyl)-6-fluoro-1H-indole as a light brown solid, MS: 395 (M, 1Cl, 1Br).

23.6

In analogy to example 23.5, 5-Bromo-1-(4-fluoro-phenyl)-6-fluoro-1H-indole was converted to yield 5-(4-Bromo-butoxy)-6-fluoro-1-(4-fluoro-phenyl)-1H-indole, as a light yellow solid, MS: 379 (M, 1Br).

23.7

30 mg (0.076 mmol) 5-(4-Bromo-butoxy)-1-(4-chloro-phenyl)-6-fluoro-1H-indole in 0.25 ml DMF were treated with 75 µl of N-Allylmethylamine and stirred at 80° C. during 1 h. The mixture was treated with 0.5M aqueous NaOH and extracted three times with $Et_2O$. Drying of the combined organic layers with $Na_2SO_4$, evaporation of the solvent and column chromatography on silica gel with hexane/EtOAc 1:1 gave 25 mg (85%) Allyl-{4-[1-(4-chloro-phenyl)-6-fluoro-1H-indol-5-yloxy]-butyl}-methyl-amine as a light yellow oil, MS: 387 ($MH^+$, 1Cl).

23.8

In analogy to example 23.7 5-(4-Bromo-butoxy)-1-(4-fluoro-phenyl)-6-fluoro-1H-indole was converted to yield Allyl-{4-[1-(4-Fluoro-phenyl)-6-fluoro-1H-indol-5-yloxy]-butyl}-methyl-amine as light yellow oil, MS: 371 ($MH^+$).

23.9

In analogy to example 23.7, 5-(4-Bromo-butoxy)-1-(4-chloro-phenyl)-6-fluoro-1H-indole and 2-(methylamino) ethanol were converted to yield 2-({4-[1-(4-Chloro-phenyl)-6-fluoro-1H-indol-5-yloxy]-butyl}-methyl-amino)-ethanol as a colorless oil, MS: 391 ($MH^+$,1Cl).

23.10

In analogy to example 23.7, 5-(4-Bromo-butoxy)-1-(4-fluoro-phenyl)-6-fluoro-1H-indole was converted to yield 2-({4-[1-(4-Fluoro-phenyl)-6-fluoro-1H-indol-5-yloxy]-butyl}-methyl-amino)-ethanol, MS: 375 ($MH^+$).

23.11

In analogy to example 23.7, 5-(4-Bromo-butoxy)-1-(4-chloro-phenyl)-6-fluoro-1H-indole and 2-(ethylamino) ethanol were converted to yield 2-({4-[1-(4-Chloro-phenyl)-6-fluoro-1H-indol-5-yloxy]-butyl}-ethyl-amino)-ethanol as a colorless oil, MS: 405 ($MH^+$).

23.12

In analogy to example 23.7, 5-(4-Bromo-butoxy)-1-(4-fluoro-phenyl)-6-fluoro-1H-indole and 2-(ethylamino) ethanol were converted to yield 2-({4-[1-(4-Fluoro-phenyl)-6-fluoro -1H-indol-5-yloxy]-butyl}-ethyl-amino)-ethanol as light yellow oil, MS: 389 ($MH^+$).

Example 24

24.1

A mixture of 102 mg (0.331 mmol) 5-Bromo-1-(4-chloro-phenyl)-6-fluoro-1H-indole, 22 mg (0.019 mmol) Pd($PPh_3$)$_4$, 4 mg (0.021 mmol) CuI in 1 ml piperidine was heated to 60° C. and treated with 55 µl (0.595 mmol) 4-pentyn-1-ol. After stirring at 80° C. during 3 hours the mixture was cooled to room temperature, poured into 0.5M aqueous HCl and extracted three times with $Et_2O$. Drying of the combined organic layers with $Na_2SO_4$, evaporation of the solvent, and column chromatography on silica gel with $CH_2Cl_2$ gave 92 mg (89%) 5-[6-Fluoro-1-(4-fluoro-phenyl)-1H-indol-5-yl]-pent-4-yn-1-ol as a light brown oil, MS: 311 ($M^+$).

24.2

A solution of 87 mg (0.28 mmol) 5-[6-Fluoro-1-(4-fluoro-phenyl)-1H-indol-5-yl]-pent-4-yn-1-ol in 3 ml $CH_2Cl_2$ was treated with 0.14 ml (1 mmol) $NEt_3$ and 80 µl (0.33 mmol) MsCl, stirred at room temperature for one hour, poured into icy 0.5 M aqueous HCl and extracted three times with $Et_2O$. Drying of the combined organic layers with $Na_2SO_4$ and evaporation of the solvent gave (93 mg) Methanesulfonic acid 5-[6-fluoro-1-(4-fluoro-phenyl)-1H-indol-5-yl]-pent-4-ynyl ester as a light brown oil. 31 mg of this oil were dissolved in DMF, treated with 0.2 ml Allylmethylamine and the mixture stirred at 80° C. during 2 hours. Pouring the mixture into 0.5 M NaOH, extraction with $CH_2Cl_2$, drying of the organic layers with $MgSO_4$, and flash chromatography with $CH_2Cl_2$/MeOH 19:1 gave 24 mg (89%) Allyl-{5-[6-fluoro-1-(4-fluoro-phenyl)-1H-indol-5-yl]-pent-4-ynyl}-methyl-amine as a light yellow oil, MS: 365 ($MH^+$).

24.3

In analogy to example 24.2, 5-[6-Fluoro-1-(4-fluoro-phenyl)-1H-indol-5-yl]-pent-4-yn-1-ol and 2-(Etylamino) ethanol were converted to yield 2-({5-[6-Fluoro-1-(4-fluoro-phenyl)-1H-indol-5-yl]-pent-4-ynyl}-ethyl-amino)-ethanol as a colorless oil, MS: 383 ($MH^+$).

Example 25

25.1

A solution of 25 mg (0.67 mol) Allyl-{4-[1-(4-chloro-phenyl)-6-fluoro-1H-indol-5-yloxy]-butyl}-methyl-amine in 1 ml AcOH/TFA (1:1) was treated at 0° C. with 70 mg (1.11 mmol) $NaBCNH_3$ and stirred at room temperature for 8 hours. The mixture was poured into icy 2M NaOH and extracted three times with $Et_2O$. Evaporation of the solvent, drying with $MgSO_4$ and column chromatography on silica gel with $CH_2Cl_2$/MeOH/$NEt_3$ 10:1:0.1 gave 20 mg (80%) Allyl-{4-[1-(4-chloro-phenyl)-6-fluoro-2,3-dihydro-1H-indole-5-yloxy]-butyl}-methyl-amine, MS: 389 ($MH^+$).

Example 26

26.1

300 mg (0.96 mmol) {4-[1-(4-Fluoro-phenyl)-1H-indol-5-yloxy]-butyl}-methylamine in 10 ml THF were treated with 150 mg (1.4 mmol) 2-chloroethylisocyanate and the mixture stirred at room temperature during 10 hours. After addition of 0.2 ml $NEt_3$ the mixture was stirred for an additional hour and treated with 0.1 M aqueous HCl. Extraction with $Et_2O$, drying of the combined organic layers with $Na_2SO_4$, Evaporation of the solvent, and column chromatography on silica gel with $CH_2Cl_2$/MeOH/$NEt_3$ 10:1:0.1 gave 60 mg (16%) (4,5-Dihydro-oxazol-2-yl)-{4-[1-(4-fluoro-phenyl)-1H-indol-5-yloxy]-butyl}-methyl-amine, MS: 382 ($MH^+$).

26.2

50 mg (0.138 mmol) {4-[1-(4-Fluoro-phenyl)-1H-indol-5-yloxy]-butyl}-methylamine in 1.5 ml THF were treated with 25 mg (0.21 mmol) 2-chloroethylthioisocyanate stirred for one hour at room temperature and then treated with ca. 50 µl of triethylamine. Evaporation of the solvent and column chromatography on silica gel with $CH_2Cl_2$/MeOH/ $NEt_3$ 19:1:0.1 gave 35 mg (64%) of (4,5-Dihydro-thiazol-2-yl)-{4-[1-(4-fluoro-phenyl)-1H-indol-5-yloxy]-butyl}-methyl-amine as a light yellowish oil, MS: 399 ($MH^+$).

Example 27

27.1

A mixture of 30 mg (0.091 mmol) {4-[1-(4-Fluoro-phenyl)-1H-indol-5-yloxy]-butyl}-methylamine, 2 mg (0.009 mmol) Pd(OAc)$_2$, 7 mg (0.02 mmol) (dicyclohexylphosphino)-biphenyl, 44 mg (0.46 mmol)

sodium tert-butoxide, and 20 mg (0.1 mmol) 4-bromopyridine hydrochloride in 1 ml of degassed toluene was stirred in a pressure tube at 120° C. during 16 hours. After cooling to room temperature the mixture was treated with 0.5M aqueous NaOH and extracted three times with Et$_2$O. Drying of the combined organic layers with Na$_2$SO$_4$, evaporation of the solvent, and column chromatography on silica gel with EtOAc/NEt$_3$ 100:3 gave 30 mg (81%) of {4-[1-(4-Fluoro-phenyl)-1H-indol-5-yloxy]-butyl}-methyl-pyridin-4-yl-amine as a light yellow oil, MS: 390 (MH$^+$). (In analogy to L. Buchwald et al. J. Org. Chem. 2000, 65, 1158–1174).

27.2

In analogy to example 28.1, {4-[1-(4-Fluoro-phenyl)-1H-indol-5-yloxy]-butyl}-methylamine and 3-Bromopyridine were converted to yield 4-[1-(4-Fluoro-phenyl)-1H-indol-5-yloxy]-butyl}-methyl-pyridin-3-yl-amine as a colorless oil, MS: 390 (MH$^+$).

27.3

A solution of 100 mg (0.303 mmol) {4-[1-(4-Fluoro-phenyl)-1H-indol-5-yloxy]-butyl}-methylamine in 2 ml 2-chloropyridine was treated with 100 mg KOH and stirred in a pressure tube at 165° C. during 6 hours. After cooling to room temperature the mixture was treated with saturated aqueous NaCl and extracted three times with Et$_2$O. Drying of the combined organic layers with Na$_2$SO$_4$, evaporation of the solvent, and column chromatography on silica gel with EtOAc/MeOH/NEt$_3$ 5:1:0.1 gave 42 mg (30%) 4-[1-(4-Fluoro-phenyl)-1H-indol-5-yloxy]-butyl}-methyl-pyridin-2-yl-amine as colorless oil, MS: 390 (MH$^+$).

27.4

20 mg (0.064 mmol) {4-[1-(4-Fluoro-phenyl)-1H-indol-5-yloxy]-butyl}-methylamine and 0.16 ml (0.96 mmol) N,N-diisopropyl ethyl amine in 1 ml of DMF were treated with 41 mg (0.32 mmol) 4-chloro-2-methylpyrimidine and stirred at 100° C. during 2 hours. After cooling to room temperature the mixture was treated with saturated aqueous NaCl and extracted three times with Et$_2$O. Drying of the combined organic layers over Na$_2$SO$_4$, evaporation of the solvent and column chromatography on silica gel with EtOAc gave 19 mg (73%) {4-[1-(4-Fluoro-phenyl)-1H-indol-5-yloxy]-butyl}-methyl-(2-methyl-pyrimidin-4-yl)-amine as a light yellow oil, MS: 405 (MH$^+$).

Example A

Tablets containing the following ingredients can be manufactured in a conventional manner:

| Ingredients | Per tablet |
| --- | --- |
| Compound of formula I | 10.0–100.0 mg |
| Lactose | 125.0 mg |
| Maize starch | 75.0 mg |
| Talc | 4.0 mg |
| Magnesium stearate | 1.0 mg |

Example B

Capsules containing the following ingredients can be manufactured in a conventional manner:

| Ingredients | Per capsule |
| --- | --- |
| Compound of formula I | 25.0 mg |
| Lactose | 150.0 mg |
| Maize starch | 20.0 mg |
| Talc | 5.0 mg |

Example C

Injection solutions can have the following composition:

| Compound of formula I | 3.0 mg |
| --- | --- |
| Gelatine | 150.0 mg |
| Phenol | 4.7 mg |
| Water for injection solutions | ad 1.0 ml |

What is claimed is:
1. A compound selected from the group consisting of: compounds of formula (I)

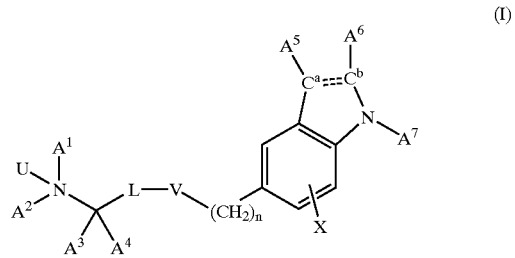

wherein
the bond ═ between the carbon atom C$^a$ and the carbon atom C$^b$ is a single or a double bond,
U is O or a lone pair,
V is a) O, S, NR$^1$, or CH$_2$, and L is lower-alkylene or lower-alkenylene or b) —CH═CH— or —C≡C—, and L is lower-alkylene or a single bond,
n is 0 to 7,
X is hydrogen or one or more optional halogen and/or lower-alkyl substituents,
A$^1$ is hydrogen, lower-alkenyl, or lower-alkyl optionally substituted by hydroxy, lower-alkoxy, or thio-lower-alkoxy,
A$^2$ is cycloalkyl, cycloalkyl-lower-alkyl, lower-alkenyl, lower-alkinyl, heterocyclyl, or lower-alkyl optionally substituted by hydroxy, lower-alkoxy or thio-lower-alkoxy,
A$^3$ and A$^4$ independently from each other are hydrogen or lower-alkyl, or
A$^1$ and A$^2$ or A$^1$ and A$^3$ are bonded to each other to form a ring and —A$^1$—A$^2$— or
—A$^1$—A$^3$— are lower-alkylene or lower-alkenylene, optionally substituted by R$^2$, in which one —CH$_2$— group of —A$^1$—A$^2$— or —A$^1$—A$^3$— can optionally be replaced by NR$^3$, S, or O,
A$^5$ and A$^6$ independently from each other are hydrogen or lower-alkyl,
A$^7$ is alkyl with two or more carbon atoms, alkenyl, alkadienyl, cycloalkyl, cycloalkyl-lower-alkyl, aryl, or aryl-lower-alkyl, R² is hydroxy, lower-alkoxy, thio-lower-alkoxy, N(R⁴, R⁵), or lower-alkyl optionally substituted by hydroxy,
R¹, R³, R⁴ and R⁵ independently from each other are hydrogen or lower-alkyl;
pharmaceutically acceptable salts of compounds of formula (I);
and pharmaceutically acceptable esters of compounds of formula (I).

2. The compound according to claim 1, wherein A² is cycloalkyl, cycloalkyl-lower-alkyl, lower-alkenyl, lower-alkinyl, or lower-alkyl optionally substituted by hydroxy, lower-alkoxy or thio-lower-alkoxy.

3. The compound according to claim 1, wherein U is a lone pair.

4. The compound according to claim 3, wherein V is O or CH₂ and L is lower-alkylene.

5. The compound according to claim 3, wherein V is O and L is lower-alkenylene.

6. The compound according to claim 3, wherein V is —C≡C— and L is lower-alkylene or a single bond.

7. The compound according to claim 3, wherein n is 0.

8. The compound according to claim 7, wherein A¹ is hydrogen or lower-alkyl optionally substituted with hydroxy.

9. The compound according to claim 8, wherein A¹ is methyl or ethyl optionally substituted with hydroxy.

10. The compound according to claim 9, wherein A² is cycloalkyl, cycloalkyl-lower-alkyl, lower-alkenyl, lower-alkinyl, or lower-alkyl optionally substituted by hydroxy or lower-alkoxy.

11. The compound according to claim 9, wherein A² is pyridinyl, 2-methyl-pyrimidinyl, 4,5-dihydro-oxazolyl or 4,5-dihydro-thiazolyl.

12. The compound according to claim 9, wherein A² is pyridin-4-yl.

13. The compound according to claim 10, wherein A² is methyl, ethyl, 2-hydroxy-ethyl, n-propyl, or 2-propenyl.

14. The compounds according to claim 7, wherein A¹ and A² are bonded to each other to form a ring and —A¹—A²— is lower-alkylene or lower-alkenylene, optionally substituted by R², in which one —CH₂— group of —A¹—A²— can optionally be replaced by O, wherein R² is hydroxy.

15. The compound according to claim 14, wherein —A¹—A²— is —(CH₂)₂—O—(CH₂)₂—.

16. The compound according to claim 7, wherein A³ is hydrogen.

17. The compound according to claim 7, wherein A³ is methyl.

18. The compound according to claim 7, wherein A⁴ is hydrogen.

19. The compound according to claim 7, wherein A⁴ is methyl.

20. The compound according to claim 7, wherein A⁵ is hydrogen or methyl.

21. The compound according to claim 20, wherein A⁶ is hydrogen or methyl.

22. The compound according to claim 7, wherein A⁷ is lower-alkenyl, lower-alkadienyl, aryl, or aryl-lower-alkyl.

23. The compound according to claim 22, wherein A⁷ is phenyl or benzyl, optionally substituted by 1 to 3 substituents independently selected from the group consisting of fluorine, chlorine, bromine, CF₃, ethyl, ethinyl, and phenyl.

24. The compound according to claim 23, wherein A⁷ is 4-fluoro-phenyl, 4-chloro-phenyl, 4-bromo-phenyl, or 4-trifluoro-phenyl.

25. The compound according to claim 23, wherein X is hydrogen.

26. The compound according to claim 23, wherein X is fluorine.

27. The compound according to claim 3, wherein the bond ═ between the carbon atom Cᵃ and the carbon atom Cᵇ is a double bond.

28. A compound selected from the group consisting of:
compounds of formula (VII)

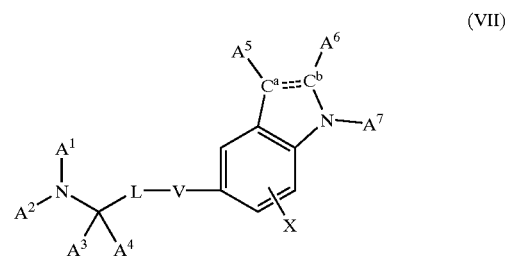

(VII)

wherein
the bond ═ between the carbon atom Cᵃ and the carbon atom Cᵇ is a single or a double bond;
V is a) O or CH₂ and L is lower-alkylene or lower-alkenylene or b) —C≡C— and L is lower-alkylene or a single bond;
X is hydrogen or one or more halogen substituents;
A¹ is hydrogen, lower-alkyl or lower-alkoxy, and A² is cycloalkyl, lower-alkenyl, lower-alkinyl, heterocyclyl or lower-alkyl optionally substituted by hydroxy, cycloalkyl or lower-alkoxy, or
A¹ and A² are bonded to each other to form lower alkenylene, lower alkylene substituted by OH or lower alkylene in which one —CH₂— group is optionally substituted by O;
A³, A⁴, A⁵ and A⁶ are hydrogen or lower-alkyl; and
A⁷ is phenyl or lower alkyl phenyl, wherein the phenyl group is optionally substituted with halogen, phenyl, alkyl, alkinyl or trifluoromethyl;
pharmaceutically acceptable salts of compounds of formula (VII);
and pharmaceutically acceptable esters of compounds of formula (VII).

29. The compound according to claim 28, selected from the group consisting of:
compounds of formula (VIII)

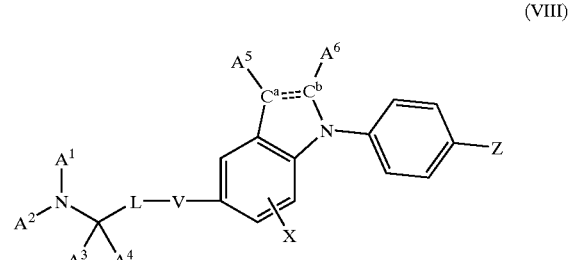

(VIII)

wherein
the bond ═ between the carbon atom Cᵃ and the carbon atom Cᵇ is a single or a double bond;
V is a) O or CH₂ and L is lower-alkylene or lower-alkenylene or b) —C≡C— and L is lower-alkylene or a single bond;
X is hydrogen or one or more halogen substituents;

Z is halogen or trifluoromethyl;

$A^1$ is lower-alkyl or lower-alkoxy, and $A^2$ is lower-alkyl, lower alkoxy, lower-alkenyl or a heterocyclyl having a single N hetero atom, or $A^1$ and $A^2$ are bonded to each other to form lower-alkylene in which one —CH$_2$— group is optionally substituted by O; and $A^3$, $A^4$, $A^5$ and $A^6$ are hydrogen or lower-alkyl;

pharmaceutically acceptable salts of compounds of formula (VIII)

and pharmaceutically acceptable esters of compounds of formula (VIII).

30. The compound according to claim 29, wherein the bond === between the carbon atom $C^a$ and the carbon atom $C^b$ is a single bond.

31. The compound according to claim 30, wherein the compound of formula (VIII) is allyl-{6-[1-(4-fluoro-phenyl)-2,3-dihydro-1H-indol-5-yloxy]-hexyl}-methyl-amine.

32. The compound according to claim 31, which is allyl-{6-[1-(4-fluoro-phenyl)-2,3-dihydro-1H-indol-5-yloxy]-hexyl}-methyl-amine.

33. The compound according to claim 29, wherein the bond === between the carbon atom $C^a$ and the carbon atom $C^b$ is a double bond.

34. The compound according to claim 33, wherein V is O.

35. The compound according to claim 34, wherein X is H.

36. The compound according to claim 35, wherein $A^1$ and $A^2$ are bonded together to form a lower alkylene in which one —CH$_2$— group is substituted by O.

37. The compound according to claim 36, wherein the compound of formula (VIII) is 1-(4-fluoro-phenyl)-5-(4-morpholin-4-yl-butoxy)-1H-indole.

38. The compound according to claim 37, which is 1-(4-fluoro-phenyl)-5-(4-morpholin-4-yl-butoxy)-1H-indole.

39. The compound according to claim 35, wherein $A^2$ is pyridinyl.

40. The compound according to claim 39, wherein the compound of formula (VIII) is {4-[1-(4-fluoro-phenyl)-1H-indol-5-yloxy]-butyl}-methyl-pyridin-4-yl-amine.

41. The compound according to claim 40, which is {4-[1-(4-fluoro-phenyl)-1H-indol-5-yloxy]-butyl}-methyl-pyridin-4-yl-amine.

42. The compound according to claim 35, wherein $A^2$ is lower alkyl.

43. The compound according to claim 42, wherein the compound of formula (VIII) is {4-[1-(4-fluoro-phenyl)-1H-indol-5-yloxy]-butyl}-methyl-propyl-amine.

44. The compound according to claim 43, which is {4-[1-(4-fluoro-phenyl)-1H-indol-5-yloxy]-butyl}-methyl-propyl-amine.

45. The compound according to claim 42, wherein the compound of formula (VIII) is diethyl-{4-[1-(4-fluoro-phenyl)-1H-indol-5-yloxy]-butyl}-amine.

46. The compound according to claim 45, which is diethyl-{4-[1-(4-fluoro-phenyl)-1H-indol-5-yloxy]-butyl}-amine.

47. The compound according to claim 35, wherein $A^2$ is lower alkoxy.

48. The compound according to claim 47, wherein the compound of formula (VIII) is 2-(ethyl-{4-[1-(4-fluoro-phenyl)-1H-indol-5-yloxy]-butyl}-amino)-ethanol.

49. The compound according to claim 48, which is 2-(ethyl-{4-[1-(4-fluoro-phenyl)-1H-indol-5-yloxy]-butyl}-amino)-ethanol.

50. The compound according to claim 47, wherein the compound of formula (VIII) is 2-[{4-[1-(4-fluoro-phenyl)-1H-indol-5-yloxy]-butyl}-(2-hydroxy-ethyl)-amino]-ethanol.

51. The compound according to claim 50, which is 2-[{4-[1-(4-fluoro-phenyl)-1H-indol-5-yloxy]-butyl}-(2-hydroxy-ethyl)-amino]-ethanol.

52. The compound according to claim 47, wherein the compound of formula (VIII) is 2-({4-[1-(4-bromo-phenyl)-1H-indol-5-yloxy]-butyl}-ethyl-amino)-ethanol.

53. The compound according to claim 52, which is 2-({4-[1-(4-bromo-phenyl)-1H-indol-5-yloxy]-butyl}-ethyl-amino)-ethanol.

54. The compound according to claim 47, wherein the compound of formula (VIII) is 2-(ethyl-{4-[1-(4-fluoro-phenyl)-1H-indol-5-yloxy]-but-2-enyl}-amino)-ethanol.

55. The compound according to claim 54, which is 2-(ethyl-{4-[1-(4-fluoro-phenyl)-1H-indol-5-yloxy]-but-2-enyl}-amino)-ethanol.

56. The compound according to claim 35, wherein $A^2$ is lower alkenyl.

57. The compound according to claim 56, wherein the compound of formula (VIII) is allyl-{6-[1-(4-fluoro-phenyl)-1H-indol-5-yloxy]-hexyl}-methyl-amine.

58. The compound according to claim 57, which is allyl-{6-[1-(4-fluoro-phenyl)-1H-indol-5-yloxy]-hexyl}-methyl-amine.

59. The compound according to claim 56, wherein the compound of formula (VIII) is allyl-{4-[1-(4-fluoro-phenyl)-1H-indol-5-yloxy]-butyl}-methyl-amine.

60. The compound according to claim 59, which is allyl-{4-[1-(4-fluoro-phenyl)-1H-indol-5-yloxy]-butyl}-methyl-amine.

61. The compound according to claim 34, wherein X is F.

62. The compound according to claim 61, wherein $A^2$ is alkyl.

63. The compound according to claim 61, wherein $A^2$ is alkoxy.

64. The compound according to claim 63, wherein the compound of formula (VIII) is 2-({4-[1-(4-chloro-phenyl)-6-fluoro-1H-indol-5-yloxy]-butyl}-methyl-amino)-ethanol.

65. The compound according to claim 64, which is 2-({4-[1-(4-chloro-phenyl)-6-fluoro-1H-indol-5-yloxy]-butyl}-methyl-amino)-ethanol.

66. The compound according to claim 63, wherein the compound of formula (VIII) is 2-({4-[6-fluoro-1-(4-fluoro-phenyl)-1H-indol-5-yloxy]-butyl}-methyl-amino)-ethanol.

67. The compound according to claim 66, which is 2-({4-[6-fluoro-1-(4-fluoro-phenyl)-1H-indol-5-yloxy]-butyl}-methyl-amino)-ethanol.

68. The compound according to claim 63, wherein the compound of formula (VIII) is 2-({4-[1-(4-chloro-phenyl)-6-fluoro-1H-indol-5-yloxy]-butyl}-ethyl-amino)-ethanol.

69. The compound according to claim 68, which is 2-({4-[1-(4-chloro-phenyl)-6-fluoro-1H-indol-5-yloxy]-butyl}-ethyl-amino)-ethanol.

70. The compound according to claim 63, wherein the compound of formula (VIII) is 2-(ethyl-{4-[6-fluoro-1-(4-fluoro-phenyl)-1H-indol-5-yloxy]-butyl}-amino)-ethanol.

71. The compound according to claim 70, which is 2-(ethyl-{4-[6-fluoro-1-(4-fluoro-phenyl)-1H-indol-5-yloxy]-butyl}-amino)-ethanol.

72. The compound according to claim 61, wherein $A^2$ is alkenyl.

73. The compound according to claim 72, wherein the compound of formula (VIII) is allyl-{4-[6-fluoro-1-(4-fluoro-phenyl)-1H-indol-5-yloxy]-butyl}-methyl-amine.

74. The compound according to claim 73, which is allyl-{4-[6-fluoro-1-(4-fluoro-phenyl)-1H-indol-5-yloxy]-butyl}-methyl-amine.

75. The compound according to claim 33, wherein V is $CH_2$.

76. The compound according to claim 75, wherein the compound of formula (VIII) is allyl-{5-[1-(4-fluoro-phenyl)-1H-indol-5-yl]-pentyl}-methyl-amine.

77. The compound according to claim 76, which is allyl-{5-[1-(4-fluoro-phenyl)-1H-indol-5-yl]-pentyl}-methyl-amine.

78. The compound according to claim 75, wherein the compound of formula (VIII) is 2-(ethyl-{5-[1-(4-fluoro-phenyl)-1H-indol-5-yl]-pentyl}-amino)-ethanol.

79. The compound according to claim 78, which is 2-(ethyl-{5-[1-(4-fluoro-phenyl)-1H-indol-5-yl]-pentyl}-amino)-ethanol.

80. The compound according to claim 75, wherein the compound of formula (VIII) is allyl-{5-[1-(4-chloro-phenyl)-1H-indol-5-yl]-pentyl}-methyl-amine.

81. The compound according to claim 80, which is allyl-{5-[1-(4-chloro-phenyl)-1H-indol-5-yl]-pentyl}-methyl-amine.

82. The compound according to claim 75, wherein the compound of formula (VIII) is 2-(ethyl-{5-[1-(4-fluoro-phenyl)-3-methyl-1H-indol-5-yl]pentyl}-amino)-ethanol.

83. The compound according to claim 82, which is 2-(ethyl-{5-[1-(4-fluoro-phenyl)-3-methyl-1H-indol-5-yl]pentyl}-amino)-ethanol.

84. The compound according to claim 33, wherein V is —C≡C—.

85. The compound according to claim 84, wherein the compound of formula (VIII) is allyl-{5-[1-(4-bromo-phenyl)-3-methyl-1H-indol-5-yl]pent-4-ynyl}-methyl-amine.

86. The compound according to claim 85, which is allyl-{5-[1-(4-bromo-phenyl)-3-methyl-1H-indol-5-yl]pent-4-ynyl}-methyl-amine.

87. The compound according to claim 84, wherein the compound of formula (VIII) is allyl-methyl-{5-[3-methyl-1-(4-trifluoromethyl-phenyl)-1H-indol-5-yl]pent-4-ynyl}-amine.

88. The compound according to claim 87, which is allyl-methyl-{5-[3-methyl-1-(4-trifluoromethyl-phenyl)-1H-indol-5-yl]pent-4-ynyl}-amine.

89. The compound according to claim 84, wherein the compound of formula (VIII) is 2-(ethyl-{3-[1-(4-fluoro-phenyl)-1H-indol-5-yl]1,1-dimethyl-prop-2-ynyl}-amino)-ethanol.

90. The compound according to claim 89, which is 2-(ethyl-{3-[1-(4-fluoro-phenyl)-1H-indol-5-yl]-1,1-dimethyl-prop-2-ynyl}-amino)-ethanol.

91. The compound according to claim 84, wherein the compound of formula (VIII) is 2-(ethyl-{5-[6-fluoro-1-(4-fluoro-phenyl)-1H-indol-5-yl]-pent-4-ynyl}-amino)-ethanol.

92. The compound according to claim 91, which is 2-(ethyl-{5-[6-fluoro-1-(4-fluoro-phenyl)-1H-indol-5-yl]-pent-4-ynyl}-amino)-ethanol.

93. A process for the manufacture of a compound according to claim 1, which process comprises a) reacting a compound of formula (II)

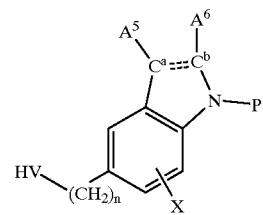

(II)

with a compound $(A^1, A^2, U)N-C(A^3, A^4)-L-M$, wherein V is O, S or $NR^1$, M is mesylate, tosylate, Cl, Br or I, P is $A^7$ or a protecting group, and U, $A^1$, $A^2$, $A^3$, $A^4$, $A^5$, $A^6$, $A^7$, X, L, n, $R^1$ and the bond ═══ between the carbon atom $C^a$ and the carbon atom $C^b$ have the significances given in claim 1, or wherein HV is mesylate, tosylate, triflate, Cl, Br or I, and M is OH, SH or $NHR^1$, and $R^1$ has the significance given in claim 1, or b) reacting a compound of formula (III)

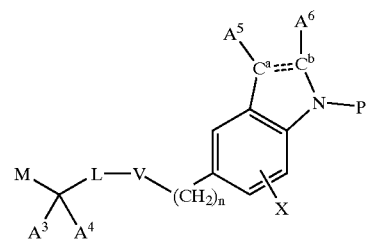

(III)

with a compound $NHA^1, A^2$, wherein M is mesylate, tosylate, triflate, Cl, Br or I, P is $A^7$ or a protecting group, and $A^1$, $A^2$, $A^3$, $A^4$, $A^5$, $A^6$, $A^7$, L, V, X, n and the bond ═══ between the carbon atom $C^a$ and the carbon atom $C^b$ are as defined in claim 1, or c) reacting a compound of formula (IV)

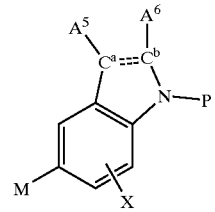

(IV)

with a compound $(A^1, A^2, U)N-C(A^3, A^4)-L-C≡CH$, wherein M is Cl, Br, I or $F_3CO_2SO$, P is $A^7$ or a protecting group, and U, $A^1$, $A^2$, $A^3$, $A^4$, $A^5$, $A^6$, $A^7$, U, L, X and the bond ═══ between the carbon atom $C^a$ and the carbon atom $C^b$ are as defined in claim 1, or d) reacting a compound of formula (V)

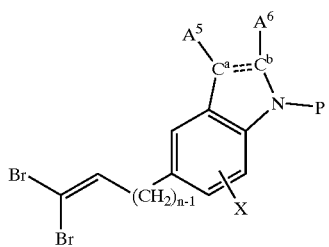

(V)

with a compound $(A^1,A^2,U)N—C(A^3,A^4)—L—M$, wherein M is mesylate, tosylate, triflate, Cl, Br or I, P is $A^7$ or a protecting group, and $A^1$, $A^2$, $A^3$, $A^4$, $A^5$, $A^6$, $A^7$, U, L, X, n and the bond ═══ between the carbon atom $C^a$ and the carbon atom $C^b$ are as defined in claim 1, or e) hydrogenating a compound of formula (VI)

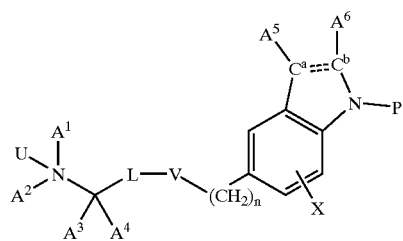

(VI)

wherein V is —C≡C—, P is $A^7$ or a protecting group, and $A^1$, $A^2$, $A^3$, $A^4$, $A^5$, $A^6$, $A^7$, U, L, X and n are as defined in claim 1.

94. A pharmaceutical composition comprising a compound according to claim 29 and at least one of a pharmaceutically acceptable carrier or pharmaceutically acceptable adjuvant.

95. A method for the treatment or prophylaxis of disease which are associated with 2,3-oxidosqualene:lanosterol cyclase, which method comprises administering a compound according to claim 29 to a patient in need of such treatment.

96. The method of claim 95 wherein the treatment or prophylaxis of diseases which is associated with 2,3-oxidosqualene:lanosterol cyclase is hypercholesterolemia, hyperlipemia, arteriosclerosis, vascular diseases, mycoses, parasite infections, gallstones, tumor disorders, hyperproliferative disorder, treatment of impaired glucose tolerance, prophylaxis of impaired glucose tolerance or diabetes.

\* \* \* \* \*